(12) United States Patent
Lu et al.

(10) Patent No.: US 11,312,705 B2
(45) Date of Patent: Apr. 26, 2022

(54) HETEROARYL[4,3-C]PYRIMIDINE-5-AMINE DERIVATIVE, PREPARATION METHOD THEREFOR, AND MEDICAL USES THEREOF

(71) Applicants: Jiangsu Hengrui Medicine Co., Ltd., Jiangsu (CN); Shanghai Hengrui Pharmaceutical Co., Ltd., Shanghai (CN)

(72) Inventors: Biao Lu, Shanghai (CN); Shenglan Wang, Shanghai (CN); Xiaodong Shen, Shanghai (CN); Feng He, Shanghai (CN); Weikang Tao, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 94 days.

(21) Appl. No.: 16/492,273

(22) PCT Filed: Mar. 15, 2018

(86) PCT No.: PCT/CN2018/079086
§ 371 (c)(1),
(2) Date: Sep. 9, 2019

(87) PCT Pub. No.: WO2018/166493
PCT Pub. Date: Sep. 20, 2018

(65) Prior Publication Data
US 2021/0032224 A1    Feb. 4, 2021

(30) Foreign Application Priority Data

Mar. 16, 2017 (CN) .......................... 201710156742.7
Oct. 20, 2017 (CN) .......................... 201710982734.8

(51) Int. Cl.
*C07D 487/04* (2006.01)
*C07D 403/14* (2006.01)
*C07D 401/14* (2006.01)
*C07D 405/14* (2006.01)

(52) U.S. Cl.
CPC ......... *C07D 403/14* (2013.01); *C07D 401/14* (2013.01); *C07D 405/14* (2013.01)

(58) Field of Classification Search
CPC .................................................. C07D 487/04
See application file for complete search history.

(56) References Cited

U.S. PATENT DOCUMENTS 9,580,437 B2 * 2/2017 Chan .................... A61K 31/519
2010/0331294 A1   12/2010 Black et al.
2015/0361100 A1   12/2015 Biagetti et al.

FOREIGN PATENT DOCUMENTS

| CN | 1328560 A | 12/2001 |
| DE | 102006008880 A1 | 9/2007 |
| EP | 1116722 A1 | 7/2001 |
| JP | 2002037787 A | 2/2002 |
| WO | 03068776 A1 | 8/2003 |
| WO | 2006138734 A1 | 12/2006 |
| WO | 2007116106 A1 | 10/2007 |
| WO | 2009080197 A1 | 7/2009 |
| WO | 2009111449 A1 | 9/2009 |
| WO | 2011070131 A1 | 6/2011 |
| WO | 2011095625 A1 | 8/2011 |

(Continued)

OTHER PUBLICATIONS

Csoka et al., Adenosine promotes alternative macrophage activation via A2a and A2b receptors, The FASEB Journal, vol. 26, pp. 376-386, Jan. 2012.*
Damasio, Alzheimer's Disease and related dementias, Cecil Textbook of Medicine, 20th Edition, vol. 2, pp. 1992-1996, 1996.*
Layzer, Degenerative diseases of the nervous system, Cecil Textbook of Medicine, 20th Edition, vol. 2, pp. 2050-2057, 1996.*
Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*

(Continued)

*Primary Examiner* — Patricia L Morris
(74) *Attorney, Agent, or Firm* — Ice Miller LLP

(57) ABSTRACT

A heteroaryl[4,3-c]pyrimidin-5-amine derivative, a preparation method therefor, and medical uses thereof are provided. Specifically, a heteroaryl[4,3-c]pyrimidin-5-amine derivative of formula (I), a preparation method therefor, a pharmaceutical composition containing the derivative, and uses thereof as therapeutic agents are provided. In particular, the provided compounds can be used as $A_{2a}$ receptor antagonists and for treatment of conditions or symptoms that are ameliorated by inhibiting the $A_{2a}$ receptor. The various substituent groups in the formula (I) have the meanings as described in the specification.

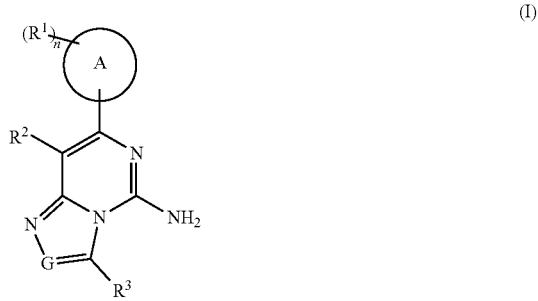

16 Claims, No Drawings

(56) References Cited

FOREIGN PATENT DOCUMENTS

| | | |
|---|---|---|
| WO | 2011143426 A1 | 11/2011 |
| WO | 2011159302 A1 | 12/2011 |
| WO | 2012037410 A2 | 3/2012 |
| WO | 2012056372 A1 | 5/2012 |
| WO | 2014101373 A1 | 7/2014 |
| WO | 2014162039 A1 | 10/2014 |
| WO | 2015031221 A1 | 3/2015 |

OTHER PUBLICATIONS

Acute Leukemia, Merck Manual (Online Edition) 6 pages, pp. 1-6 (2013).*
Schwarzschild et al, "Targeting adenosine A2A receptors in Parkinson's disease," TRENDS in Neurosciences, vol. 29, No. 11, pp. 647-654 (2006).
Press et al, "Therapeutic potential of adenosine receptor antagonists and agonists," Expert Opinion on Therapeutic Patents, vol. 17, No. 8, pp. 979-991 (2007).
Brooks et al, "An Open-Label, Positron Emission Tomography Study to Assess Adenosine A2A Brain Receptor Occupancy of Vipadenant (BIIB014) at Steady-State Levels in Healthy Male Volunteers," Clinical Neuropharmacology, vol. 33, No. 2, pp. 55-60 (2010).
Black et al, "Quantification of Indirect Pathway Inhibition by the Adenosine A2a Antagonist SYN115 in Parkinson Disease," The Journal of Neuroscience, vol. 30, No. 48, pp. 16284-16292 (2010).
Factor et al, "A long-term study of istradefylline in subjects with fluctuating Parkinson's disease," Parkinsonism and Related Disorders, vol. 16, No. 6, pp. 423-426 (2010).
Papapetropoulos et al, "The adenosine A2A receptor antagonist BIIB014 is effective in improving ON-time in Parkinson's disease (PD) patients with motor fluctuations," Journal of Movement Disorders, vol. 25, No. 2, p. S305 (2010).
Jenner, "Pathophysiology and biochemistry of dyskinesia: clues for the development of non-dopaminergic treatments," Journal of Neurology, vol. 247, Suppl. 2, pp. 1143-1150 (2000).
Lokshin et al, "Adenosine-Mediated Inhibition of the Cytotoxic Activity and Cytokine Production by Activated Natural Killer Cells," Cancer Research, vol. 66, No. 15, pp. 7758-7765 (2006).
Zong et al, "Progress in research on effects of adenosine A1 receptors," Chinese Pharmacological Bulletin, vol. 24, No. 5, pp. 573-576 (2008).
Maximino et al, "Adenosine A1, but not A2, Receptor Blockade Increases Anxiety and Arousal in Zebrafish," Basic & Clinical Pharmacology & Toxicology, vol. 109, No. 3, pp. 203-207 (2011).
Gessi et al, "The A3 adenosine receptor: An enigmatic player in cell biology," Pharmacology & Therapeutics, vol. 117, No. 1, pp. 123-140 (2008).
Harris et al, "Potent and selective adenosine A2A receptor antagonists: [1,2,4]-triazolo[4,3-c]pyrimidin-3-ones," Bioorganic & Medicinal Chemistry Letters, vol. 21, No. 8, pp. 2497-2501 (2011).

Congreve et al, "Discovery of 1,2,4-Triazine Derivatives as Adenosine A2A Antagonists using Structure Based Drug Design," Journal of Medicinal Chemistry, vol. 55, No. 5, pp. 1898-1903 (2012).
Larsen et al., "Iridium-Catalyzed C-H Borylation of Heteroarenes: Scope, Regioselectivity, Application to Late-Stage Functionalization, and Mechanism," Journal of the Amercian Chemical Society, vol. 136, No. 11, pp. 4287-4299 (2014).
Nagashima et al, "Design, Generation, and Synthetic Application of Borylzincate: Borylation of Aryl Halides and Borylzincation of Benzynes/Terminal Alkyne," Journal of the Amercian Chemical Society, vol. 135, No. 50, pp. 18730-18733 (2013).
Ishiyama et al, "Iridium-Catalyzed C-H Borylation of Arenes and Heteroarenes: 1-Chloro-3-iodo-5-(4,4,5,5-tetramethyl-1,3,2-dioxaborolan-2-yl)benzene and 2-(4,4,5,5,-Tetramethyl-1,3,2-dioxaborolan-2-yl)indole," Organic Syntheses, vol. 82, pp. 126-133 (2005).
Wang et al, "Rhodium(III)-Catalyzed Intermolecular Amidation with Azides via C(sp3)-H Functionalization," The Journal of Organic Chemistry, vol. 79, No. 11, pp. 5379-5385 (2014).
Childers et al, "The Synthesis and Biological Evaluation of Quinolyl-piperazinyl Piperidines as Potent Serotonin 5-HT1A Antagonists," Journal of Medicinal Chemistry, vol. 53, No. 10, pp. 4066-4084 (2010).
Schaefer et al, "Evaluation of Cobalt Complexes Bearing Tridentate Pincer Ligands for Catalytic C-H Borylation," Organometallics, vol. 34, No. 7, pp. 1307-1320 (2015).
Currie et al, "Discovery of GS-9973, a Selective and Orally Efficacious Inhibitor of Spleen Tyrosine Kinase," Journal of Medicinal Chemistry, vol. 57, No. 9, pp. 3856-3873 (2014).
Harrisson et al, "Microwave-Accelerated Iridium-Catalyzed Borylation of Aromatic C-H Bonds," Organic Letters, vol. 11, No. 16, pp. 3586-3589 (2009).
Obligacion et al, "Cobalt-Catalyzed C-H Borylation," Journal of the American Chemical Society, vol. 136, No. 11, pp. 4133-4136 (2014).
Sekiya et al, "Pyrimidine Derivatives II—New Synthesis and Reactions of 4-Amino-2-methyliopyrimidine Derivatives," Chemical & Pharmaceutical Bulletin, vol. 29, No. 4, pp. 948-954 (1981).
Plé et al, "Metalation of Diazines X—First Halogen Migration during Metalation of Pyrimidines Unusual Halogen-Lithium Exchange with LTMP New Synthesis of Leshmaniacides," Tetrahedron, vol. 50, No. 34, p. 10299-10308 (1994).
Zeqing et al, "Microwave-assisted, Ir-catalyzed aromatic C-H borylation," Research on Chemical Intermediates, vol. 39, No. 4, pp. 1917-1926 (2013).
Ren et al, "Cobalt-Catalyzed Regioselective Borylation of Arenes: N-Heterocyclic Silylene as an Electron Donor in the Metal-Mediated Activation of C-H Bonds," Chemistry—A European Journal, vol. 23, No. 24, pp. 5663-5667 (2017).
Int'l Search Report dated May 16, 2018 in Int'l Application No. PCT/CN2018/079086.
Examination Report dated Apr. 21, 2021 in corresponding Australian application No. 2018233367.

* cited by examiner

HETEROARYL[4,3-C]PYRIMIDINE-5-AMINE DERIVATIVE, PREPARATION METHOD THEREFOR, AND MEDICAL USES THEREOF

CROSS-REFERENCE TO RELATED APPLICATIONS

This application is a Section 371 of International Application No. PCT/CN2018/079086, filed Mar. 15, 2018, which was published in the Chinese language on Sep. 20, 2018 under International Publication No. WO 2018/166493 A1, which claims priority under 35 U.S.C. § 119(b) to Chinese Application No. 201710156742.7, filed Mar. 16, 2017, and Chinese Application No. 201710982734.8, filed Oct. 20, 2017, and the disclosures of which are incorporated herein by reference.

FIELD OF THE INVENTION

The present invention belongs to the field of medicine, and relates to a heteroaryl[4,3-c]pyrimidine-5-amine derivative of formula (I), a method for preparing the same, a pharmaceutical composition comprising the same, a use thereof as a therapeutic agent, in particular as an $A_{2a}$ receptor antagonist, and a use thereof in the preparation of a medicament for treating a disease or condition ameliorated by the inhibition of the $A_{2a}$ receptor.

BACKGROUND OF THE INVENTION

Adenosine is a naturally occurring purine nucleoside, and is an endogenous regulator of many physiological functions. It plays an important role in the regulation of the cardiovascular system, central nervous system, respiratory system, kidney, fat and platelets.

The action of adenosine is mediated by a family of G-protein coupled receptors. It is known currently that there are at least four subtypes of adenosine receptors, which are classified into $A_1$, $A_{2a}$, $A_{2b}$ and $A_3$. Among them, the $A_1$ and $A_3$ receptors inhibit the activity of the enzyme adenylate cyclase, whereas the $A_{2a}$ and $A_{2b}$ receptors stimulate the activity of the same enzyme, thereby modulating the level of cyclic AMP in cells. Adenosine regulates a wide range of physiological functions through these receptors.

The $A_{2a}$ receptor ($A_{2a}R$) is widely distributed in the body, and is mainly expressed in the striatum in the central nervous system, and is also expressed in tissues such as the periphery, heart, liver, lung and kidney. Several preclinical studies show that adenosine $A_{2a}$ receptor antagonists have surprising efficacy in the treatment of neurodegenerative diseases, primarily Parkinson's disease, Huntington's disease or Alzheimer's disease (*Trends in Neurosci.* 2006, 29(11), 647-654; Expert Opinion on Therapeutic Patents, 2007, 17, 979-991 and the like). Moreover, adenosine $A_{2a}$ receptor antagonists can also be used to treat other central nervous system (CNS) related diseases such as depression, restless syndrome, sleep disorders and anxiety disorders (*Clin. Neuropharmacol.* 2010, 33, 55-60; *J. Neurosci.* 2010, 30 (48), 16284-16292; *Parkinsonisn Relat. Disord.* 2010, 16 (6), 423-426; and references therein: *Mov. Disorders*, 2010, 25(2), S305). In addition, adenosine $A_{2a}$ receptor antagonists also have therapeutic potential as neuroprotective agents (see Jenner P. *J Neuro* 1. 2000; 24 7 Supp 12: 1143-50).

Recent studies indicate that the activation of the adenosine $A_{2a}$ receptor can exert an important immunomodulatory effect in many pathological processes such as ischemia, hypoxia, inflammation, trauma, transplantation and the like, which may be related to the higher expression level of the $A_{2a}$ receptor in various immune cells such as T cells, B cells, monocyte macrophages, neutrophils and the like. Moreover, the activation of the $A_{2a}$ receptor can promote the body to generate immune tolerance, and closely participate in the formation of "immune escape" or "immunosuppression" of tumor cells, thereby creating a favorable condition for the occurrence and development of tumors. Lokshin and his colleagues (*Cancer Res.* 2006, Aug. 1; 66(15):7758-65) demonstrate that the activation of $A_{2a}R$ in natural killer cells can inhibit the killing of tumor cells by natural killer cells through increasing cAMP and activating PKA. Studies also show that the activation of $A_{2a}$ receptor can promote the proliferation of tumor cells such as melanoma A375 cells, fibroblast NIH3T3 cells, pheochromocytoma PC12 cells and the like, which may be related to the fact that the activation of the $A_{2a}$ receptor in T cells can inhibit T cell activation, proliferation, adhesion to tumor cells, and produce cytotoxic effects on tumor cells. However, in $A_{2a}$ receptor knockout mice, the anti-tumor immunity of $CD8^+$ T cells is enhanced, and tumor proliferation is significantly inhibited. Therefore, $A_{2a}$ receptor antagonists can also be used in the treatment of tumor.

Although compounds having significant biological activity on a variety of subtypes of adenosine receptors can have a therapeutic effect, they can cause undesired side effects. For example, during tissue ischemia/hypoxia, when cells of the central system, circulatory system, digestive system and skeletal muscle are in an anoxic and hypoxic stress environment, extracellular aggregated adenosine initiates a corresponding protective mechanism by activating the adenosine $A_1$ receptor on the cell membrane, thereby increasing the tolerance of the cells to anoxia and hypoxia. The $A_1$ receptor located on immune cells can promote cellular immune responses in a hypoxic environment. Moreover, the $A_1$ receptor can also reduce free fatty acids and triglycerides, and is involved in regulating blood glucose. Therefore, the continued blocking of the $A_1$ receptor can cause various adverse effects in the body tissues (*Chinese Pharmacological Bulletin*, 2008, 24(5), 573-576). For example, it is reported that the blocking of the $A_1$ receptor can cause adverse effects such as anxiety, awakening and the like in animal models (*Basic & Clinical Pharmacology & Toxicology*, 2011, 109(3), 203-7). The adenosine released by the adenosine $A_3$ receptor during myocardial ischemia exerts a strong protective effect in the heart (as described by Gessi S et al, *Pharmacol. Ther.* 117 (1), 2008, 123-140). The continued blocking of the $A_3$ receptor can increase the likelihood of complications caused by any pre-existing or developing ischemic heart disease such as angina or heart failure.

Currently, many compounds have been developed as $A_{2a}$ receptor antagonists for the treatment of various diseases, as described in WO2007116106, WO2009080197, WO2011159302, WO2011095625, WO2014101373 and WO2015031221. However, there still exist problems such as low solubility, photosensitivity, low activity, low selectivity and low bioavailability.

The present invention provides a novel heteroaryl[4,3-c] pyrimidine-5-amine structure as an adenosine $A_{2a}$ receptor antagonist, and finds that the compounds having such a structure have a potent inhibition activity, high selectivity, low concentration of free drug in the brain, weak ability to pass the blood-brain barrier, and less side effects that are likely generated after the drug enters the brain.

SUMMARY OF THE INVENTION

The object of the present invention is to provide a compound of formula (I):

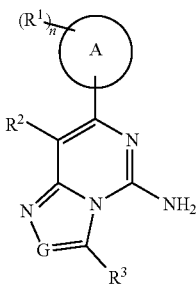

(I)

or a tautomer, mesomer, racemate, enantiomer, diastereomer thereof, or mixture thereof, or a pharmaceutically acceptable salt thereof, wherein:

G is N or $CR^4$;

ring A is selected from the group consisting of cycloalkyl, aryl and heteroaryl;

each $R^1$ is identical or different and each is independently selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl;

$R^2$ is selected from the group consisting of alkoxy, hydroxy, cyano, amino, nitro, cycloalkyl, heterocyclyl, aryl and heteroaryl, wherein the alkoxy, cycloalkyl, heterocyclyl, aryl and heteroaryl are each independently optionally substituted by one or more substituents selected from the group consisting of halogen, alkyl, alkoxy, haloalkyl, hydroxy, hydroxyalkyl, oxo, cyano, amino, nitro, cycloalkyl, heterocyclyl, aryl, heteroaryl, $C(O)OR^5$ and $R^b$;

$R^3$ is selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl;

$R^4$ is selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl;

$R^5$ is selected from the group consisting of hydrogen, alkyl, amino, haloalkyl, cycloalkyl, heterocyclyl, aryl and heteroaryl;

$R^b$ is heterocyclylalkyl, wherein the heterocyclyl of the heterocyclylalkyl is optionally substituted by one or more substituents selected from the group consisting of alkoxy, hydroxy, hydroxyalkyl, cyano, amino, nitro, cycloalkyl, cycloalkyloxy, heterocyclyl, aryl, heteroaryl and $C(O)OR^5$; and n is 1, 2, 3 or 4.

In a preferred embodiment of the present invention, in the compound of formula (I), $R^2$ is selected from the group consisting of cyano, cycloalkyl, heterocyclyl, aryl and heteroaryl, wherein the cycloalkyl, heterocyclyl, aryl and heteroaryl are each independently optionally substituted by one or more substituents selected from the group consisting of halogen, alkyl, haloalkyl, alkoxy, oxo, cycloalkyl, heterocyclyl and $R^b$; $R^b$ is heterocyclylalkyl, wherein the heterocyclyl of the heterocyclylalkyl is optionally substituted by one or more alkyl.

In a preferred embodiment of the present invention, the compound of formula (I) is a compound of formula (II):

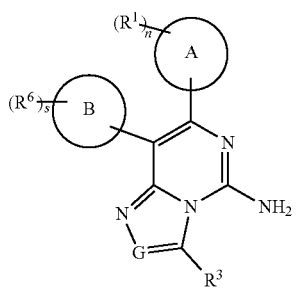

(II)

or a tautomer, mesomer, racemate, enantiomer, diastereomer thereof, or mixture thereof, or a pharmaceutically acceptable salt thereof, wherein:

ring B is selected from the group consisting of cycloalkyl, heterocyclyl, aryl and heteroaryl;

each $R^6$ is identical or different and each is independently selected from the group consisting of hydrogen, halogen, alkyl, alkoxy, haloalkyl, hydroxy, hydroxyalkyl, oxo, cyano, amino, nitro, cycloalkyl, heterocyclyl, aryl, heteroaryl, $C(O)OR^5$ and $R^b$;

s is 0, 1, 2, 3 or 4; and ring A, G, $R^1$, $R^3$, $R^5$, $R^b$ and n are as defined in formula (I).

In a preferred embodiment of the present invention, the compound of formula (I) is a compound of formula (III):

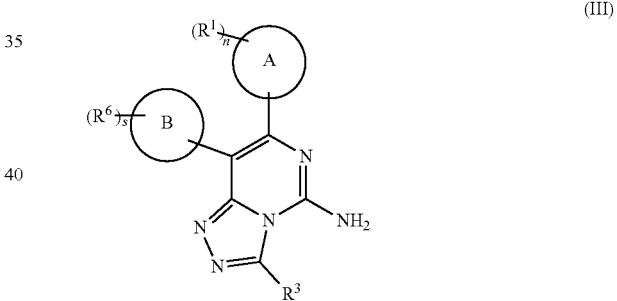

(III)

or a tautomer, mesomer, racemate, enantiomer, diastereomer thereof, or mixture thereof, or a pharmaceutically acceptable salt thereof, wherein:

each $R^6$ is identical or different and each is independently selected from the group consisting of halogen, alkyl, haloalkyl, alkoxy, oxo, cycloalkyl, heterocyclyl and $R^b$; $R^b$ is heterocyclylalkyl, wherein the heterocyclyl of the heterocyclylalkyl is optionally substituted by one or more alkyl;

ring A, ring B, $R^1$, $R^3$, n and s are as defined in formula (II).

In a preferred embodiment of the present invention, in the compound of formula (II), ring B is selected from the group consisting of phenyl, 5 to 6 membered heterocyclyl and 5 to 10 membered heteroaryl, and preferably phenyl, pyridyl, pyrazolyl, pyridin-2-one, imidazolyl, pyrrolyl, furyl, thienyl, piperidinyl, 1,2,3,6-tetrahydropyridyl, isoquinolyl, quinolyl, quinoxalinyl, indolyl, indazolyl, benzofuranyl and benzothienyl.

In a preferred embodiment of the present invention, the compound of formula (I) is a compound of formula (III'):

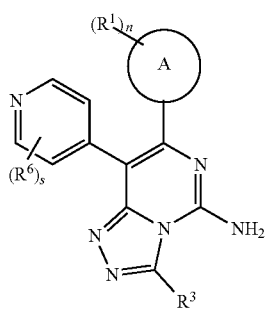

(III')

or a tautomer, mesomer, racemate, enantiomer, diastereomer thereof, or mixture thereof, or a pharmaceutically acceptable salt thereof, wherein:

each $R^6$ is identical or different and each is independently selected from the group consisting of hydrogen, halogen, alkyl, haloalkyl, alkoxy, oxo, cycloalkyl, heterocyclyl and $R^b$; $R^b$ is heterocyclylalkyl, wherein the heterocyclyl of the heterocyclylalkyl is optionally substituted by one or more alkyl;

s is 0, 1, 2, 3 or 4; ring A, $R^1$, $R^3$ and n are as defined in formula (I).

In a preferred embodiment of the present invention, in the compound of formula (I), ring A is aryl or heteroaryl, and preferably phenyl or furyl.

In a preferred embodiment of the present invention, in the compound of formula (I), $R^1$ is selected from the group consisting of hydrogen, halogen and alkyl.

In a preferred embodiment of the present invention, in the compound of formula (I), $R^3$ is selected from the group consisting of hydrogen, halogen and alkyl.

Typical compounds of the present invention include, but are not limited to:

| Example No. | Structure and name of the compound |
|---|---|
| 1 | 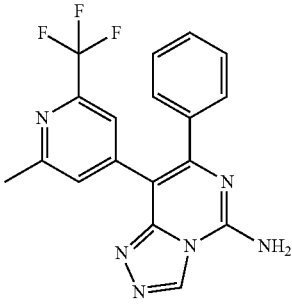<br>8-(2-Methyl-6-(trifluoromethyl)pyridin-4-yl)-7-phenyl-[1,2,4]triazolo[4,3-c]pyrimidin-5-amine<br>1 |
| 2 | 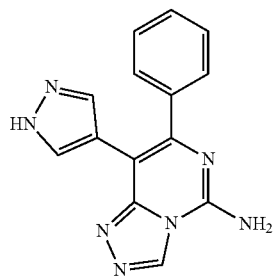<br>7-Phenyl-8-(1H-pyrazol-4-yl)-[1,2,4]triazolo[4,3-c]pyrimidin-5-amine<br>2 |
| 3 | 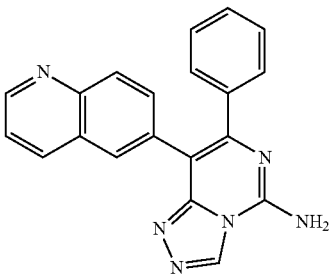<br>7-Phenyl-8-(quinolin-6-yl)-[1,2,4]triazolo[4,3-c]pyrimidin-5-amine<br>3 |
| 4 | 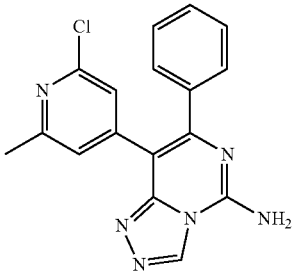<br>8-(2-Chloro-6-methylpyridin-4-yl)-7-phenyl-[1,2,4]triazolo[4,3-c]pyrimidin-5-amine<br>4 |

-continued

| Example No. | Structure and name of the compound |
|---|---|
| 5 | 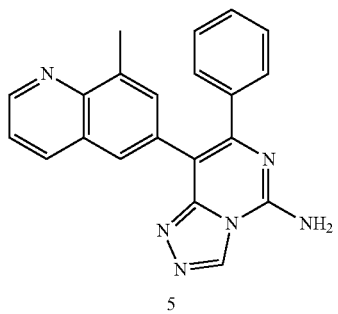 [SMILES: Cc1cc(-c2c(-c3ccccc3)nc(N)n3cnnc23)cc2cccnc12]<br>8-(8-Methylquinolin-6-yl)-7-phenyl-[1,2,4]triazolo[4,3-c]pyrimidin-5-amine<br>5 |
| 6 | 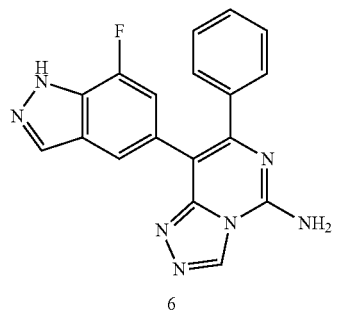 [SMILES: Nc1nc(-c2ccccc2)c(-c2cc(F)c3[nH]ncc3c2)c2nncn12]<br>8-(7-Fluoro-1H-indazol-5-yl)-7-phenyl-[1,2,4]triazolo[4,3-c]pyrimidin-5-amine<br>6 |
| 7 | 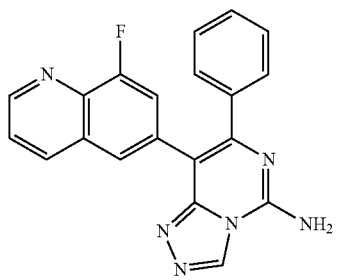<br>8-(8-Fluoroquinolin-6-yl)-7-phenyl-[1,2,4]triazolo[4,3-c]pyrimidin-5-amine<br>7 |

-continued

| Example No. | Structure and name of the compound |
|---|---|
| 8 | 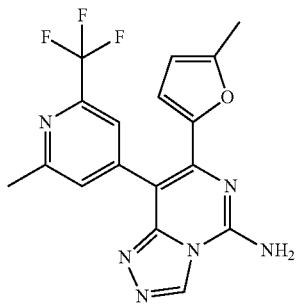<br>8-(2-Methyl-6-(trifluoromethyl)pyridin-4-yl)-7-(5-methyl-furan-2-yl)-[1,2,4]triazolo[4,3-c]pyrimidin-5-amine<br>8 |
| 9 | 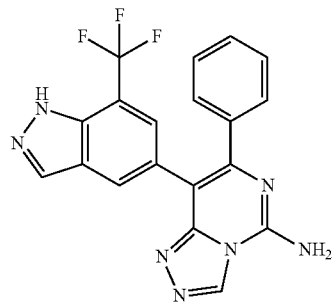<br>7-Phenyl-8-(7-(trifluoromethyl)-1H-indazol-5-yl)-[1,2,4]triazolo[4,3-c]pyrimidin-5-amine<br>9 |
| 10 | 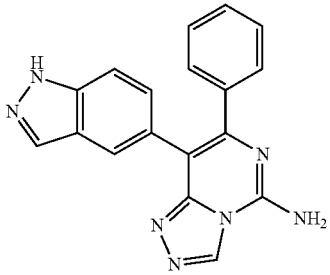<br>8-(1H-indazol-5-yl)-7-phenyl-[1,2,4]triazolo[4,3-c]pyrimidin-5-amine<br>10 |

-continued

| Example No. | Structure and name of the compound |
|---|---|
| 11 | 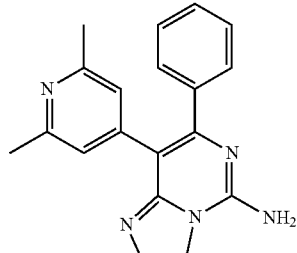

8-(2,6-Dimethylpyridin-4-yl)-7-phenyl-[1,2,4]
triazolo[4,3-c]pyrimidin-5-amine
11 |
| 12 | 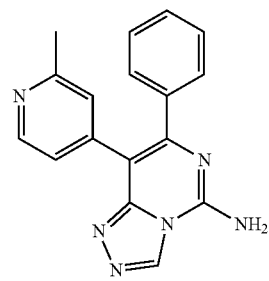

8-(2-Methylpyridin-4-yl)-7-phenyl-[1,2,4]
triazolo[4,3-c]pyrimidin-5-amine
12 |
| 13 | 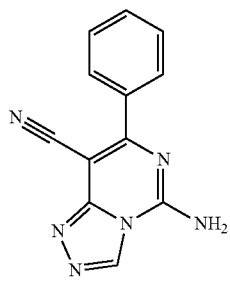

5-Amino-7-phenyl-[1,2,4]triazolo[4,3-c]
pyrimidine-8-carbonitrile
13 |

-continued

| Example No. | Structure and name of the compound |
|---|---|
| 14 | 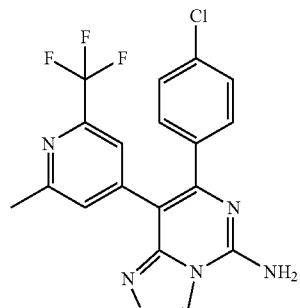

7-(4-Chlorophenyl)-8-(2-methyl-6-(trifluoromethyl)pyridin-
4-yl)-[1,2,4]triazolo[4,3-c]pyrimidin-5-amine
14 |
| 15 | 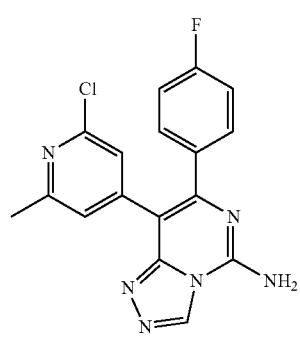

8-(2-Chloro-6-methylpyridin-4-yl)-7-(4-fluorophenyl)-
[1,2,4]triazolo[4,3-c]pyrimidin-5-amine
15 |
| 16 | 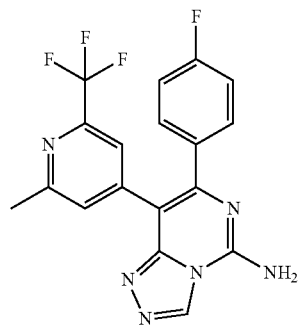

7-(4-Fluorophenyl)-8-(2-methyl-6-(trifluoromethyl)pyridin-
4-yl)-[1,2,4]triazolo[4,3-c]pyrimidin-5-amine
16 |

| Example No. | Structure and name of the compound |
|---|---|
| 17 | 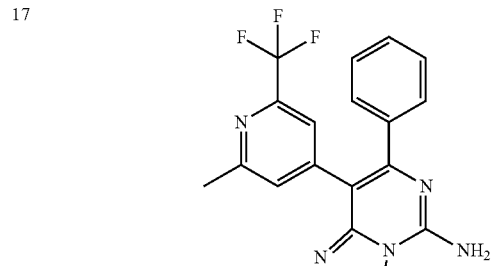<br>8-(2-Methyl-6-(trifluoromethyl)pyridin-4-yl)-7-phenylimidazo[1,2-c]pyrimidin-5-amine<br>17 |
| 18 | 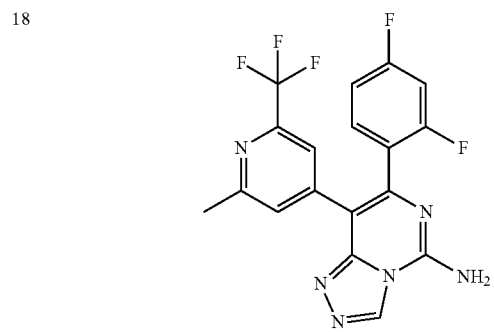<br>7-(2,4-Difluorophenyl)-8-(2-methyl-6-(trifluoromethyl)pyridin-4-yl)-[1,2,4]triazolo[4,3-c]pyrimidin-5-amine<br>18 |
| 19 | 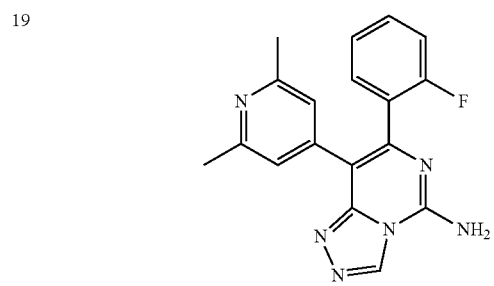<br>8-(2,6-Dimethylpyridin-4-yl)-7-(2-fluorophenyl)-[1,2,4]triazolo[4,3-c]pyrimidin-5-amine<br>19 |
| 20 | 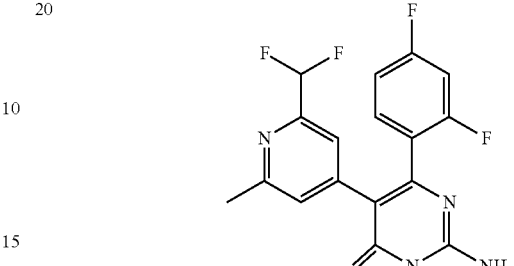<br>8-(2-(Difluoromethyl)-6-methylpyridin-4-yl)-7-(2,4-difluorophenyl)-[1,2,4]triazolo[4,3-c]pyrimidin-5-amine<br>20 |
| 21 | 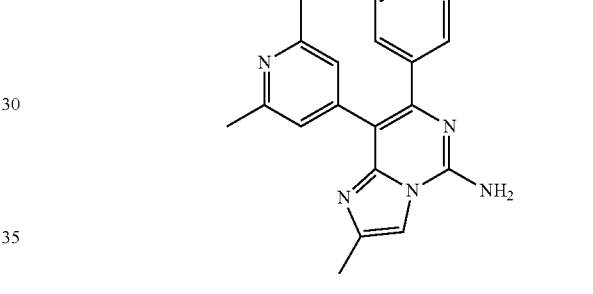<br>8-(2,6-Dimethylpyridin-4-yl)-2-methyl-7-phenylimidazo[1,2-c]pyrimidin-5-amine<br>21 |
| 22 | 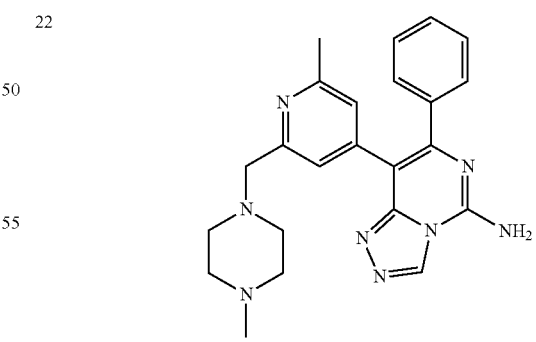<br>8-(2-Methyl-6-((4-methylpiperazin-1-yl)methyl)pyridin-4-yl)-7-phenyl-[1,2,4]triazolo[4,3-c]pyrimidin-5-amine<br>22 |

-continued

| Example No. | Structure and name of the compound |
|---|---|
| 23 | 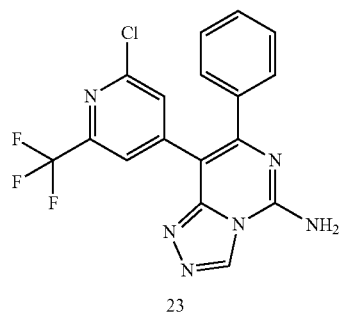 [SMILES: Nc1nc(-c2ccccc2)c(-c2cc(Cl)nc(C(F)(F)F)c2)c2nncn12]<br>8-(2-Chloro-6-(trifluoromethyl)pyridin-4-yl)-7-phenyl-[1,2,4]triazolo[4,3-c]pyrimidin-5-amine<br>23 |
| 24 | 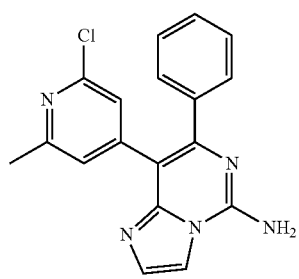<br>8-(2-Chloro-6-methylpyridin-4-yl)-7-phenylimidazo[1,2-c]pyrimidin-5-amine<br>24 |
| 25 | 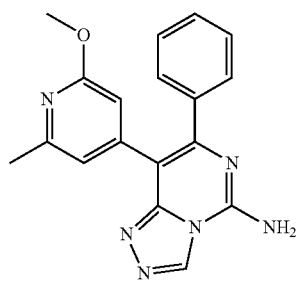<br>8-(2-Methoxy-6-methylpyridin-4-yl)-7-phenyl-[1,2,4]triazolo[4,3-c]pyrimidin-5-amine<br>25 |

-continued

| Example No. | Structure and name of the compound |
|---|---|
| 26 | 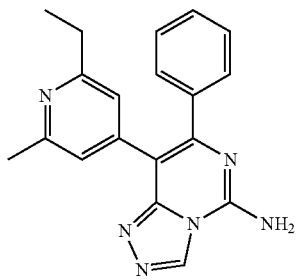<br>8-(2-Ethyl-6-methylpyridin-4-yl)-7-phenyl-[1,2,4]triazolo[4,3-c]pyrimidin-5-amine<br>26 |
| 27 | 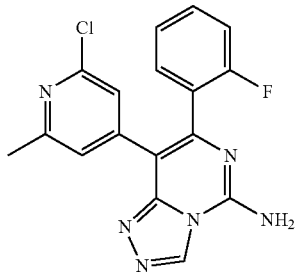<br>8-(2-Chloro-6-methylpyridin-4-yl)-7-(2-fluorophenyl)-[1,2,4]triazolo[4,3-c]pyrimidin-5-amine<br>27 |
| 28 | 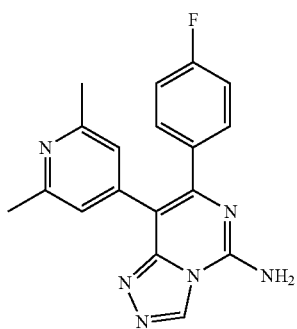<br>8-(2,6-Dimethylpyridin-4-yl)-7-(4-fluorophenyl)-[1,2,4]triazolo[4,3-c]pyrimidin-5-amine<br>28 |

| Example No. | Structure and name of the compound |
|---|---|
| 29 | 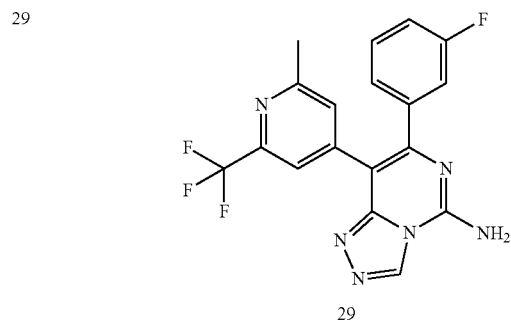

7-(3-Fluorophenyl)-8-(2-methyl-6-(trifluoromethyl)pyridin-4-yl)-[1,2,4]triazolo[4,3-c]pyrimidin-5-amine
29 |
| 30 | 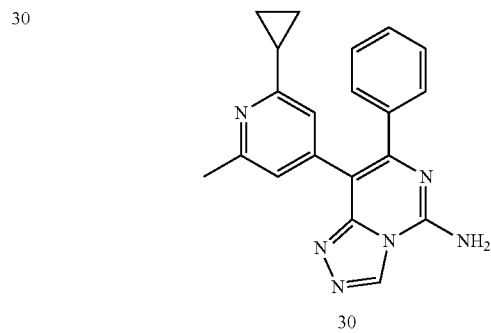

8-(2-Cyclopropyl-6-methylpyridin-4-yl)-7-phenyl-[1,2,4]triazolo[4,3-c]pyrimidin-5-amine
30 |
| 31 | 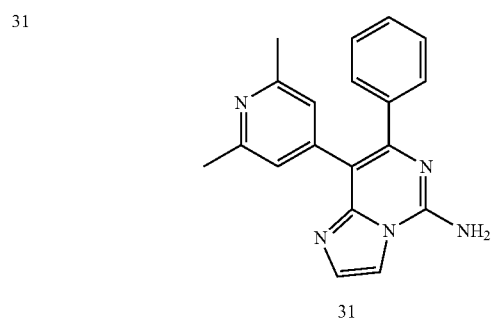

8-(2,6-Dimethylpyridin-4-yl)-7-phenylimidazo[1,2-c]pyrimidin-5-amine
31 |
| 32 | 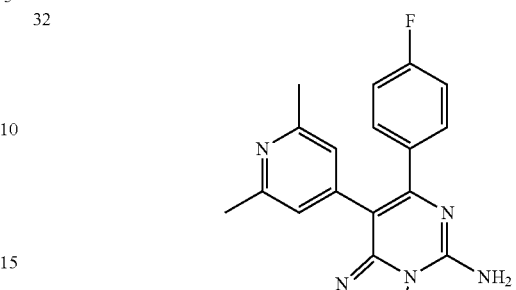

8-(2,6-Dimethylpyridin-4-yl)-7-(4-fluorophenyl)imidazo[1,2-c]pyrimidin-5-amine
32 |
| 33 | 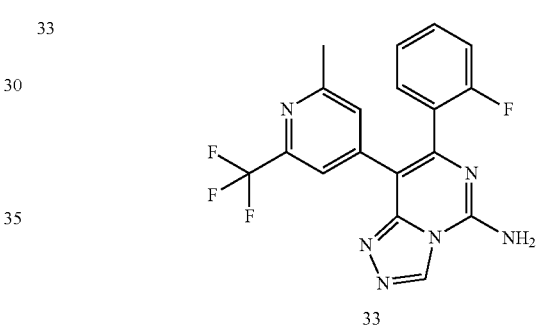

7-(2-Fluorophenyl)-8-(2-methyl-6-(trifluoromethyl)pyridin-4-yl)-[1,2,4]triazolo[4,3-c]pyrimidin-5-amine
33 |
| 34 | 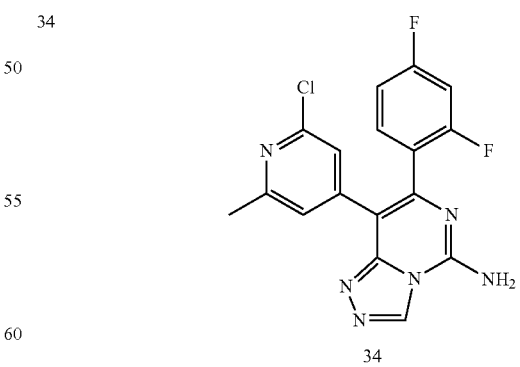

8-(2-Chloro-6-methylpyridin-4-yl)-7-(2,4-difluorophenyl)-[1,2,4]triazolo[4,3-c]pyrimidin-5-amine
34 |

| Example No. | Structure and name of the compound |
|---|---|
| 35 | 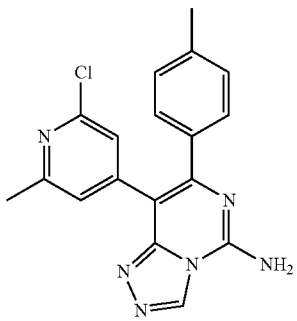<br>8-(2-Chloro-6-methylpyridin-4-yl)-7-(p-tolyl)-[1,2,4]triazolo[4,3-c]pyrimidin-5-amine<br>35 |
| 36 | 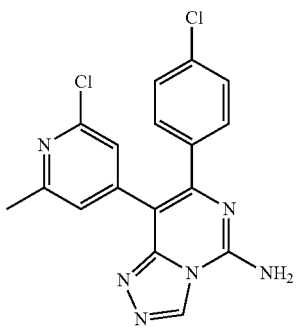<br>8-(2-Chloro-6-methylpyridin-4-yl)-7-(4-chlorophenyl)-[1,2,4]triazolo[4,3-c]pyrimidin-5-amine<br>36 |
| 37 | 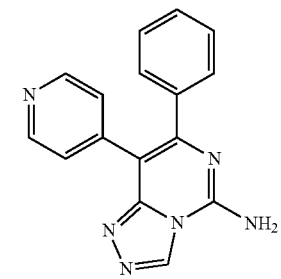<br>7-Phenyl-8-(pyridin-4-yl)-[1,2,4]triazolo[4,3-c]pyrimidin-5-amine<br>37 |
| 38 | 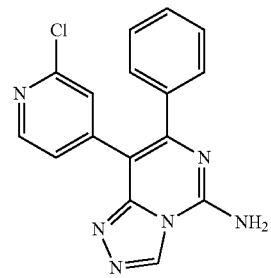<br>8-(2-Chloropyridin-4-yl)-7-phenyl-[1,2,4]triazolo[4,3-c]pyrimidin-5-amine<br>38 |
| 39 | 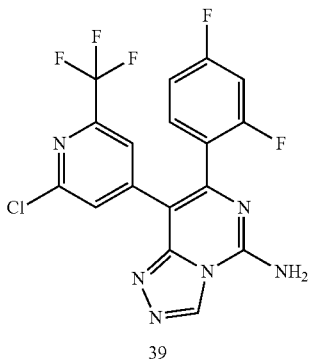 [SMILES: Nc1nc(-c2ccc(F)cc2F)c(-c2cc(Cl)nc(C(F)(F)F)c2)c2nncn12]<br>8-(2-Chloro-6-(trifluoromethyl)pyridin-4-yl)-7-(2,4-difluorophenyl)-[1,2,4]triazolo[4,3-c]pyrimidin-5-amine<br>39 |
| 40 | 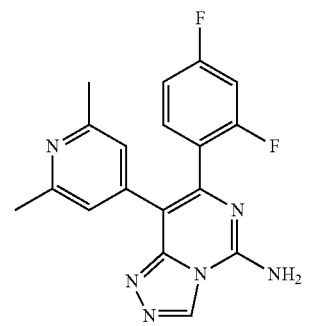<br>7-(2,4-Difluorophenyl)-8-(2,6-dimethylpyridin-4-yl)-[1,2,4]triazolo[4,3-c]pyrimidin-5-amine<br>40 |

| Example No. | Structure and name of the compound |
|---|---|
| 41 | 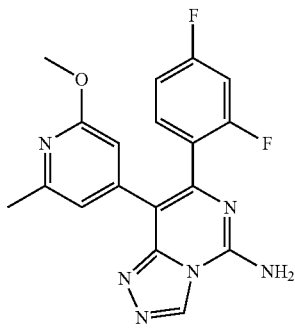<br>7-(2,4-Difluorophenyl)-8-(2-methoxy-6-methylpyridin-4-yl)-[1,2,4]triazolo[4,3-c]pyrimidin-5-amine<br>41 |
| 42 | 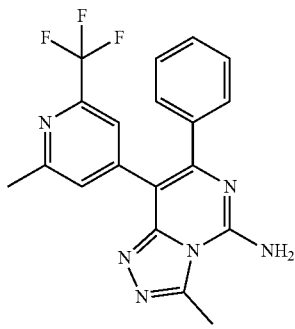<br>3-Methyl-8-(2-methyl-6-(trifluoromethyl)pyridin-4-yl)-7-phenyl-[1,2,4]triazolo[4,3-c]pyrimidin-5-amine<br>42 |
| 43 | 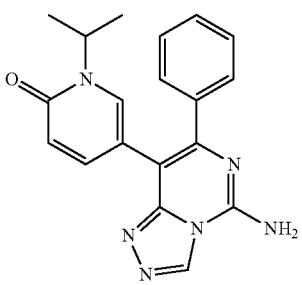<br>5-(5-Amino-7-phenyl-[1,2,4]triazolo[4,3-c]pyrimidin-8-yl)-1-isopropylpyridin-2(1H)-one<br>43 |
| 44 | 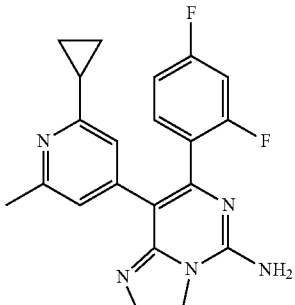<br>8-(2-Cyclopropyl-6-methylpyridin-4-yl)-7-(2,4-difluorophenyl)-[1,2,4]triazolo[4,3-c]pyrimidin-5-amine<br>44 |
| 45 | 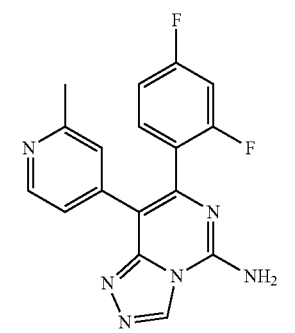<br>7-(2,4-Difluorophenyl)-8-(2-methylpyridin-4-yl)-[1,2,4]triazolo[4,3-c]pyrimidin-5-amine<br>45 |
| 46 | 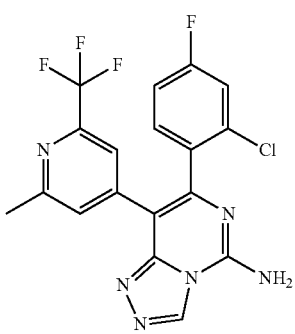<br>7-(2-Chloro-4-fluorophenyl)-8-(2-methyl-6-(trifluoromethyl)pyridin-4-yl)-[1,2,4]triazolo[4,3-c]pyrimidin-5-amine<br>46 |

-continued

| Example No. | Structure and name of the compound |
|---|---|
| 47 | 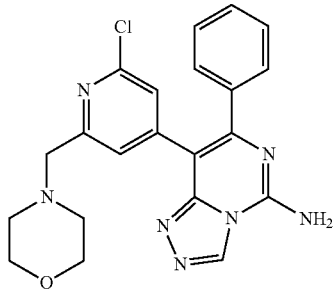<br>47<br>8-(2-Chloro-6-(morpholinomethyl)pyridin-4-yl)-7-phenyl-[1,2,4]triazolo[4,3-c]pyrimidin-5-amine<br>47 |
| 48 | 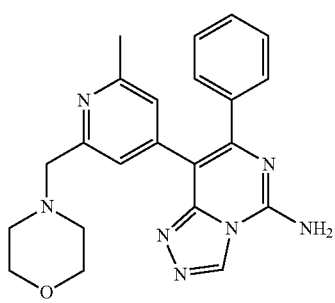<br>48<br>8-(2-Methyl-6-(morpholinomethyl)pyridin-4-yl)-7-phenyl-[1,2,4]triazolo[4,3-c]pyrimidin-5-amine<br>48 |
| 49 | 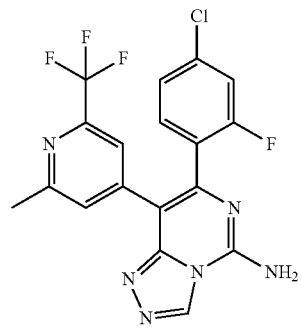<br>49<br>7-(4-Chloro-2-fluorophenyl)-8-(2-methyl-6-(trifluoromethyl)pyridin-4-yl)-[1,2,4]triazolo[4,3-c]pyrimidin-5-amine<br>49 |

-continued

| Example No. | Structure and name of the compound |
|---|---|
| 50 | 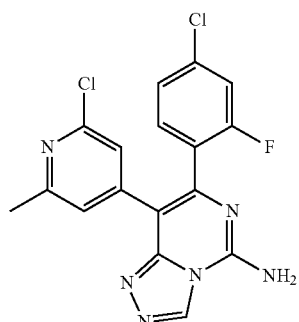<br>50<br>7-(4-Chloro-2-fluorophenyl)-8-(2-chloro-6-methylpyridin-4-yl)-[1,2,4]triazolo[4,3-c]pyrimidin-5-amine<br>50 |
| 51 | 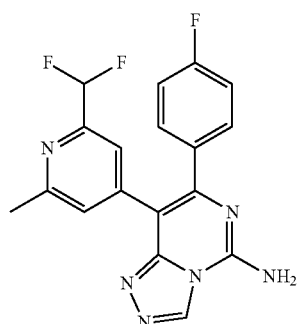<br>51<br>8-(2-(Difluoromethyl)-6-methylpyridin-4-yl)-7-(4-fluorophenyl)-[1,2,4]triazolo[4,3-c]pyrimidin-5-amine<br>51 |
| 52 | 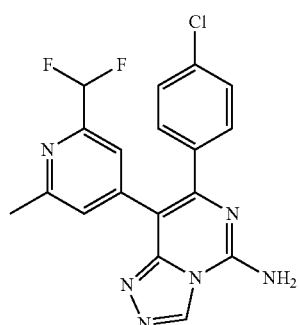<br>52<br>7-(4-Chlorophenyl)-8-(2-(difluoromethyl)-6-methylpyridin-4-yl)-[1,2,4]triazolo[4,3-c]pyrimidin-5-amine<br>52 |

| Example No. | Structure and name of the compound |
|---|---|
| 53 | 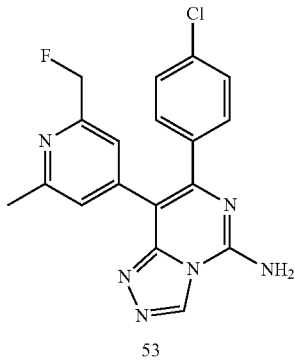 [SMILES: Cc1cc(-c2c(-c3ccc(Cl)cc3)nc(N)n3cnnc23)cc(CF)n1]

53

7-(4-Chlorophenyl)-8-(2-(fluoromethyl)-6-methylpyridin-4-yl)-[1,2,4]triazolo[4,3-c]pyrimidin-5-amine
53 |
| 54 | 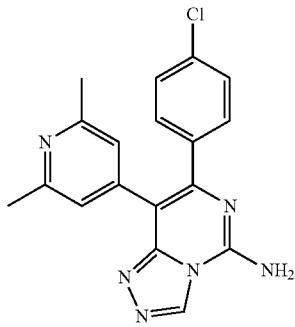

54

7-(4-Chlorophenyl)-8-(2,6-dimethylpyridin-4-yl)-[1,2,4]triazolo[4,3-c]pyrimidin-5-amine
54 |
| 55 | 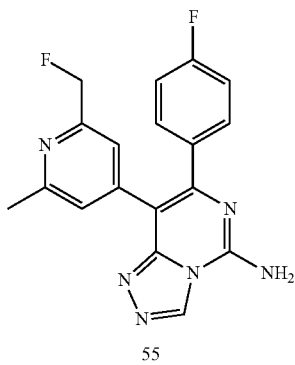 [SMILES: Cc1cc(-c2c(-c3ccc(F)cc3)nc(N)n3cnnc23)cc(CF)n1]

55

8-(2-(Fluoromethyl)-6-methylpyridin-4-yl)-7-(4-fluorophenyl)-[1,2,4]triazolo[4,3-c]pyrimidin-5-amine
55 |
| 56 | 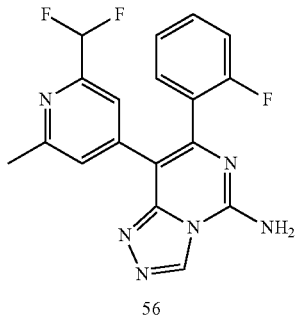 [SMILES: Cc1cc(-c2c(-c3ccccc3F)nc(N)n3cnnc23)cc(C(F)F)n1]

56

8-(2-(Difluoromethyl)-6-methylpyridin-4-yl)-7-(2-fluorophenyl)-[1,2,4]triazolo[4,3-c]pyrimidin-5-amine
56 |
| 57 | 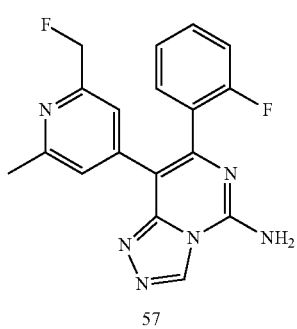 [SMILES: Cc1cc(-c2c(-c3ccccc3F)nc(N)n3cnnc23)cc(CF)n1]

57

8-(2-(Fluoromethyl)-6-methylpyridin-4-yl)-7-(2-fluorophenyl)-[1,2,4]triazolo[4,3-c]pyrimidin-5-amine
57 |
| 58 | 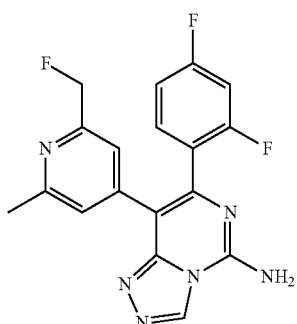

58

7-(2,4-Difluorophenyl)-8-(2-(fluoromethyl)-6-methylpyridin-4-yl)-[1,2,4]triazolo[4,3-c]pyrimidin-5-amine
58 |

| Example No. | Structure and name of the compound |
|---|---|
| 59 | 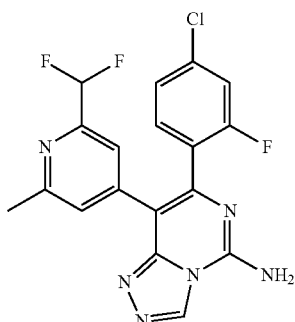<br>59<br>7-(4-Chloro-2-fluorophenyl)-8-(2-(difluoromethyl)-6-methylpyridin-4-yl)-[1,2,4]triazolo[4,3-c]pyrimidin-5-amine<br>59 | or a tautomer, mesomer, racemate, enantiomer, diastereomer thereof, or mixture thereof, or a pharmaceutically acceptable salt thereof.

In another aspect, the present invention relates to a compound of formula (IV):

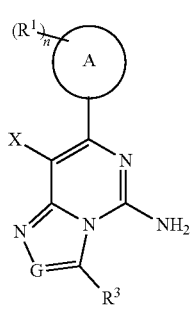

(IV)

or a tautomer, mesomer, racemate, enantiomer, diastereomer thereof, or mixture thereof, or a pharmaceutically acceptable salt thereof,
wherein:
X is a halogen;
ring A, G, $R^1$, $R^3$ and n are as defined in formula (I).

Typical compounds of the present invention include, but are not limited to:

| Example No. | Structure and name of the compound |
|---|---|
| 2c | 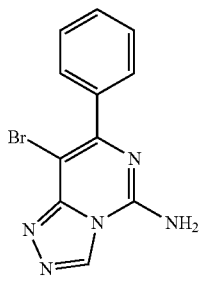<br>2c<br>8-Bromo-7-phenyl-[1,2,4]triazolo[4,3-c]pyrimidin-5-amine<br>2c |
| 8e | 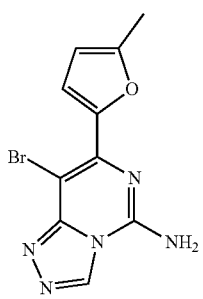<br>8e<br>8-Bromo-7-(5-methylfuran-2-yl)-[1,2,4]triazolo[4,3-c]pyrimidin-5-amine<br>8e |
| 14d | 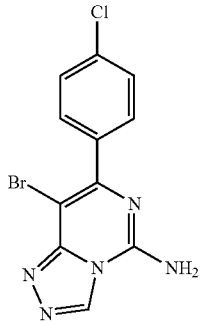<br>14d<br>8-Bromo-7-(4-chlorophenyl)-[1,2,4]triazolo[4,3-c]pyrimidin-5-amine<br>14d |

| Example No. | Structure and name of the compound |
|---|---|
| 15f | 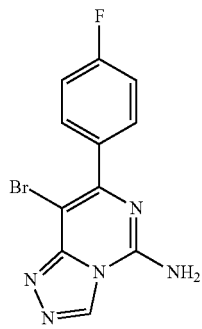

15f

8-Bromo-7-(4-fluorophenyl)-[1,2,4]triazolo[4,3-c]pyrimidin-5-amine
15f |
| 17e | 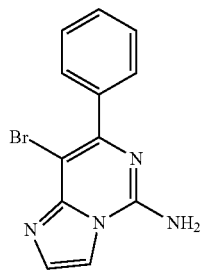

17e

8-Bromo-7-phenylimidazolo[1,2-c]pyrimidin-5-amine
17e |
| 18e | 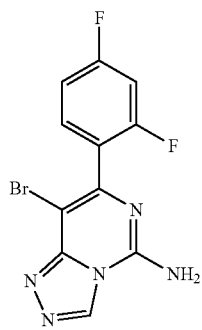

18e

8-Bromo-7-(2,4-difluorophenyl)-[1,2,4]triazolo[4,3-c]pyrimidin-5-amine
18e |

| Example No. | Structure and name of the compound |
|---|---|
| 19d | 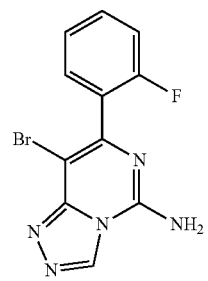

19d

8-Bromo-7-(2-fluorophenyl)-[1,2,4]triazolo[4,3-c]pyrimidin-5-amine
19d |
| 21g | 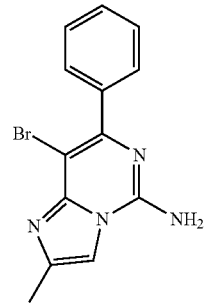

21g

8-Bromo-2-methyl-7-phenylimidazo[1,2-c]pyrimidin-5-amine
21g |
| 29b | 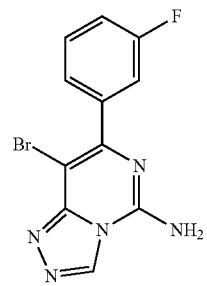

29b

8-Bromo-7-(3-fluorophenyl)-[1,2,4]triazolo[4,3-c]pyrimidin-5-amine
29b |

| Example No. | Structure and name of the compound |
|---|---|
| 32c | 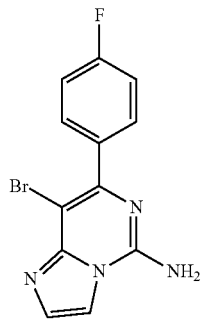<br>32c<br>8-Bromo-7-(4-fluorophenyl)imidazo[1,2-c]pyrimidin-5-amine<br>32c |
| 35b | 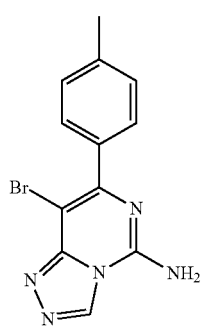<br>35b<br>8-Bromo-7-(p-tolyl)-[1,2,4]triazolo[4,3-c]pyrimidin-5-amine<br>35b |
| 46a | 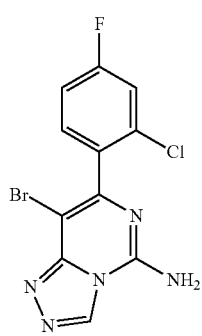<br>46a<br>8-Bromo-7-(2-chloro-4-fluorophenyl)-[1,2,4]triazolo[4,3-c]pyrimidin-5-amine<br>46a |
| 49a | 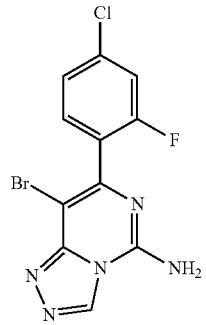<br>49a<br>8-Bromo-7-(4-chloro-2-fluorophenyl)-[1,2,4]triazolo[4,3-c]pyrimidin-5-amine<br>49a |

In another aspect, the present invention relates to a method for preparing the compound of formula (II), comprising a step of:

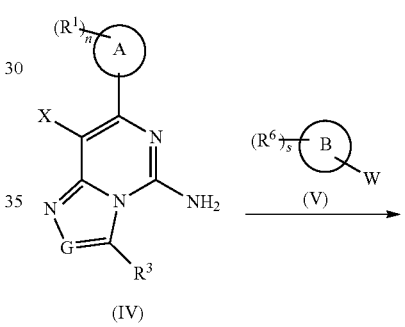

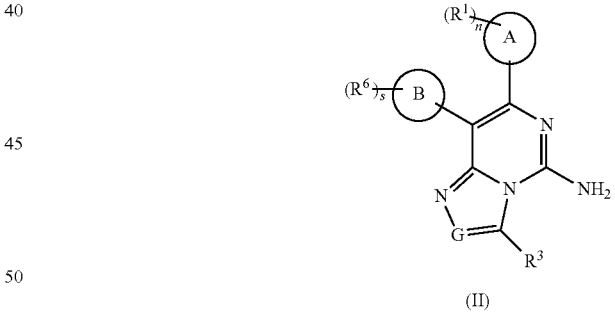

reacting a compound of formula (IV) with a compound of formula (V) to obtain the compound of formula (II),
wherein:
X is a halogen;
W is

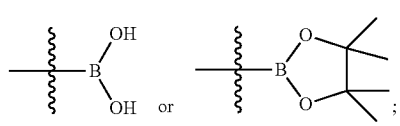

ring A, ring B, G, $R^1$, $R^3$, $R^6$, n and s are as defined in formula (I).

In another aspect, the present invention relates to a pharmaceutical composition comprising a therapeutically effective amount of the compound of formula (I), or a tautomer, mesomer, racemate, enantiomer, diastereomer thereof, or mixture thereof, or a pharmaceutically acceptable salt thereof, and one or more pharmaceutically acceptable carriers, diluents or excipients.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same in the preparation of a medicament for inhibiting the Ata receptor.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same in the preparation of a medicament for treating a disease or condition ameliorated by the inhibition of the $A_{2a}$ receptor.

In the present invention, the disease or condition ameliorated by the inhibition of the $A_{2a}$ receptor is selected from the group consisting of tumor, depression, cognitive function disorder, neurodegenerative disorder (Parkinson's disease, Huntington's disease, Alzheimer's disease or amyotrophic lateral sclerosis and the like), attention-related disorder, extrapyramidal syndrome, abnormal movement disorder, cirrhosis, liver fibrosis, fatty liver, dermal fibrosis, sleep disorder, stroke, brain injury, neuroinflammation and addictive behavior, and preferably tumor.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same in the preparation of a medicament for treating tumor, depression, cognitive function disorder, neurodegenerative disorder (Parkinson's disease, Huntington's disease, Alzheimer's disease or amyotrophic lateral sclerosis and the like), attention-related disorder, extrapyramidal syndrome, abnormal movement disorder, cirrhosis, liver fibrosis, fatty liver, dermal fibrosis, sleep disorder, stroke, brain injury, neuroinflammation and addictive behavior, and preferably tumor.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same in the preparation of a medicament for treating tumor.

The present invention also relates to a method for inhibiting the $A_{2a}$ receptor, comprising a step of administrating to a patient in need thereof a therapeutically effective amount of the compound of formula (I), or a tautomer, mesomer, racemate, enantiomer, diastereomer thereof, or mixture thereof, or a pharmaceutically acceptable salt thereof, or the pharmaceutical composition comprising the same.

The present invention also relates to a method for treating a disease or condition ameliorated by the inhibition of the $A_{2a}$ receptor, comprising a step of administrating to a patient in need thereof a therapeutically effective amount of the compound of formula (I), or a tautomer, mesomer, racemate, enantiomer, diastereomer thereof, or mixture thereof, or a pharmaceutically acceptable salt thereof, or the pharmaceutical composition comprising the same.

The present invention relates to a method for treating tumor, depression, cognitive function disorder, neurodegenerative disorder (Parkinson's disease, Huntington's disease, Alzheimer's disease or amyotrophic lateral sclerosis and the like), attention-related disorder, extrapyramidal syndrome, abnormal movement disorder, cirrhosis, liver fibrosis, fatty liver, dermal fibrosis, sleep disorder, stroke, brain injury, neuroinflammation and addictive behavior, and preferably tumor, comprising a step of administrating to a patient in need thereof a therapeutically effective amount of the compound of formula (I), or a tautomer, mesomer, racemate, enantiomer, diastereomer thereof, or mixture thereof, or a pharmaceutically acceptable salt thereof, or the pharmaceutical composition comprising the same.

The present invention further relates to the compound of formula (I), or a tautomer, mesomer, racemate, enantiomer, diastereomer thereof, or mixture thereof, or a pharmaceutically acceptable salt thereof, or the pharmaceutical composition comprising the same, for use as a medicament.

The present invention also relates to the compound of formula (I), or a tautomer, mesomer, racemate, enantiomer, diastereomer thereof, or mixture thereof, or a pharmaceutically acceptable salt thereof, or the pharmaceutical composition comprising the same, for use as an $A_{2a}$ receptor antagonist.

The present invention also relates to the compound of formula (I), or a tautomer, mesomer, racemate, enantiomer, diastereomer thereof, or mixture thereof, or a pharmaceutically acceptable salt thereof, or the pharmaceutical composition comprising the same, for use in treating a disease or condition ameliorated by the inhibition of the $A_{2a}$ receptor.

The present invention also relates to the compound of formula (I), or a tautomer, mesomer, racemate, enantiomer, diastereomer thereof, or mixture thereof, or a pharmaceutically acceptable salt thereof, or the pharmaceutical composition comprising the same, for use in treating tumor, depression, cognitive function disorder, neurodegenerative disorder (Parkinson's disease, Huntington's disease, Alzheimer's disease or amyotrophic lateral sclerosis and the like), attention-related disorder, extrapyramidal syndrome, abnormal movement disorder, cirrhosis, liver fibrosis, fatty liver, dermal fibrosis, sleep disorder, stroke, brain injury, neuroinflammation and addictive behavior, and preferably tumor.

The present invention further relates to the compound of formula (I), or a tautomer, mesomer, racemate, enantiomer, diastereomer thereof, or mixture thereof, or a pharmaceutically acceptable salt thereof, or the pharmaceutical composition comprising the same, for use in treating tumor.

The tumor described in the present invention is selected from the group consisting of melanoma, brain tumor, esophageal cancer, stomach cancer, liver cancer, pancreatic cancer, colorectal cancer, lung cancer, kidney cancer, breast cancer, ovarian cancer, prostate cancer, skin cancer, neuroblastoma, sarcoma, osteochondroma, osteoma, osteosarcoma, seminoma, testicular tumor, uterine cancer, head and neck tumor, multiple myeloma, malignant lymphoma, polycythemia vera, leukemia, thyroid tumor, ureteral tumor, bladder cancer, gallbladder cancer, cholangiocarcinoma, chorionic epithelioma and pediatric tumor, and preferably lung cancer.

The pharmaceutical composition containing the active ingredient can be in a form suitable for oral administration, for example, a tablet, troche, lozenge, aqueous or oily suspension, dispersible powder or granule, emulsion, hard or soft capsule, syrup or elixir. An oral composition can be prepared according to any known method in the art for the preparation of pharmaceutical composition. Such a composition can contain one or more ingredients selected from the group consisting of sweeteners, flavoring agents, colorants and preservatives, in order to provide a pleasing and palatable pharmaceutical formulation. The tablet contains the active ingredient in admixture with nontoxic, pharmaceutically acceptable excipients suitable for the manufacture of tablets. These excipients can be inert excipients, granulating agents, disintegrating agents, binders and lubricants. The tablet can be uncoated or coated by means of a known technique to mask drug taste or delay the disintegration and absorption of the active ingredient in the gastrointestinal tract, thereby providing sustained release over a long period of time.

An oral formulation can also be provided as soft gelatin capsules in which the active ingredient is mixed with an inert solid diluent, or the active ingredient is mixed with a water-soluble carrier or an oil medium.

An aqueous suspension contains the active ingredient in admixture with excipients suitable for the manufacture of an aqueous suspension. Such excipients are suspending agents, dispersants or wetting agents. The aqueous suspension can also contain one or more preservatives, one or more colorants, one or more flavoring agents, and one or more sweeteners.

An oil suspension can be formulated by suspending the active ingredient in a vegetable oil or mineral oil. The oil suspension can contain a thickener. The aforementioned sweeteners and flavoring agents can be added to provide a palatable formulation. These compositions can be preserved by adding an antioxidant.

The active ingredient in admixture with the dispersants or wetting agents, suspending agent or one or more preservatives can be prepared as dispersible powders or granules suitable for the preparation of an aqueous suspension by adding water. Suitable dispersants or wetting agents and suspending agents are exemplified by those already mentioned above. Additional excipients, such as sweeteners, flavoring agents and colorants, can also be added. These compositions can be preserved by adding an antioxidant, such as ascorbic acid.

The pharmaceutical composition of the present invention can also be in the form of an oil-in-water emulsion. The oil phase can be a vegetable oil, or a mineral oil, or a mixture thereof. Suitable emulsifying agents can be naturally occurring phospholipids. The emulsion can also contain a sweetening agent, flavoring agent, preservative and antioxidant. Such a formulation can also contain a demulcent, preservative, colorant and antioxidant.

The pharmaceutical composition of the present invention can be in the form of a sterile injectable aqueous solution. Acceptable vehicles or solvents that can be used are water, Ringer's solution or isotonic sodium chloride solution. The sterile injectable formulation can be a sterile injectable oil-in-water micro-emulsion in which the active ingredient is dissolved in the oil phase. The injectable solution or microemulsion can be introduced into a patient's bloodstream by local bolus injection. Alternatively, the solution and microemulsion are preferably administrated in a manner that maintains a constant circulating concentration of the compound of the present invention. In order to maintain this constant concentration, a continuous intravenous delivery device can be used. An example of such a device is Deltec CADD-PLUS™ 5400 intravenous injection pump.

The pharmaceutical composition of the present invention can be in the form of a sterile injectable aqueous or oily suspension for intramuscular and subcutaneous administration. Such a suspension can be formulated with suitable dispersants or wetting agents and suspending agents as described above according to known techniques. The sterile injectable formulation can also be a sterile injectable solution or suspension prepared in a nontoxic parenterally acceptable diluent or solvent. Moreover, sterile fixed oils can easily be used as a solvent or suspending medium. For this purpose, any blended fixed oil can be used. In addition, fatty acids can also be used to prepare injections.

The compound of the present invention can be administrated in the form of a suppository for rectal administration. These pharmaceutical compositions can be prepared by mixing the drug with a suitable non-irritating excipient that is solid at ordinary temperatures, but liquid in the rectum, thereby melting in the rectum to release the drug.

It is well known to those skilled in the art that the dosage of a drug depends on a variety of factors including, but not limited to, the following factors: activity of a specific compound, age of the patient, weight of the patient, general health of the patient, behavior of the patient, diet of the patient, administration time, administration route, excretion rate, drug combination and the like. In addition, the optimal treatment, such as treatment mode, daily dose of the compound of formula (I) or the type of pharmaceutically acceptable salt thereof can be verified by traditional therapeutic regimens.

DETAILED DESCRIPTION OF THE INVENTION

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, an alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl group can be substituted or unsubstituted. When substituted, the substituent group(s) can be substituted at any available connection point. The substituent group(s) is preferably one or more groups independently optionally selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl and —C(O)OR$^5$.

The term "alkoxy" refers to an —O-(alkyl) or an —O-(unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl and —C(O)OR$^5$.

The term "cycloalkyl" refers to a saturated or partially unsaturated monocyclic or polycyclic hydrocarbon substituent group having 3 to 20 carbon atoms, preferably 3 to 12 carbon atoms, preferably 3 to 10 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring. The cycloalkyl can be substituted or unsubstituted. When substituted, the substituent group(s) can be substituted at any available connection point. The substituent group(s) is preferably one or more group(s) independently optionally selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl and —C(O)OR$^5$.

The term "heterocyclyl" refers to a 3 to 20 membered saturated or partially unsaturated monocyclic or polycyclic hydrocarbon group, wherein one or more ring atoms are heteroatoms selected from the group consisting of N, O and S(O)$_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms, more preferably, 3 to 10 ring atoms wherein 1 to 4 atoms are heteroatoms, and more preferably 5 to 6 ring atoms wherein 1 to 3 atoms are heteroatoms. Non-limiting examples of monocyclic heterocyclyl include pyrrolidinyl, tetrahydropyranyl, 1,2,3,6-tetrahydropyridyl, piperidinyl, piperazinyl, morpholinyl, thiomorpholinyl, homopiperazinyl and the like. Polycyclic heterocyclyl includes a heterocyclyl having a spiro ring, fused ring or bridged ring.

The ring of heterocyclyl can be fused to the ring of aryl, heteroaryl or cycloalkyl, wherein the ring bound to the parent structure is heterocyclyl. Non-limiting examples thereof include:

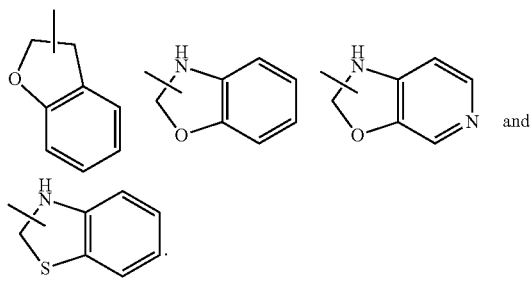

The heterocyclyl can be substituted or unsubstituted. When substituted, the substituent group(s) can be substituted at any available connection point. The substituent group(s) is preferably one or more group(s) independently optionally selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl and —C(O)OR$^5$.

The term "aryl" refers to a 6 to 14 membered all-carbon monocyclic ring or polycyclic fused ring (i.e., each ring in the system shares an adjacent pair of carbon atoms with another ring in the system) having a conjugated π-electron system, preferably 6 to 10 membered aryl, for example, phenyl and naphthyl. The ring of aryl can be fused to the ring of heteroaryl, heterocyclyl or cycloalkyl, wherein the ring bound to the parent structure is aryl ring. Non-limiting examples thereof include:

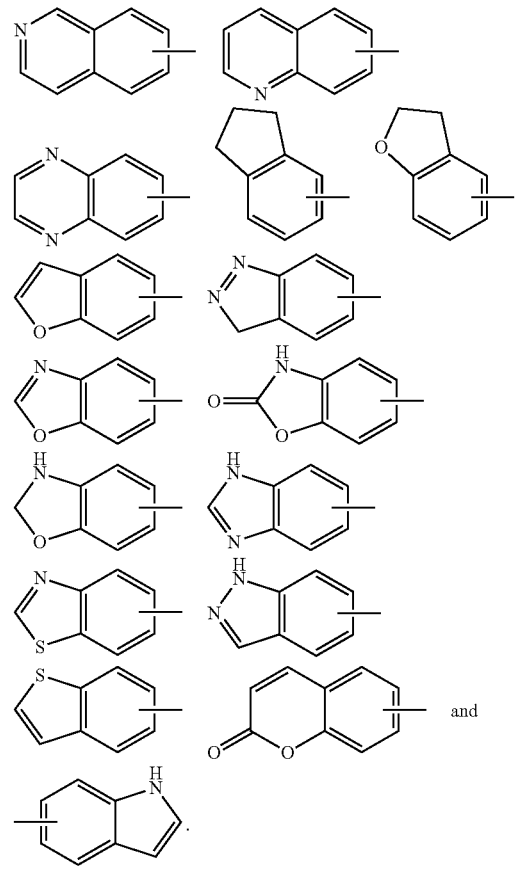

The aryl can be substituted or unsubstituted. When substituted, the substituent group(s) can be substituted at any available connection point. The substituent group(s) is preferably one or more group(s) independently optionally selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl and —C(O)OR$^5$.

The term "heteroaryl" refers to a 5 to 14 membered heteroaromatic system having 1 to 4 heteroatoms selected from the group consisting of O, S and N. The heteroaryl is preferably 5 to 10 membered heteroaryl, more preferably 5 or 6 membered heteroaryl, for example, furanyl, thienyl, pyridyl, pyrrolyl, N-alkylpyrrolyl, pyrimidinyl, pyrazinyl, pyridazinyl, imidazolyl, pyrazolyl, tetrazolyl and the like. The ring of heteroaryl can be fused to the ring of aryl, heterocyclyl or cycloalkyl, wherein the ring bound to the parent structure is heteroaryl ring. Non-limiting examples thereof include:

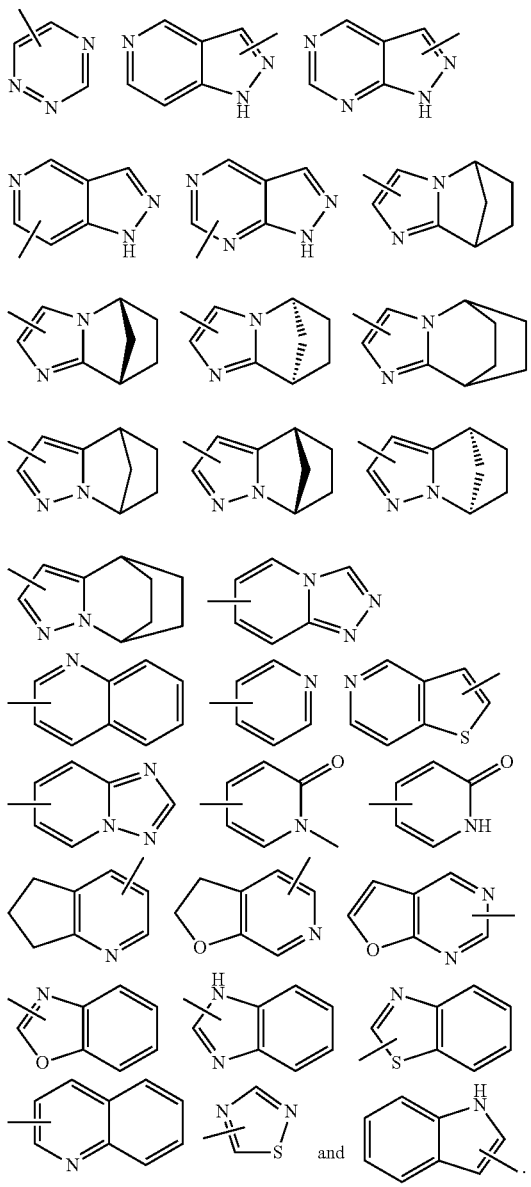

The heteroaryl can be substituted or unsubstituted. When substituted, the substituent group(s) can be substituted at any available connection point. The substituent group(s) is preferably one or more group(s) independently optionally selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl and —C(O)OR$^5$.

The term "oxo" refers to a=O group.

The term "cycloalkyloxy" refers to a cycloalkyl-O— group.

The term "heterocyclylalkyl" refers to an alkyl group substituted by one or more heterocyclyl, wherein the alkyl and heterocyclyl are as defined above. The term "haloalkyl" refers to an alkyl group substituted by one or more halogen, wherein the alkyl is as defined above.

The term "hydroxy" refers to an —OH group.

The term "hydroxyalkyl" refers to an alkyl group substituted by hydroxy(s), wherein the alkyl is as defined above.

The term "halogen" refers to fluorine, chlorine, bromine or iodine.

The term "amino" refers to a —NH$_2$ group.

The term "cyano" refers to a —CN group.

The term "nitro" refers to a —NO$_2$ group.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, and more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity.

A "pharmaceutically acceptable salt" refers to a salt of the compound of the present invention, which is safe and effective in mammals and has the desired biological activity.

Synthesis Method of the Compound of the Present Invention

In order to achieve the object of the present invention, the present invention applies the following technical solutions:

Scheme I

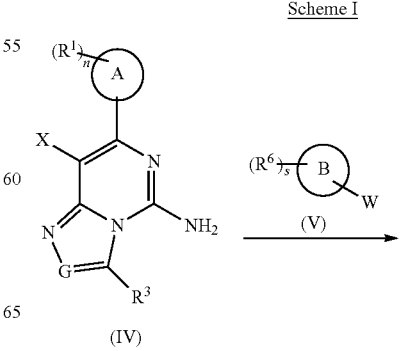

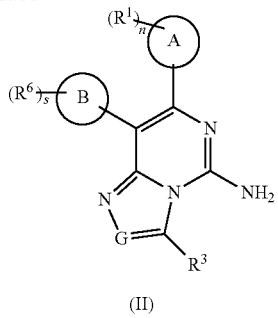

(II)

A method for preparing the compound of formula (II) of the present invention or a tautomer, mesomer, racemate, enantiomer, diastereomer thereof, or mixture thereof, or a pharmaceutically acceptable salt thereof, comprises the following step of:

a compound of formula (IV) and a compound of formula (V) are subjected to a suzuki coupling reaction in the presence of a catalyst under an alkaline condition to obtain the compound of formula (II).

Wherein:

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide.

The catalyst includes, but is not limited to, Pd/C, Raney Ni, tetra-triphenylphosphine palladium, palladium dichloride, palladium acetate, bis(dibenzylideneacetone)palladium, chloro(2-dicyclohexylphosphino-2',4',6'-triisopropyl-1,1'-biphenyl)[2-(2'-amino-1,1'-bip henyl)]palladium, [1,1'-bis(diphenylphosphino)ferrocene]dichloropalladium, 1,1'-bis(dibenzylphosphoryl)ferrocene palladium dichloride and tris(dibenzylideneacetone)dipalladium, and preferably [1,1'-bis(diphenylphosphino)ferrocene]dichloropalladium.

The above reaction is preferably carried out in a solvent. The solvent used includes, but is not limited to, acetic acid, methanol, ethanol, n-butanol, toluene, tetrahydrofuran, dichloromethane, petroleum ether, ethyl acetate, n-hexane, dimethyl sulfoxide, 1,4-dioxane, glycol dimethyl ether, water, N,N-dimethylformamide, and mixtures thereof.

Wherein:

X is a halogen;

W is

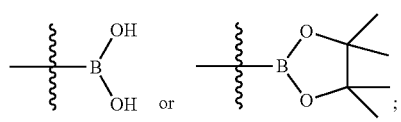

ring A, ring B, G, $R^1$, $R^3$, $R^6$, n and s are as defined in formula (II).

Scheme II

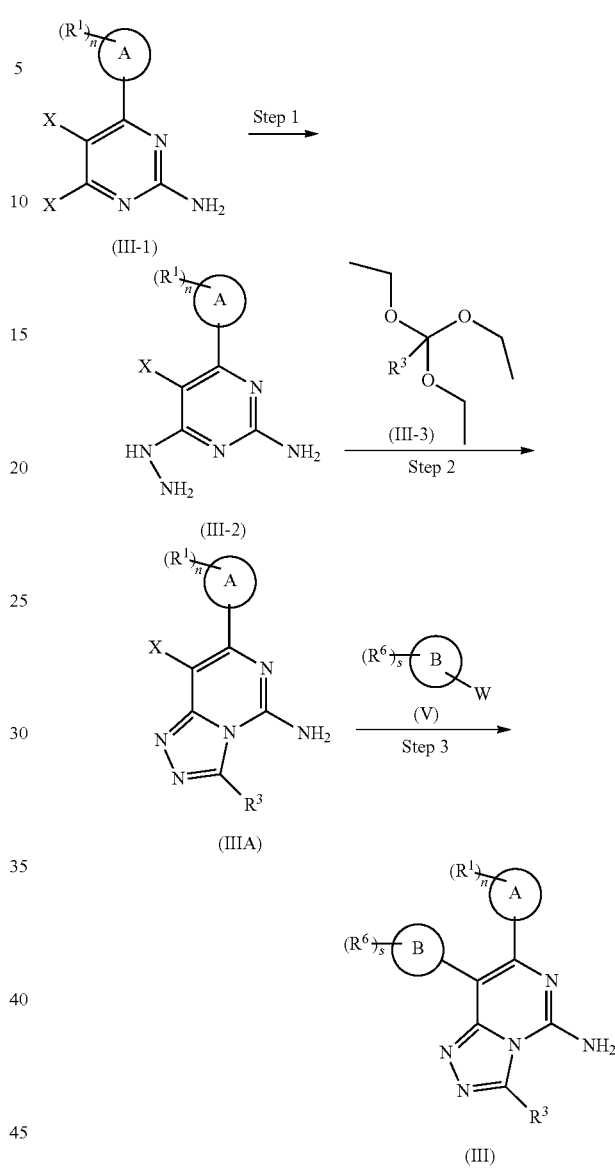

A method for preparing the compound of formula (III) of the present invention or a tautomer, mesomer, racemate, enantiomer, diastereomer thereof, or mixture thereof, or a pharmaceutically acceptable salt thereof, comprises the following steps of:

in Step 1, a compound of formula (III-1) is reacted with hydrazine hydrate to obtain a compound of formula (III-2);

in Step 2, the compound of formula (III-2) is reacted with a compound of formula (III-3) to obtain a compound of formula (IIIA);

in Step 3, the compound of formula (IIIA) and a compound of formula (V) are subjected to a suzuki coupling reaction in the presence of a catalyst under an alkaline condition to obtain the compound of formula (III).

Wherein:

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide.

The catalyst includes, but is not limited to, Pd/C, Raney Ni, tetra-triphenylphosphine palladium, palladium dichloride, palladium acetate, bis(dibenzylideneacetone)palladium, chloro(2-dicyclohexylphosphino-2',4',6'-triisopropyl-1,1'-biphenyl)[2-(2'-amino-1, 1'-biphenyl)]palladium, [1,1'-bis(diphenylphosphino)ferrocene]dichloropalladium, 1,1'-bis(dibenzylphosphoryl)ferrocene palladium dichloride and tris(dibenzylideneacetone)dipalladium, and preferably [1,1'-bis(diphenylphosphino)ferrocene]dichloropalladium.

The above reaction is preferably carried out in a solvent. The solvent used includes, but is not limited to, acetic acid, methanol, ethanol, n-butanol, toluene, tetrahydrofuran, dichloromethane, petroleum ether, ethyl acetate, n-hexane, dimethyl sulfoxide, 1,4-dioxane, glycol dimethyl ether, water, N,N-dimethylformamide, and mixtures thereof.

Wherein:

X is a halogen;

W is

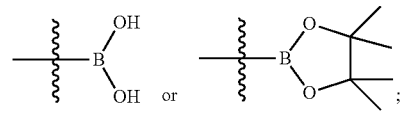

ring A, ring B, $R^1$, $R^3$, $R^6$, n and s are as defined in formula (III).

Scheme III

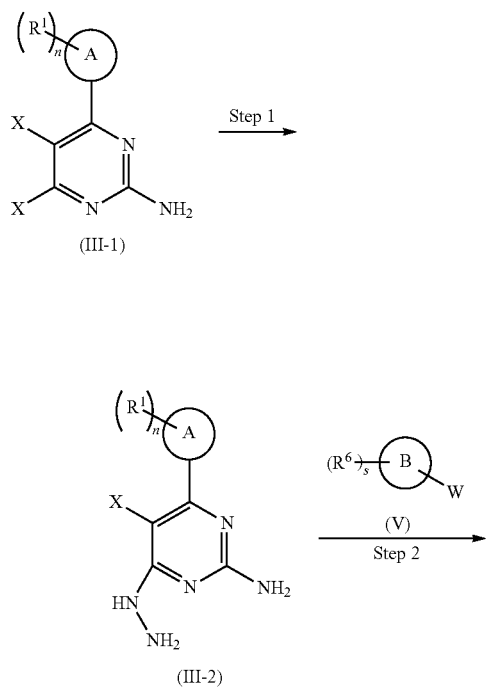

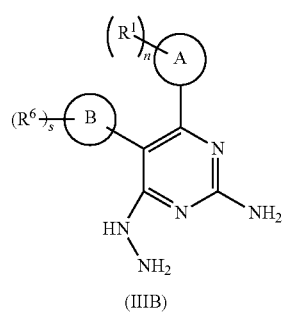

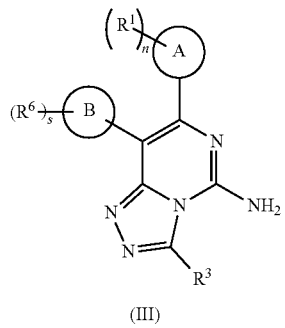

A method for preparing the compound of formula (III) of the present invention or a tautomer, mesomer, racemate, enantiomer, diastereomer thereof, or mixture thereof, or a pharmaceutically acceptable salt thereof, comprises the following steps:

in Step 1, a compound of formula (III-1) is reacted with hydrazine hydrate to obtain a compound of formula (III-2);

in Step 2, the compound of formula (III-2) and a compound of formula (V) are subjected to a suzuki coupling reaction in the presence of a catalyst under an alkaline condition to obtain a compound of formula (IIIB);

in Step 3, the compound of formula (IIIB) is reacted with a compound of formula (III-3) to obtain the compound of formula (III).

Wherein:

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide.

The catalyst includes, but is not limited to, Pd/C, Raney Ni, tetra-triphenylphosphine palladium, palladium dichloride, palladium acetate, bis(dibenzylideneacetone)palladium, chloro(2-dicyclohexylphosphino-2',4',6'-triisopropyl-1,1'-biphenyl)[2-(2'-amino-1, 1'-biphenyl)]palladium, [1,1'-bis(diphenylphosphino)ferrocene]dichloropalladium, 1,1'-bis(dibenzylphosphoryl)ferrocene palladium dichloride and tris(dibenzylideneacetone)dipalladium, and preferably [1,1'-bis(diphenylphosphino)ferrocene]dichloropalladium.

The above reaction is preferably carried out in a solvent. The solvent used includes, but is not limited to, acetic acid, methanol, ethanol, n-butanol, toluene, tetrahydrofuran, dichloromethane, petroleum ether, ethyl acetate, n-hexane, dimethyl sulfoxide, 1,4-dioxane, glycol dimethyl ether, water, N,N-dimethylformamide, and mixtures thereof.

Wherein:
X is a halogen;
W is

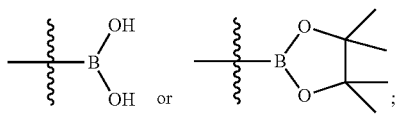

ring A, ring B, $R^1$, $R^3$, $R^6$, n and s are as defined in formula (III).

Scheme IV

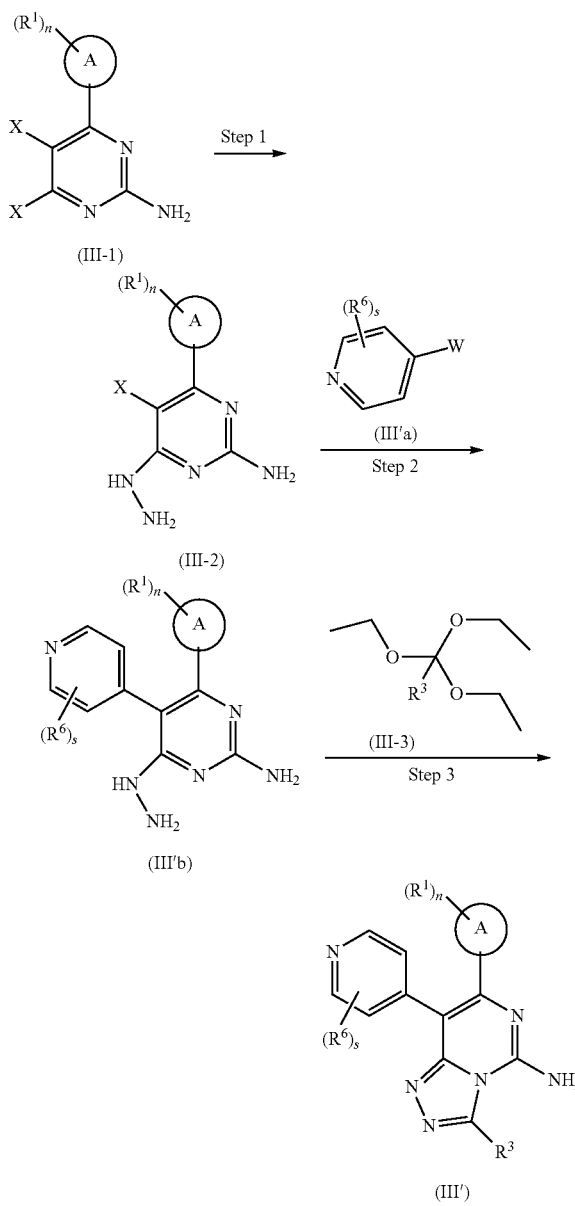

A method for preparing the compound of formula (III') of the present invention or a tautomer, mesomer, racemate, enantiomer, diastereomer thereof, or mixture thereof, or a pharmaceutically acceptable salt thereof, comprises the following steps of:

in Step 1, a compound of formula (III-1) is reacted with hydrazine hydrate to obtain a compound of formula (III-2);

in Step 2, the compound of formula (III-2) and a compound of formula (III'a) are subjected to a suzuki coupling reaction in the presence of a catalyst under an alkaline condition to obtain a compound of formula (III'b);

in Step 3, the compound of formula (III'b) is reacted with a compound of formula (III-3) to obtain the compound of formula (III').

Wherein:

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide.

The catalyst includes, but is not limited to, Pd/C, Raney Ni, tetra-triphenylphosphine palladium, palladium dichloride, palladium acetate, bis(dibenzylideneacetone)palladium, chloro(2-dicyclohexylphosphino-2',4',6'-triisopropyl-1,1'-biphenyl)[2-(2'-amino-1,1'-bip henyl)]palladium, [ 1,1'-bis(diphenylphosphino)ferrocene]dichloropalladium, 1,1'-bis(dibenzylphosphoryl)ferrocene palladium dichloride and tris(dibenzylideneacetone)dipalladium, and preferably [1,1'-bis(diphenylphosphino)ferrocene]dichloropalladium.

The above reaction is preferably carried out in a solvent. The solvent used includes, but is not limited to, acetic acid, methanol, ethanol, n-butanol, toluene, tetrahydrofuran, dichloromethane, petroleum ether, ethyl acetate, n-hexane, dimethyl sulfoxide, 1,4-dioxane, glycol dimethyl ether, water, N,N-dimethylformamide, and mixtures thereof Wherein:
X is a halogen;
W is

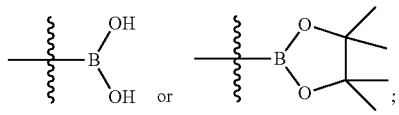

ring A, $R^1$, $R^3$, $R^6$, n and s are as defined in formula (III).

PREFERRED EMBODIMENTS

The present invention will be further described with reference to the following examples, but the examples should not be considered as limiting the scope of the present invention.

EXAMPLES

The structures of the compounds were identified by nuclear magnetic resonance (NMR) and/or mass spectrometry (MS). NMR shifts (δ) are given in $10^{-6}$ (ppm). NMR was determined by a Bruker AVANCE-400 machine. The solvents for determination were deuterated-dimethyl sulfoxide (DMSO-$d_6$), deuterated-chloroform (CDCl$_3$) and deuterated-methanol (CD$_3$OD), and the internal standard was tetramethylsilane (TMS).

MS was determined by a FINNIGAN LCQAd (ESI) mass spectrometer (manufacturer: Thermo, type: Finnigan LCQ advantage MAX).

High performance liquid chromatography (HPLC) was determined on an Agilent 1200DAD high pressure liquid chromatograph (Sunfire C18 150×4.6 mm chromatographic column) and Waters 2695-2996 high pressure liquid chromatograph (Gimini C18 150×4.6 mm chromatographic column).

Chiral HPLC analysis was determined on a LC-10A vp (Shimadzu) or SFC-analytical (Berger Instruments Inc.).

Yantai Huanghai HSGF254 or Qingdao GF254 silica gel plate was used as the thin-layer silica gel chromatography (TLC) plate. The dimension of the silica gel plate used in TLC was 0.15 mm to 0.2 mm, and the dimension of the silica gel plate used in product purification was 0.4 mm to 0.5 mm.

Yantai Huanghai 200 to 300 mesh silica gel was generally used as a carrier for column chromatography.

Prep Star SD-1 (Varian Instruments Inc.) or SFC-multigram (Berger Instruments Inc.) was used for chiral preparative column chromatography.

CombiFlash rapid preparation instrument used was Combiflash Rf200 (TELEDYNE ISCO).

The average kinase inhibition rates and IC$_{50}$ values were determined by a NovoStar ELISA (BMG Co., Germany).

The known starting materials of the present invention can be prepared by the known methods in the art, or can be purchased from ABCR GmbH & Co. KG, Acros Organnics, Aldrich Chemical Company, Accela ChemBio Inc., or Dari chemical Company, etc.

Unless otherwise stated, the reactions were carried out under argon atmosphere or nitrogen atmosphere.

"Argon atmosphere" or "nitrogen atmosphere" means that a reaction flask is equipped with an argon or nitrogen balloon (about 1 L).

"Hydrogen atmosphere" means that a reaction flask is equipped with a hydrogen balloon (about 1 L).

Pressurized hydrogenation reactions were performed on a Parr 3916EKX hydrogenation instrument and a Qinglan QL-500 hydrogen generator or HC2-SS hydrogenation instrument.

In hydrogenation reactions, the reaction system was generally vacuumed and filled with hydrogen, and the above operation was repeated three times.

CEM Discover-S 908860 type microwave reactor was used in microwave reactions.

Unless otherwise stated, the solution refers to an aqueous solution.

Unless otherwise stated, the reaction temperature is room temperature from 20° C. to 30° C.

The reaction process in the examples was monitored by thin layer chromatography (TLC). The developing solvent used in the reactions, the eluent system in column chromatography and the developing solvent system in thin layer chromatography for purification of the compounds included: A: dichloromethane/methanol system, B: n-hexane/ethyl acetate system, C: petroleum ether/ethyl acetate system, D: acetone, E: dichloromethane/acetone system, F: ethyl acetate/dichloromethane system, G: ethyl acetate/dichloromethane/n-hexane, and H: ethyl acetate/dichloromethane/acetone. The ratio of the volume of the solvent was adjusted according to the polarity of the compounds, and a small quantity of alkaline reagent such as triethylamine or acidic reagent such as acetic acid can also be added for adjustment.

Example 1

8-(2-Methyl-6-(trifluoromethyl)pyridin-4-yl)-7-phenyl-[1,2,4]triazolo[4,3-c]pyrimidin-5-amine 1

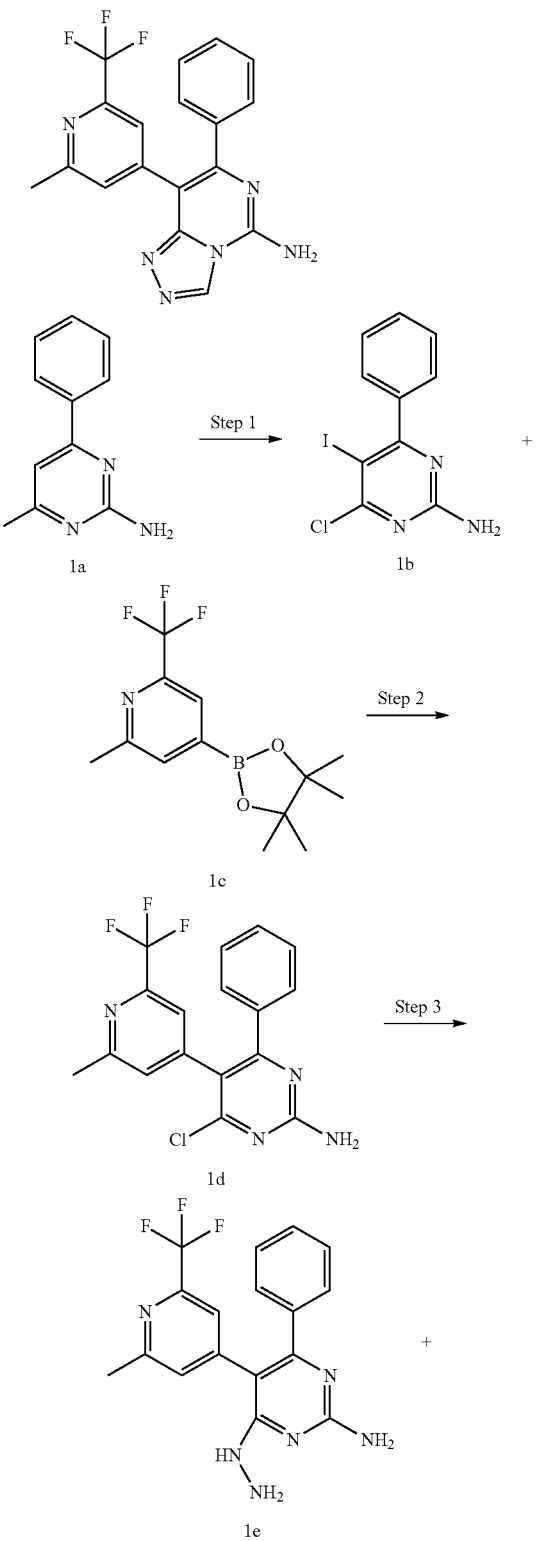

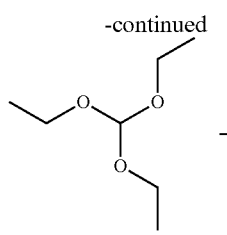

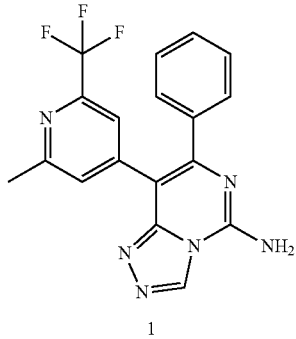

Step 1

4-Chloro-5-iodo-6-phenylpyrimidin-2-amine 1b

4-Chloro-6-phenylpyrimidin-2-amine 1a (2 g, 9.75 mmol, prepared according to the known method disclosed in "Bioorganic & Medicinal Chemistry Letters, 2011, 21(8), 2497-2501") and N-iodosuccinimide (2.6 g, 11.7 mmol) were dissolved in 30 mL of acetic acid. After completion of the addition, the reaction solution was stirred for 16 hours. The reaction solution was added with 200 mL of saturated sodium bicarbonate solution, and extracted with ethyl acetate (100 mL×3). The organic phases were combined, washed with saturated sodium chloride solution (100 mL), dried over anhydrous sodium sulfate, and filtrated to collect the filtrate. The filtrate was concentrated under reduced pressure, and the residue was purified by silica gel chromatography with eluent system B to obtain the title compound 1b (2.88 g, yield: 89%).

MS m/z (ESI): 332.2 [M+1]

Step 2

4-Chloro-5-(2-methyl-6-(trifluoromethyl)pyridin-4-yl)-6-phenylpyrimidin-2-amine 1d Compound 1b (2.88 g, 8.7 mmol), 2-methyl-4-(4,4,5,5-tetramethyl-1,3,2-dioxaborolan-2-yl)-6-(trifluoromethyl) pyridine 1c (2.7 g, 9.17 mmol, prepared according to the known method disclosed in "Journal of Medicinal Chemistry, 2012, 55(5), 1898-1903"), [1,1'-bis(diphenylphosphino) ferrocene]dichloropalladium (0.64 g, 0.87 mmol) and potassium carbonate (3.6 g, 26.1 mmol) were dissolved successively in 66 mL of a mixed solution of 1,4-dioxane and water (V/V=10:1) under a nitrogen atmosphere. The reaction solution was heated to 83° C., and stirred for 3 hours. The reaction was stopped, and the reaction solution was cooled to room temperature and filtrated. The filtrate was added with 200 mL of ethyl acetate, washed with saturated sodium chloride solution (100 mL), dried over anhydrous sodium sulfate, and filtrated to collect the filtrate. The filtrate was concentrated under reduced pressure, and the residue was purified by silica gel chromatography with eluent system B to obtain the title compound 1d (2.4 g, yield: 76%).

MS m/z (ESI): 365.4 [M+1]

Step 3

4-Hydrazinyl-5-(2-methyl-6-(trifluoromethyl)pyridin-4-yl)-6-phenylpyrimidin-2-amine 1e Compound 1d (100 mg, 0.275 mmol) and 85% hydrazine hydrate (62 mg, 2.747 mmol) were dissolved successively in 10 mL of ethanol. The reaction solution was stirred under reflux for 17 hours. The reaction was stopped, and the reaction solution was cooled to room temperature. The reaction solution was added with 30 mL of water, and extracted with ethyl acetate (30 mL×3). The organic phases were combined, washed with saturated sodium chloride solution (50 mL×2), dried over anhydrous sodium sulfate, and filtrated to collect the filtrate. The filtrate was concentrated under reduced pressure to obtain the crude title compound 1e (85 mg), which was used directly in the next step without purification.

MS m/z (ESI): 361.4 [M+1]

Step 4

8-(2-Methyl-6-(trifluoromethyl)pyridin-4-yl)-7-phenyl-[1,2,4] triazolo[4,3-c]pyrimidin-5-amine 1

The crude product 1e (85 mg, 0.275 mmol) was added to 2 mL of (tri)ethyl orthoformate. The reaction solution was stirred at 140° C. for 0.5 hour. The reaction was stopped, and the reaction solution was cooled to room temperature and concentrated under reduced pressure. The resulting residue was purified by high performance liquid chromatography to obtain the title compound 1 (6 mg, yield: 6.9%).

MS m/z (ESI): 371.4 [M+1]

$^1$H NMR (400 MHz, DMSO-$d_6$) δ 9.38 (s, 1H), 8.42 (brs, 2H), 7.59 (s, 1H), 7.42 (s, 1H), 7.35-7.31 (m, 5H), 2.48 (s, 3H).

Example 2

7-Phenyl-8-(1H-pyrazol-4-yl)-[1,2,4]triazolo[4,3-c]pyrimidin-5-amine 2

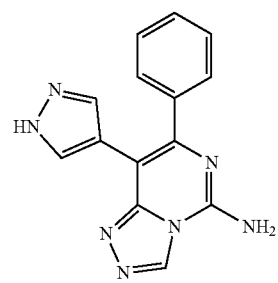

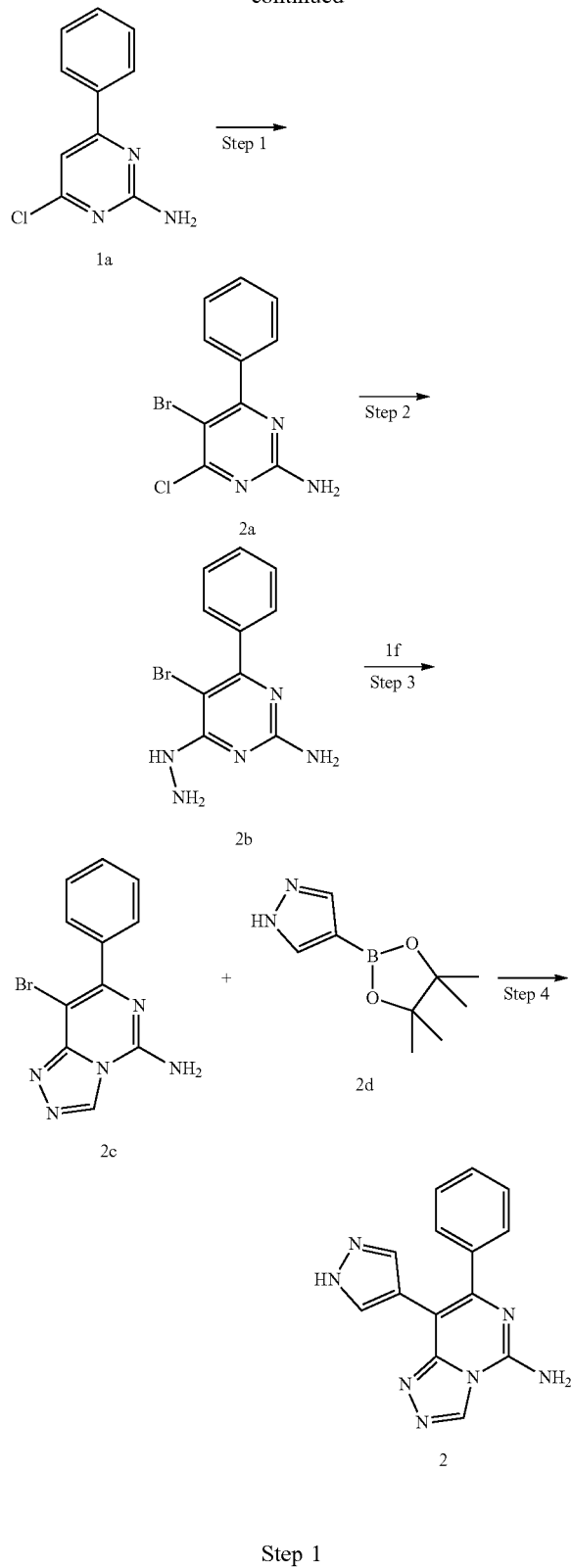

the reaction solution was stirred for 1 hour. The reaction solution was added with 50 mL of water, and extracted with ethyl acetate (50 mL×3). The organic phases were combined, washed with water (100 mL×3) and saturated sodium chloride solution (200 mL) successively, dried over anhydrous sodium sulfate, and filtrated to collect the filtrate. The filtrate was concentrated under reduced pressure to obtain the crude title compound 2a (698 mg), which was used directly in the next step without purification.

MS m/z (ESI): 284.2 [M+1]

Step 2

5-Bromo-4-hydrazinyl-6-phenylpyrimidin-2-amine 2b

The crude product 2a (692 mg, 2.432 mmol) and 85% hydrazine hydrate (1.432 mg, 24.32 mmol) were dissolved successively in 20 mL of ethanol. The reaction solution was stirred under reflux for 1 hour. The reaction solution was cooled to room temperature, and stirred for 0.5 hour. The reaction solution was filtrated, and the filter cake was washed with ethanol (3 mL×2) and ether (3 mL×2) successively. The filter cake was collected, and dried to obtain the crude title compound 2b (480 mg), which was used directly in the next step without purification.

MS m/z (ESI): 280.3 [M+1]

Step 3

8-Bromo-7-phenyl-[1,2,4]triazolo[4,3-c]pyrimidin-5-amine 2c

The crude product 2b (480 mg, 1.713 mmol) was added to 5 mL of (tri)ethyl orthoformate. The reaction solution was stirred at 140° C. for 15 minutes. The reaction was stopped, and the reaction solution was cooled to room temperature and filtrated. The filter cake was washed with ethanol (3 mL×3) and diethyl ether (5 mL×3) successively. The filter cake was collected, and dried to obtain the title compound 2c (348 mg, yield: 62.4%).

MS m/z (ESI): 290.3 [M+1]

Step 4

7-Phenyl-8-(1H-pyrazol-4-yl)-[1,2,4]triazolo[4,3-c]pyrimidin-5-amine 2

Compound 2c (120 mg, 0.414 mmol), 4-(4,4,5,5-tetramethyl-1,3,2-dioxaborolan-2-yl)-1H-pyrazole 2d (120 mg, 0.620 mmol, prepared according to the known method disclosed in "Journal of the American Chemical Society, 2014, 136(11), 4287-4299"), [1,1'-bis(diphenylphosphino)ferrocene]dichloropalladium (30 mg, 0.041 mmol) and potassium carbonate (171 mg, 1.241 mmol) were dissolved successively in 6 mL of a mixed solution of 1,4-dioxane and water (V/V=5:1) under an argon atmosphere. The reaction solution was heated to 90° C., and stirred for 3 hours. The reaction was stopped, and the reaction solution was added with 50 mL of water and extracted with ethyl acetate (30 mL×3). The organic phase was concentrated under reduced pressure, and the residue was purified by high performance liquid chromatography to obtain the title compound 2 (33 mg, yield: 28.7%).

MS m/z (ESI): 278.4 [M+1]

Step 1

5-Bromo-4-chloro-6-phenylpyrimidin-2-amine 2a

Compound 1a (500 mg, 2.431 mmol) and N-bromosuccinimide (519 mg, 2.918 mmol) were dissolved in 16 mL of N,N-dimethylformamide. After completion of the addition, $^1$H NMR (400 MHz, DMSO-d$_6$) δ 12.79 (brs, 1H), 9.32 (s, 1H), 7.98 (brs, 2H), 7.41-7.37 (m, 7H).

Example 3

7-Phenyl-8-(quinolin-6-yl)-[1,2,4]triazolo[4,3-c]pyrimidin-5-amine 3

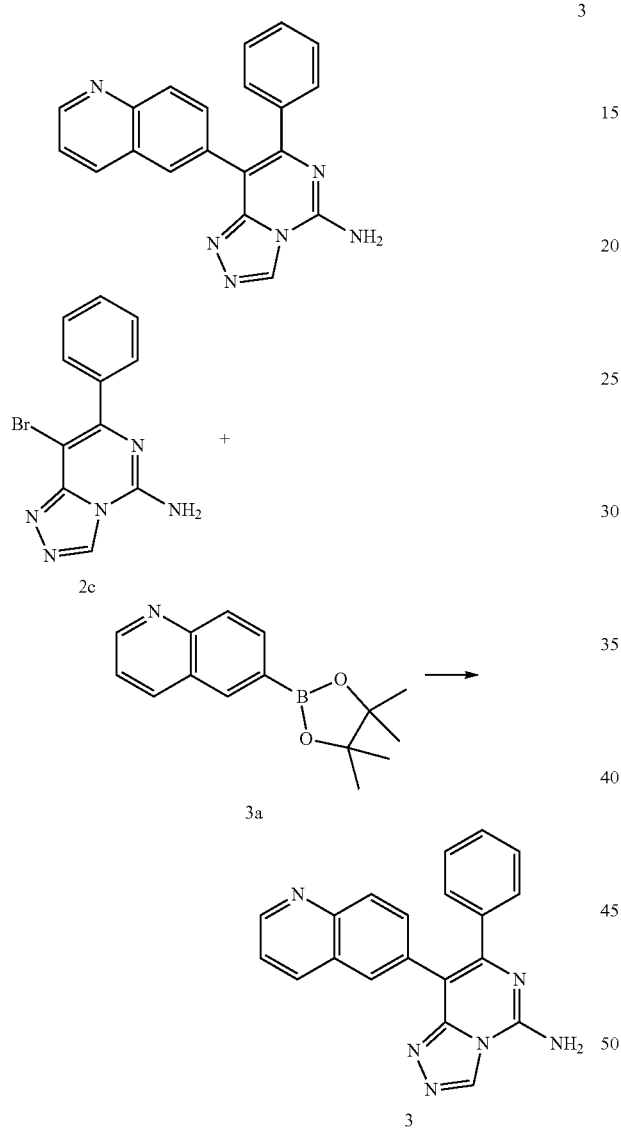

Compound 2c (100 mg, 0.345 mmol), 6-(4,4,5,5-tetramethyl-1,3,2-dioxaborolan-2-yl)quinoline 3a (106 mg, 0.414 mmol, prepared according to the known method disclosed in "*Journal of the American Chemical Society,* 2013, 135(50), 18730-18733"), [1,1'-bis(diphenylphosphino)ferrocene]dichloropalladium (25 mg, 0.034 mmol) and potassium carbonate (143 mg, 1.034 mmol) were dissolved successively in 6 mL of a mixed solution of 1,4-dioxane and water (V/V=5:1) under an argon atmosphere. The reaction solution was heated to 90° C., and stirred for 2 hours. The reaction was stopped, and the reaction solution was added with 50 mL of water and extracted with ethyl acetate (50 mL×3). The organic phase was concentrated under reduced pressure, and the residue was purified by silica gel chromatography with eluent system A to obtain the title compound 3 (49 mg, yield: 41.9%).

MS m/z (ESI): 339.2 [M+1]

$^1$H NMR (400 MHz, DMSO-d$_6$) δ 9.38 (s, 1H), 8.88-8.87 (m, 1H), 8.29-8.27 (m, 1H), 8.20 (brs, 2H), 8.05-8.04 (m, 1H), 7.88-7.85 (m, 1H), 7.54-7.50 (m, 2H), 7.37-7.34 (m, 2H), 7.24-7.20 (m, 3H).

Example 4

8-(2-Chloro-6-methylpyridin-4-yl)-7-phenyl-[1,2,4]triazolo[4,3-c]pyrimidin-5-amine 4

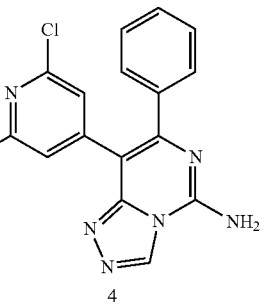

Compound 2c (100 mg, 0.345 mmol), 2-chloro-6-methyl-4-(4,4,5,5-tetramethyl-1,3,2-dioxaborolan-2-yl)pyridine 4a (105 mg, 0.414 mmol, prepared according to the known method disclosed in "*Organic Syntheses,* 2005, 82, 126-133"), [1,1'-bis(diphenylphosphino)ferrocene]dichloropalladium (25 mg, 0.034 mmol) and potassium carbonate (143 mg, 1.034 mmol) were dissolved successively in 10 mL of a mixed solution of 1,4-dioxane and water (V/V=4:1) under an argon atmosphere. The reaction solution was heated to 90° C., and stirred for 3 hours. The reaction was stopped, and the reaction solution was added with 50 mL of water and extracted with ethyl acetate (30 mL×4). The organic phase was concentrated under reduced pressure, and the residue was purified by high performance liquid chromatography to obtain the title compound 4 (20.7 mg, yield: 17.8%).

MS m/z (ESI): 337.4 [M+1]

¹H NMR (400 MHz, DMSO-d₆) δ9.36 (s, 1H), 8.38 (brs, 2H), 7.36-7.32 (m, 5H), 7.19-7.14 (m, 2H), 2.35 (s, 3H).

Example 5

8-(8-Methylquinolin-6-yl)-7-phenyl-[1,2,4]triazolo[4,3-c]pyrimidin-5-amine 5

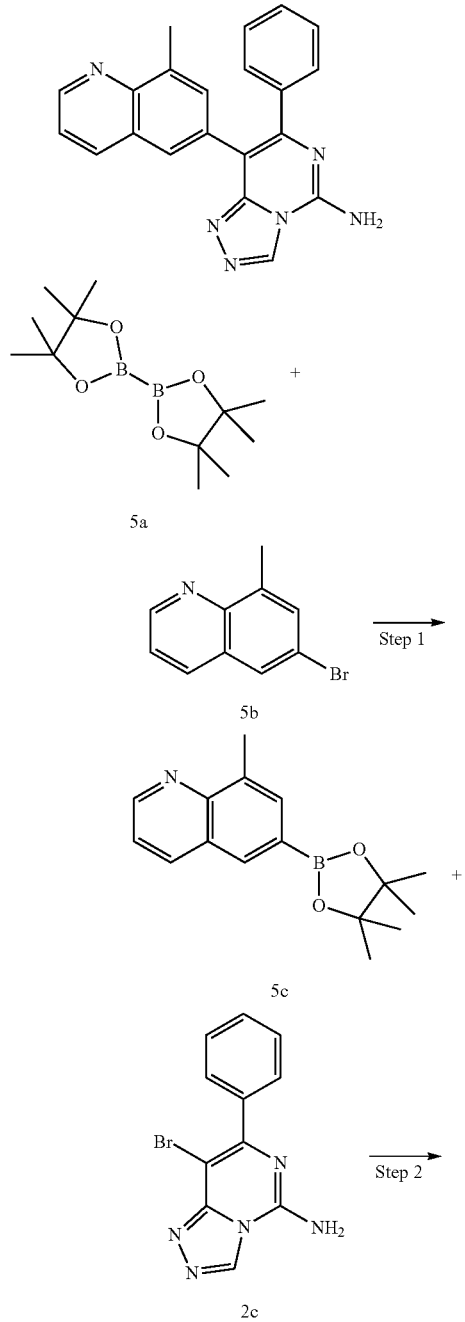

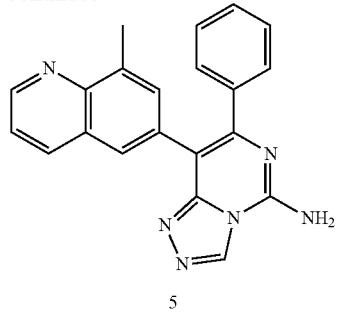

Step 1

8-Methyl-6-(4,4,5,5-tetramethyl-1,3,2-dioxaborolan-2-yl)quinoline 5c

6-Bromo-8-methylquinoline 5b (444 mg, 2.00 mmol, prepared according to the known method disclosed in "*Journal of Organic Chemistry*, 2014, 79(11), 5379-5385"), 4,4,4',4',5,5,5',5'-octamethyl-2,2'-bi(1,3,2-dioxaborolane) 5a (508 mg, 2.00 mmol), [1,1'-bis(diphenylphosphino)ferrocene]dichloropalladium (292 mg, 0.40 mmol) and potassium acetate (588 mg, 6.00 mmol) were dissolved successively in 10 mL of glycol dimethyl ether under an argon atmosphere. The reaction solution was heated to 80° C., and stirred for 12 hours. The reaction was stopped, and the reaction solution was cooled to room temperature and filtrated. The filtrate was added with 20 mL of ethyl acetate, washed successively with water (10 mL) and saturated sodium chloride solution (10 mL), dried over anhydrous sodium sulfate, and filtrated. The filtrate was concentrated under reduced pressure, and the residue was purified by thin layer chromatography with developing solvent system B to obtain the title compound 5c (320 mg, yield: 59.5%).

MS m/z (ESI): 270.1 [M+1]

Step 2

8-(8-Methylquinolin-6-yl)-7-phenyl-[1,2,4]triazolo[4,3-c]pyrimidin-5-amine 5

Compound 2c (100 mg, 0.345 mmol), 5c (130 mg, 0.482 mmol), [1,1'-bis(diphenylphosphino)ferrocene]dichloropalladium (25 mg, 0.034 mmol) and potassium carbonate (143 mg, 1.034 mmol) were dissolved successively in 5 mL of a mixed solution of 1,4-dioxane and water (V/V=4:1) under an argon atmosphere. The reaction solution was heated to 90° C., and stirred for 2 hours. The reaction was stopped, and the reaction solution was added with 50 mL of water and extracted with ethyl acetate (30 mL×3). The organic phase was concentrated under reduced pressure, and the residue was purified by high performance liquid chromatography to obtain the title compound 5 (32 mg, yield: 26.4%).

MS m/z (ESI): 353.2 [M+1]

¹H NMR (400 MHz, DMSO-d₆) δ 19.37 (s, 1H), 8.90-8.89 (m, 1H), 8.21-8.19 (m, 3H), 7.78 (s, 1H), 7.51-7.49 (m, 2H), 7.37-7.36 (m, 2H), 7.22-7.20 (m, 3H), 2.60 (s, 3H).

Example 6

8-(7-Fluoro-1H-indazol-5-yl)-7-phenyl-[1,2,4]triazolo[4,3-c]pyrimidin-5-amine 6

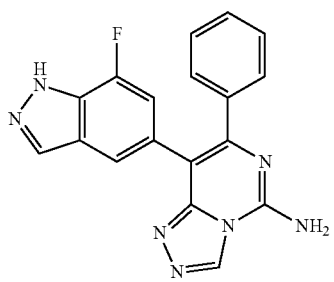
6a

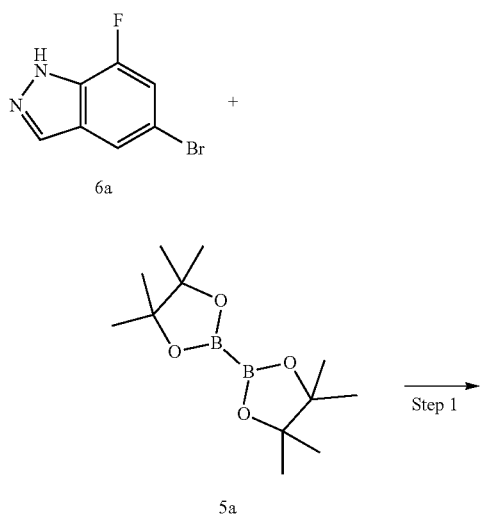
5a

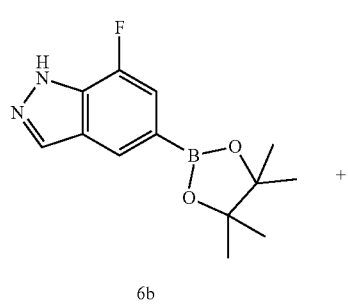
6b

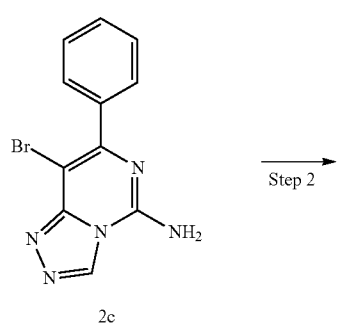
2c

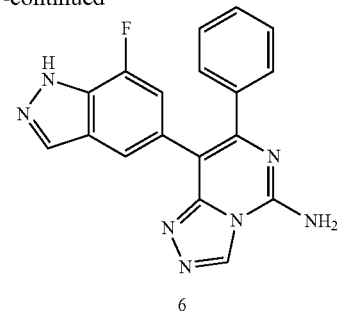
6

Step 1

7-Fluoro-5-(4,4,5,5-tetramethyl-1,3,2-dioxaborolan-2-yl)-1H-indazole 6b

5-Bromo-7-fluoro-1H-indazole 6a (1.27 g, 5.90 mmol, prepared according to the method disclosed in the patent application "WO2012037410"), compound 5a (2.25 g, 8.86 mmol), [1,1'-bis(diphenylphosphino)ferrocene]dichloropalladium (432 mg, 0.56 mmol) and potassium acetate (1.74 g, 17.7 mmol) were dissolved successively in 40 mL of glycol dimethyl ether under an argon atmosphere. The reaction solution was heated to 80° C., and stirred for 12 hours. The reaction was stopped. The reaction solution was cooled to room temperature, added with 10 mL of ethyl acetate, and filtrated. The filtrate was concentrated under reduced pressure, and the residue was purified by silica gel chromatography with eluent system B to obtain the title compound 6b (1.178 g, yield: 76.0%).

MS m/z (ESI): 263.2 [M+1]

Step 2

8-(7-Fluoro-1H-indazol-5-yl)-7-phenyl-[1,2,4]triazolo[4,3-c]pyrimidin-5-amine 6

Compound 2c (117 mg, 0.348 mmol), 6b (100 mg, 0.382 mmol), [1,1'-bis(diphenylphosphino)ferrocene]dichloropalladium (25 mg, 0.034 mmol) and potassium carbonate (192 mg, 1.387 mmol) were dissolved successively in 10 mL of a mixed solution of 1,4-dioxane and water (V/V=4:1) under an argon atmosphere. The reaction solution was heated to 90° C., and stirred for 2 hours. The reaction was stopped, and the reaction solution was added with 50 mL of water and extracted with ethyl acetate (30 mL×3). The organic phase was concentrated under reduced pressure, and the residue was purified by high performance liquid chromatography to obtain the title compound 6 (13 mg, yield: 10.8%).

MS m/z (ESI): 346.4 [M+1]

$^1$H NMR (400 MHz, DMSO-$d_6$) δ 13.65 (brs, 1H), 9.34 (s, 1H), 8.13-8.11 (m, 3H), 7.55 (s, 1H), 7.35-7.33 (m, 2H), 7.23-7.22 (m, 3H), 7.05-7.02 (m, 1H).

Example 7

8-(8-Fluoroquinolin-6-yl)-7-phenyl-[1,2,4]triazolo[4,3-c]pyrimidin-5-amine 7

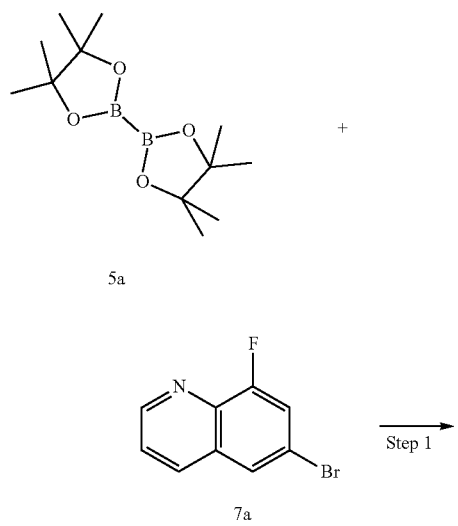

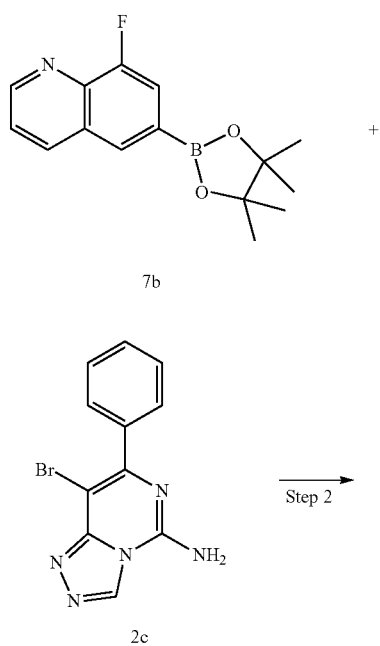

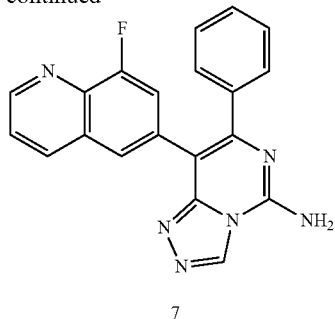

Step 1

8-Fluoro-6-(4,4,5,5-tetramethyl-1,3,2-dioxaborolan-2-yl)quinoline 7b

6-Bromo-8-fluoroquinoline 7a (226 mg, 1.00 mmol, prepared according to the known method disclosed in "*Journal of Medicinal Chemistry*, 2010, 53(10), 4066-4084"), compound 5a (305 mg, 1.20 mmol), [1,1'-bis(diphenylphosphino)ferrocene]dichloropalladium (146 mg, 0.20 mmol) and potassium acetate (294 mg, 3.00 mmol) were dissolved successively in 10 mL of glycol dimethyl ether under an argon atmosphere. The reaction solution was heated to 80° C., and stirred for 12 hours. The reaction was stopped, and the reaction solution was cooled to room temperature and filtrated. The filtrate was concentrated under reduced pressure, and the residue was purified by CombiFlash rapid preparation instrument with eluent system B to obtain the title compound 7b (220 mg, yield: 80.1%).

MS m/z (ESI): 274.1 [M+1]

Step 2

8-(8-Fluoroquinolin-6-yl)-7-phenyl-[1,2,4]triazolo[4,3-c]pyrimidin-5-amine 7

Compound 2c (100 mg, 0.345 mmol), 7b (100 mg, 0.414 mmol), [1,1'-bis(diphenylphosphino)ferrocene]dichloropalladium (25 mg, 0.034 mmol) and potassium carbonate (143 mg, 1.034 mmol) were dissolved successively in 6 mL of a mixed solution of 1,4-dioxane and water (V/V=5:1) under an argon atmosphere. The reaction solution was heated to 90° C., and stirred for 3 hours. The reaction was stopped, and the reaction solution was added with 50 mL of water and extracted with ethyl acetate (40 mL×4). The organic phase was concentrated under reduced pressure, and the residue was purified by high performance liquid chromatography to obtain the title compound 7 (20 mg, yield: 16.3%).

MS m/z (ESI): 357.2 [M+1]

$^1$H NMR (400 MHz, DMSO-d$_6$) δ 9.38 (s, 1H), 8.94-8.93 (m, 1H), 8.35-8.33 (m, 1H), 8.26 (brs, 2H), 7.86 (s, 1H), 7.62-7.59 (m, 1H), 7.40-7.36 (m, 3H), 7.26-7.24 (m, 3H).

Example 8

8-(2-Methyl-6-(trifluoromethyl)pyridin-4-yl)-7-(5-methylfuran-2-yl)-[1,2,4]triazolo[4,3-c]pyrimidin-5-amine 8

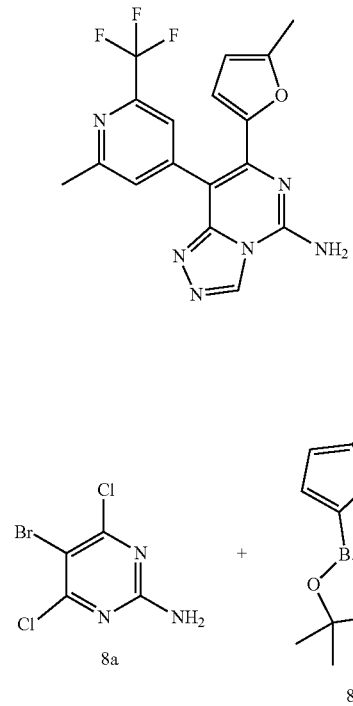

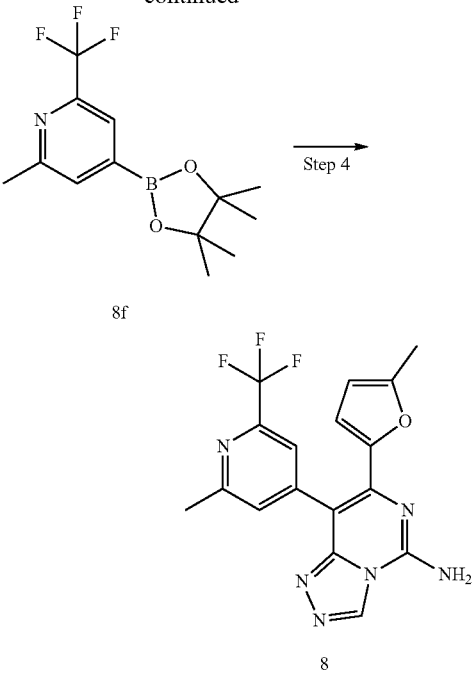

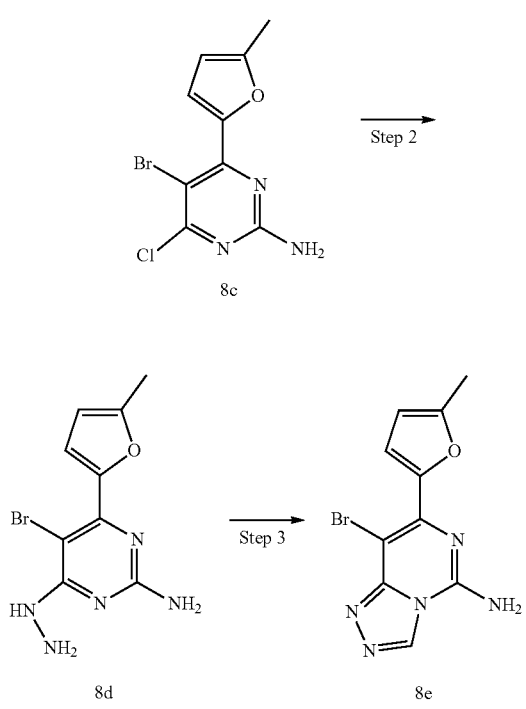

Step 1

5-Bromo-4-chloro-6-(5-methylfuran-2-yl)pyrimidin-2-amine 8c

5-Bromo-4,6-dichloropyrimidin-2-amine 8a (5 g, 20.585 mmol, prepared according to the method disclosed in the patent application "U520100331294"), 4,4,5,5-tetramethyl-2-(5-methylfuran-2-yl)-1,3,2-dioxaborolane 8b (4.283 g, 20.585 mmol, prepared according to the known method disclosed in "Organometallics, 2015, 34(7), 1307-1320"), [1,1'-bis(diphenylphosphino)ferrocene]dichloropalladium (1.506 g, 2.058 mmol) and potassium carbonate (8.535 g, 61.756 mmol) were dissolved successively in 150 mL of a mixed solution of 1,4-dioxane and water (V/V=4:1) under an argon atmosphere, and stirred for 2 hours. The reaction was stopped, and the reaction solution was added with 200 mL of water and extracted with ethyl acetate (200×3). The organic phase was added with 100 to 200 mesh silicon dioxide, and concentrated under reduced pressure. The residue was purified by CombiFlash rapid preparation instrument with eluent system B to obtain the title compound 8c (2.0 g, yield: 33.7%).

MS m/z (ESI): 288.2 [M+1]

Step 2

5-Bromo-4-hydrazinyl-6-(5-methylfuran-2-yl)pyrimidin-2-amine 8d

Compound 8c (1.88 g, 6.516 mmol) and 15 mL of 85% hydrazine hydrate were dissolved successively in 120 mL of ethanol. The reaction solution was stirred for 17 hours. The reaction was stopped, and the reaction solution was filtrated. The filter cake was dried to obtain the crude title compound 8d (1.5 g), which was used directly in the next step without purification.

MS m/z (ESI): 284.3 [M+1]

Step 3

8-Bromo-7-(5-methylfuran-2-yl)-[1,2,4]triazolo[4,3-c]pyrimidin-5-amine 8e

The crude product 8d (1.5 g, 5.279 mmol) was added to 20 mL of (tri)ethyl orthoformate. The reaction solution was stirred at 140° C. for 15 minutes. The reaction was stopped, and the reaction solution was cooled to room temperature and filtrated. The filter cake was washed with n-hexane (20 mL×2), and dried to obtain the crude title compound 8e (1.13 g, yield: 72.8%).

MS m/z (ESI): 294.3 [M+1]

Step 4

8-(2-Methyl-6-(trifluoromethyl)pyridin-4-yl)-7-(5-methylfuran-2-yl)-[1,2,4]triazolo[4,3-c]pyrimidin-5-amine 8

The crude product 8e (140 mg, 0.476 mmol), 2-methyl-4-(4,4,5,5-tetramethyl-1,3,2-dioxaborolan-2-yl)-6-(trifluoromethyl)pyridine 8f (205 mg, 0.714 mmol, prepared according to the known method disclosed in "*Journal of Medicinal Chemistry* 2012, 55(5), 1898-1903"), [1,1'-bis(diphenylphosphino)ferrocene]dichloropalladium (35 mg, 0.048 mmol) and potassium carbonate (197 mg, 1.428 mmol) were dissolved successively in 6 mL of a mixed solution of 1,4-dioxane and water (V/V=5:1) under an argon atmosphere. The reaction solution was heated to 90° C., and stirred for 2.5 hours. The reaction was stopped, and the reaction solution was added with 50 mL of water and extracted with ethyl acetate (50 mL×3). The organic phase was concentrated under reduced pressure, and the residue was purified by high performance liquid chromatography to obtain the title compound 8 (80 mg, yield: 44.9%).

MS m/z (ESI): 375.4 [M+1]

$^1$H NMR (400 MHz, DMSO-d$_6$) δ 9.30 (s, 1H), 8.26 (brs, 2H), 7.68 (s, 1H), 7.64 (s, 1H), 6.70-6.69 (m, 1H), 6.20-6.19 (m, 1H), 2.60 (s, 3H), 2.03 (s, 3H).

Example 9

7-Phenyl-8-(7-(trifluoromethyl)-1H-indazol-5-yl)-[1,2,4]triazolo[4,3-c]pyrimidin-5-amine 9

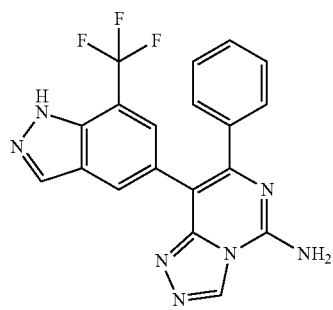

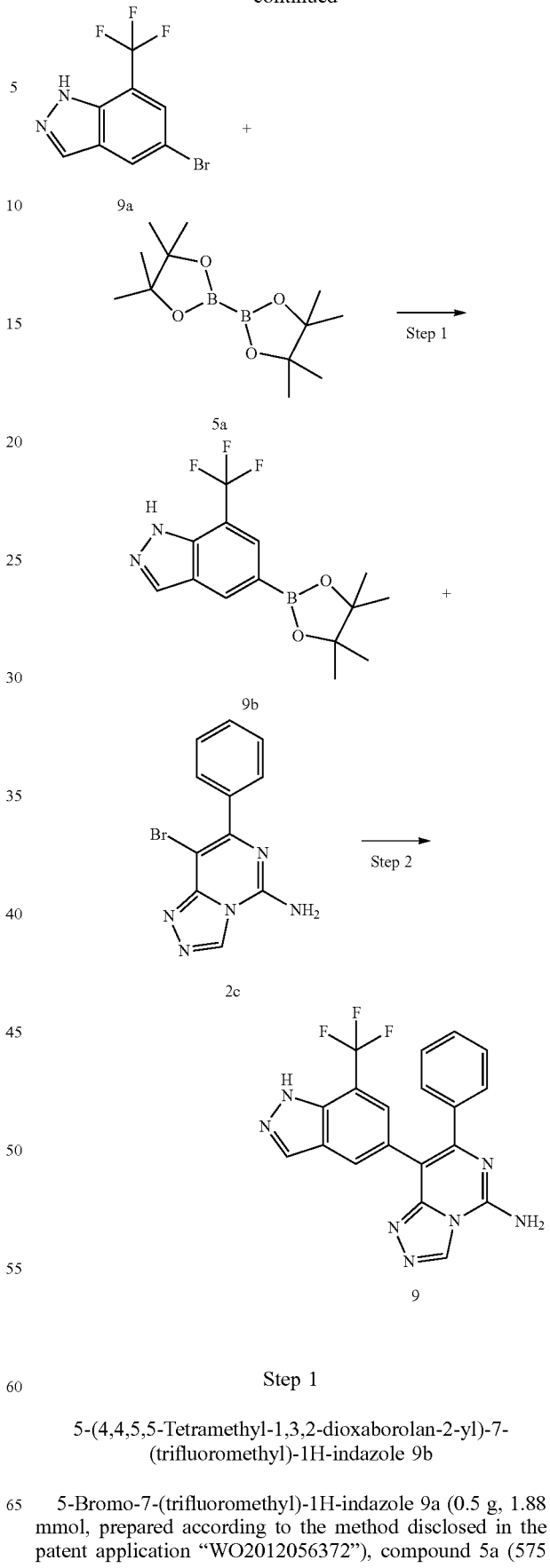

Step 1

5-(4,4,5,5-Tetramethyl-1,3,2-dioxaborolan-2-yl)-7-(trifluoromethyl)-1H-indazole 9b 5-Bromo-7-(trifluoromethyl)-1H-indazole 9a (0.5 g, 1.88 mmol, prepared according to the method disclosed in the patent application "WO2012056372"), compound 5a (575 mg, 2.26 mmol), [1,1'-bis(diphenylphosphino)ferrocene]dichloropalladium (275 mg, 0.38 mmol) and potassium acetate (554 mg, 5.66 mmol) were dissolved successively in 10 mL of glycol dimethyl ether under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with eluent system C to obtain the title compound 9b (270 mg, yield: 45.9%).

MS m/z (ESI): 313.2 [M+1]

Step 2

7-Phenyl-8-(7-(trifluoromethyl)-1H-indazol-5-yl)-[1,2,4]triazolo[4,3-c]pyrimidin-5-amine 9

Compound 2c (117 mg, 0.348 mmol), 9b (35 mg, 0.11 mmol), [1,1'-bis(diphenylphosphino)ferrocene]dichloropalladium (25 mg, 0.035 mmol) and potassium carbonate (192 mg, 1.387 mmol) were dissolved successively in 5 mL of a mixed solution of 1,4-dioxane and water (V/V=4:1) under an argon atmosphere. The reaction solution was heated to 90° C., and stirred for 2 hours. The reaction was stopped, and the reaction solution was added with 10 mL of water and extracted with a mixed solution of dichloromethane and methanol (V/V=8:1) (20 mL×3). The organic phase was concentrated under reduced pressure, and the residue was purified by high performance liquid chromatography to obtain the title compound 6 (10 mg, yield: 22%).

MS m/z (ESI): 396.4 [M+1]

$^1$H NMR (400 MHz, DMSO-d$_6$) δ 13.66 (s, 1H), 9.36 (s, 1H), 8.25-8.09 (m, 4H), 7.53 (s, 1H), 7.33-7.31 (m, 2H), 7.25-7.23 (m, 3H).

Example 10

8-(1H-indazol-5-yl)-7-phenyl-[1,2,4]triazolo[4,3-c]pyrimidin-5-amine 10

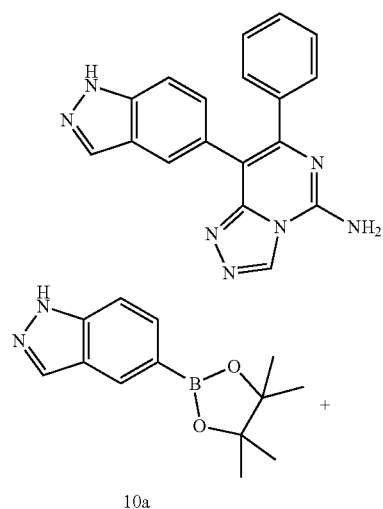

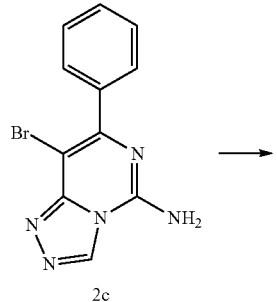

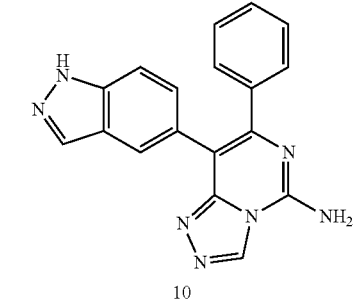

Compound 2c (140 mg, 0.482 mmol), 5-(4,4,5,5-tetramethyl-1,3,2-dioxaborolan-2-yl)-1H-indazole 10a (141 mg, 0.579 mmol, prepared according to the known method disclosed in "*Journal of Medicinal Chemistry*, 2014, 57(9), 3856-3873"), [1,1'-bis(diphenylphosphino)ferrocene]dichloropalladium (35 mg, 0.048 mmol) and potassium carbonate (200 mg, 1.448 mmol) were dissolved successively in 12 mL of a mixed solution of 1,4-dioxane and water (V/V=5:1) under an argon atmosphere. The reaction solution was heated to 90° C., and stirred for 3 hours. The reaction was stopped, and the reaction solution was added with 50 mL of water and extracted with a mixed solution of dichloromethane and water (V/V=8:1) (30 mL×3). The organic phase was concentrated under reduced pressure, and the residue was purified by high performance liquid chromatography to obtain the title compound 10 (8.6 mg, yield: 5.4%).

MS m/z (ESI): 328.1 [M+1]

$^1$H NMR (400 MHz, DMSO-d$_6$) δ 13.05 (brs, 1H), 9.33 (s, 1H), 8.05-8.01 (m, 3H), 7.75 (s, 1H), 7.53-7.41 (m, 1H), 7.35-7.33 (m, 2H), 7.20-7.07 (m, 4H).

Example 11

8-(2,6-Dimethylpyridin-4-yl)-7-phenyl-[1,2,4]triazolo[4,3-c]pyrimidin-5-amine 11

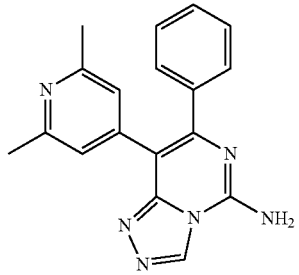

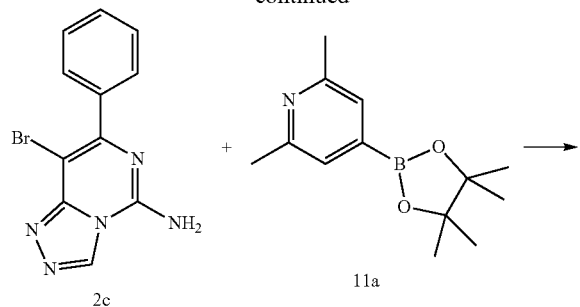

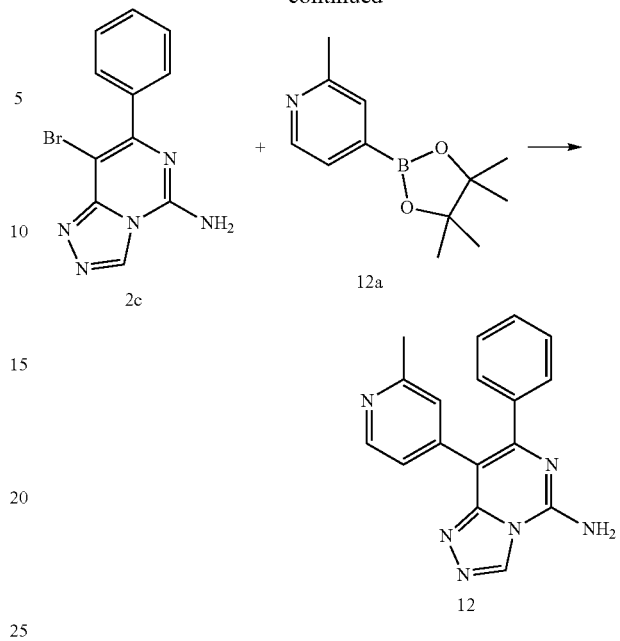

Compound 2c (100 mg, 0.345 mmol), 2,6-dimethyl-4-(4,4,5,5-tetramethyl-1,3,2-dioxaborolan-2-yl)pyridine 11a (91 mg, 0.414 mmol, prepared according to the known method disclosed in "*Organic Letters,* 2009, 11(16), 3586-3589"), [1,1'-bis(diphenylphosphino)ferrocene]dichloropalladium (25 mg, 0.034 mmol) and potassium carbonate (143 mg, 1.034 mmol) were dissolved successively in 6 mL of a mixed solution of 1,4-dioxane and water (V/V=5:1) under an argon atmosphere. The reaction solution was heated to 90° C., and stirred for 3 hours. The reaction was stopped, and the reaction solution was added with 50 mL of water and extracted with ethyl acetate (30 mL×3). The organic phase was concentrated under reduced pressure, and the residue was purified by high performance liquid chromatography to obtain the title compound 11 (27 mg, yield: 24.8%).

MS m/z (ESI): 317.5 [M+1]

¹H NMR (400 MHz, DMSO-$d_6$) δ 9.35 (s, 1H), 8.25 (brs, 2H), 7.32-7.30 (m, 5H), 6.97 (s, 2H), 2.32 (s, 6H).

Compound 2c (100 mg, 0.345 mmol), 2-methyl-4-(4,4,5,5-tetramethyl-1,3,2-dioxaborolan-2-yl)pyridine 12a (91 mg, 0.414 mmol, prepared according to the known method disclosed in "*Journal of the American Chemical Society,* 2014, 136(11), 4133-4136"), [1,1'-bis(diphenylphosphino)ferrocene]dichloropalladium (25 mg, 0.034 mmol) and potassium carbonate (143 mg, 1.034 mmol) were dissolved successively in 6 mL of a mixed solution of 1,4-dioxane and water (V/V=5:1) under an argon atmosphere. The reaction solution was heated to 90° C., and stirred for 3 hours. The reaction was stopped, and the reaction solution was added with 50 mL of water and extracted with ethyl acetate (30 mL×3). The organic phase was concentrated under reduced pressure, and the residue was purified by high performance liquid chromatography to obtain the title compound 12 (6.8 mg, yield: 6.5%).

MS m/z (ESI): 303.4 [M+1]

¹H NMR (400 MHz, DMSO-$d_6$) δ 9.35 (s, 1H), 8.29-8.26 (m, 3H), 7.32-7.25 (m, 6H), 6.99 (s, 1H), 2.39 (s, 3H).

Example 12

8-(2-Methylpyridin-4-yl)-7-phenyl-[1,2,4]triazolo[4,3-c]pyrimidin-5-amine 12

Example 13

5-Amino-7-phenyl-[1,2,4]triazolo[4,3-c]pyrimidine-8-carbonitrile 13

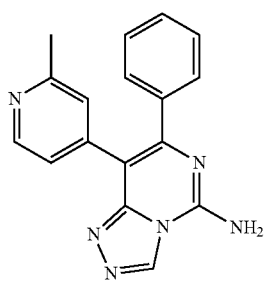

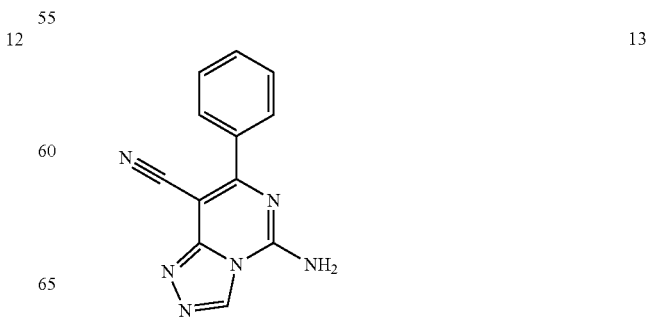

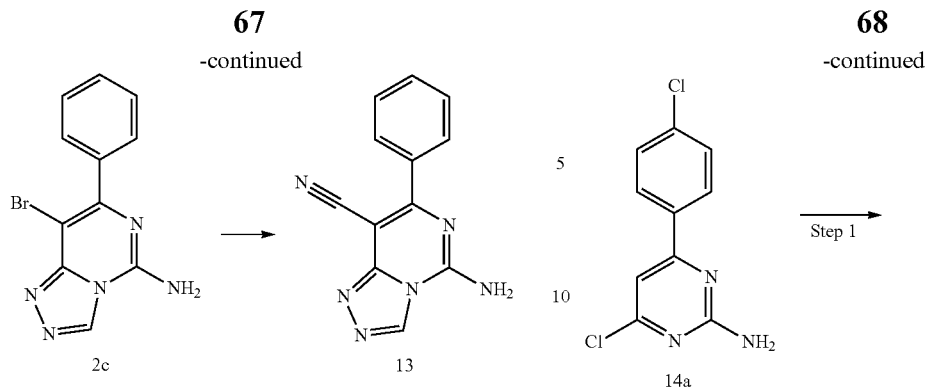

Compound 2c (1.0 g, 3.45 mmol), zinc cyanide (484 mg, 4.13 mmol), zinc (22 mg, 0.34 mmol), [1,1'-bis(diphenylphosphino)ferrocene]dichloropalladium (124 mg, 0.17 mmol) and tris(dibenzylideneacetone)dipalladium (156 mg, 0.17 mmol) were dissolved in 30 mL of N,N-dimethylformamide under an argon atmosphere, and stirred at 60° C. for 12 hours. After completion of the reaction, the reaction solution was filtrated through celite, and the filter cake was washed with methanol. The filtrate was added with 30 mL of water, and extracted with a mixed solution of dichloromethane and methanol (V/V=8:1) (30 mL×3). The organic phases were combined, washed with saturated sodium chloride solution, dried over anhydrous sodium sulfate, and filtrated. The filtrate was concentrated under reduced pressure, and the residue was purified by silica gel column chromatography with eluent system A to obtain the title compound 13 (650 mg, yield: 80.0%).

MS m/z (ESI): 237.0 [M+1]

$^1$H NMR (400 MHz, DMSO-$d_6$) δ 9.24 (brs, 1H), 8.83 (brs, 1H), 8.64 (s, 1H), 7.92-7.89 (m, 2H), 7.59-7.57 (m, 3H).

Example 14

7-(4-Chlorophenyl)-8-(2-methyl-6-(trifluoromethyl) pyridin-4-yl)-[1,2,4]triazolo[4,3-c]pyrimidin-5-amine 14

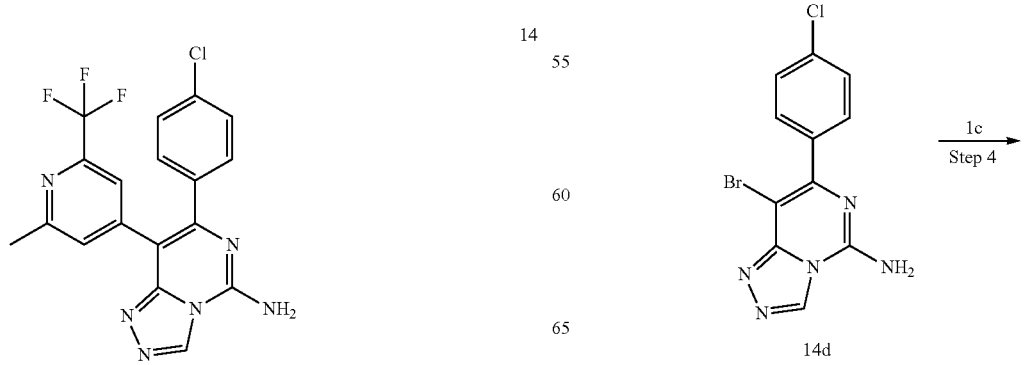

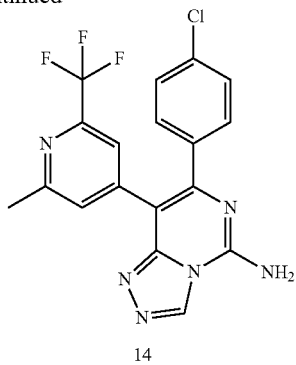

14

Step 1

5-Bromo-4-chloro-6-(4-chlorophenyl)pyrimidin-2-amine 14b

4-Chloro-6-(4-chlorophenyl)pyrimidin-2-amine 14a (11 g, 38.03 mmol, prepared according to the method disclosed in the patent application "DE102006008880A1") and N-bromosuccinimide (7.11 g, 39.93 mmol) were dissolved in 300 mL of N,N-dimethylformamide. After completion of the addition, the reaction solution was stirred for 2 hours. The reaction solution was added with 1 L of water, and extracted with ethyl acetate (300 mL×4). The organic phases were combined, washed with water (100 mL×3) and saturated sodium chloride solution (200 mL×2) successively, dried over anhydrous sodium sulfate, and filtrated to collect the filtrate. The filtrate was concentrated under reduced pressure to obtain the crude title compound 14b (12 g), which was used directly in the next step without purification.

MS m/z (ESI): 318.2 [M+1]

Step 2

5-Bromo-4-(4-chlorophenyl)-6-hydrazinylpyrimidin-2-amine 14c

The crude compound 14b (12 g, 37.62 mmol) and 40 mL of 85% hydrazine hydrate were dissolved successively in 400 mL of ethanol. The reaction solution was stirred for 17 hours. The reaction solution was filtrated, and the filter cake was washed with ethanol (50 mL) and n-hexane (100 mL×2) successively. The filter cake was collected and dried to obtain the crude title compound 14c (10.28 g), which was used directly in the next step without purification.

MS m/z (ESI): 314.3 [M+1]

Step 3

8-Bromo-7-(4-chlorophenyl)-[1,2,4]triazolo[4,3-c]pyrimidin-5-amine 14d

The crude compound 14c (2 g, 6.36 mmol) and 1.16 mL of (tri)ethyl orthoformate (1.04 g, 6.99 mmol) were added to 50 mL of ethanol. The reaction solution was stirred under reflux for 4 hours. The reaction solution was cooled to room temperature, and concentrated under reduced pressure. The residue was added with 51 mL of a mixed solution of ethanol and n-hexane (V/V=1:50), stirred and filtrated. The filter cake was collected to obtain the title compound 14d (2 g, yield: 96.9%).

MS m/z (ESI): 324.3 [M+1]

Step 4

7-(4-Chlorophenyl)-8-(2-methyl-6-(trifluoromethyl) pyridin-4-yl)-[1,2,4]triazolo[4,3-c]pyrimidin-5-amine 14

Compound 14d (250 mg, 770.27 μmop, compound 1c (265.36 mg, 924.32 μmop, [1,1'-bis(diphenylphosphino)ferrocene]dichloropalladium (56.36 mg, 77.03 μmol) and potassium carbonate (319.36 mg, 2.31 mmol) were added successively to 10 mL of a mixed solution of 1,4-dioxane and water (V/V=4:1) under an argon atmosphere. The reaction solution was heated to 90° C., and stirred for 2 hours. The reaction solution was cooled to room temperature, and concentrated under reduced pressure. The residue was purified by CombiFlash rapid preparation instrument with eluent system B. The resulting crude product was purified by high performance liquid chromatography (Waters 2767-SQ Detecor2, elution system: ammonium bicarbonate, water, acetonitrile) to obtain the title compound 14 (64.4 mg, yield: 20.7%).

MS m/z (ESI): 405.5 [M+1]

$^1$H NMR (400 MHz, DMSO-d$_6$) δ 9.39 (s, 1H), 8.46 (brs, 2H), 7.58 (s, 1H), 7.49 (s, 1H), 7.43-7.35 (m, 4H), 2.50 (s, 3H).

Example 15

8-(2-Chloro-6-methylpyridin-4-yl)-7-(4-fluorophenyl)-[1,2,4]triazolo[4,3-c]pyrimidin-5-amine 15

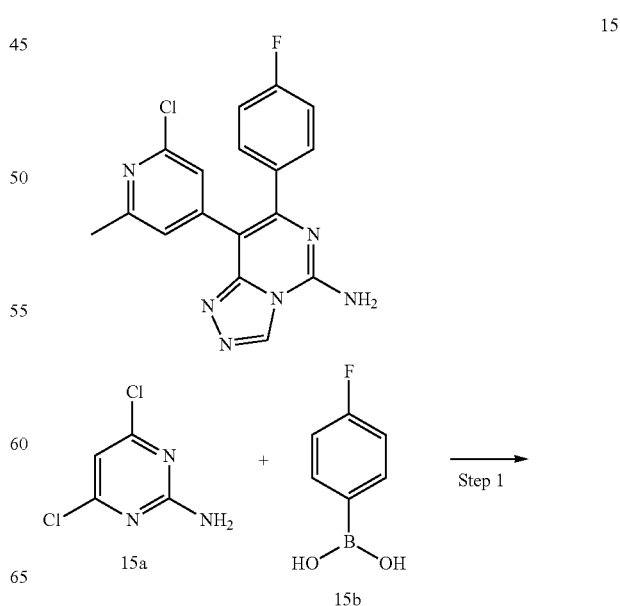

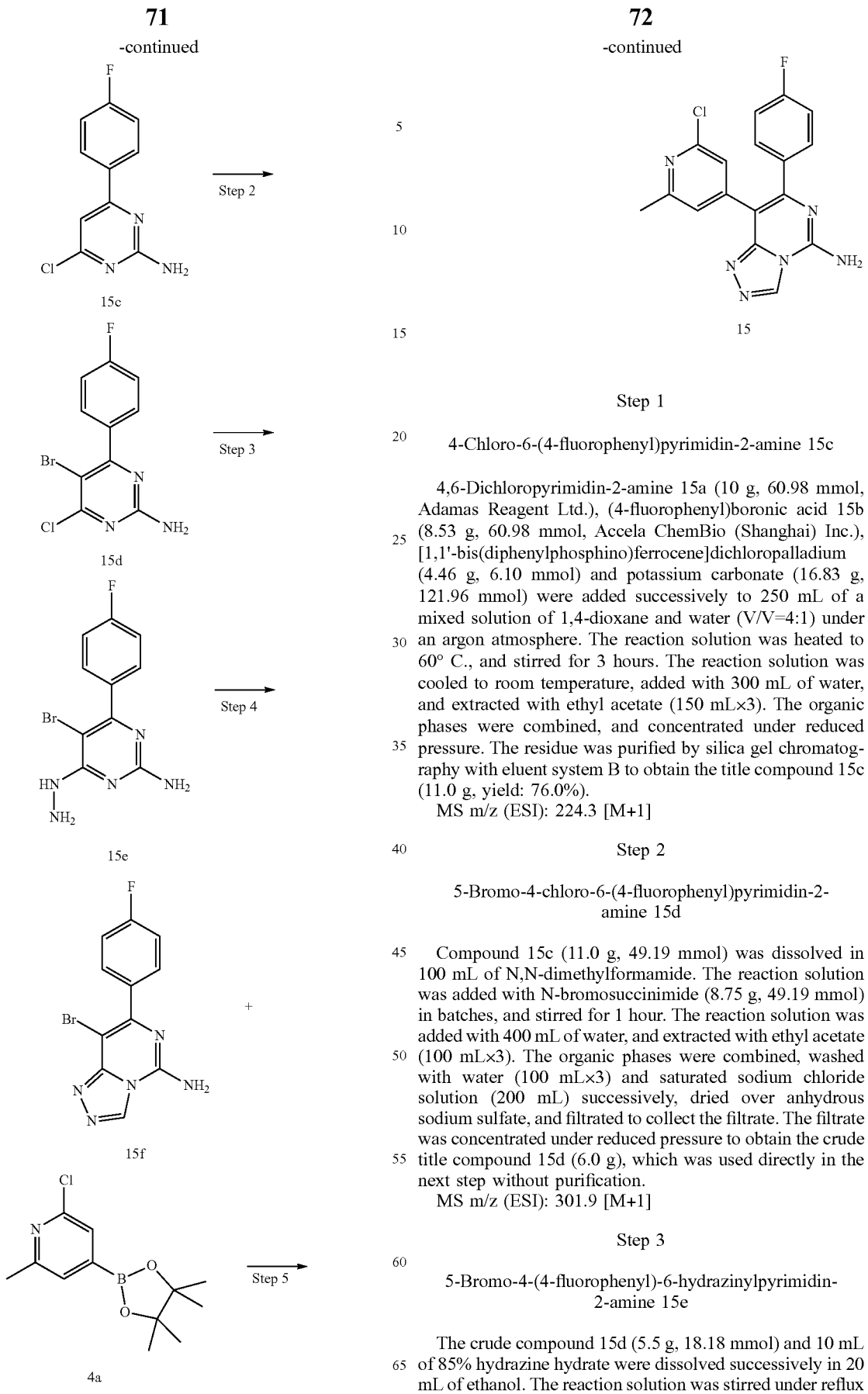

Step 1

4-Chloro-6-(4-fluorophenyl)pyrimidin-2-amine 15c 4,6-Dichloropyrimidin-2-amine 15a (10 g, 60.98 mmol, Adamas Reagent Ltd.), (4-fluorophenyl)boronic acid 15b (8.53 g, 60.98 mmol, Accela ChemBio (Shanghai) Inc.), [1,1'-bis(diphenylphosphino)ferrocene]dichloropalladium (4.46 g, 6.10 mmol) and potassium carbonate (16.83 g, 121.96 mmol) were added successively to 250 mL of a mixed solution of 1,4-dioxane and water (V/V=4:1) under an argon atmosphere. The reaction solution was heated to 60° C., and stirred for 3 hours. The reaction solution was cooled to room temperature, added with 300 mL of water, and extracted with ethyl acetate (150 mL×3). The organic phases were combined, and concentrated under reduced pressure. The residue was purified by silica gel chromatography with eluent system B to obtain the title compound 15c (11.0 g, yield: 76.0%).

MS m/z (ESI): 224.3 [M+1]

Step 2

5-Bromo-4-chloro-6-(4-fluorophenyl)pyrimidin-2-amine 15d

Compound 15c (11.0 g, 49.19 mmol) was dissolved in 100 mL of N,N-dimethylformamide. The reaction solution was added with N-bromosuccinimide (8.75 g, 49.19 mmol) in batches, and stirred for 1 hour. The reaction solution was added with 400 mL of water, and extracted with ethyl acetate (100 mL×3). The organic phases were combined, washed with water (100 mL×3) and saturated sodium chloride solution (200 mL) successively, dried over anhydrous sodium sulfate, and filtrated to collect the filtrate. The filtrate was concentrated under reduced pressure to obtain the crude title compound 15d (6.0 g), which was used directly in the next step without purification.

MS m/z (ESI): 301.9 [M+1]

Step 3

5-Bromo-4-(4-fluorophenyl)-6-hydrazinylpyrimidin-2-amine 15e

The crude compound 15d (5.5 g, 18.18 mmol) and 10 mL of 85% hydrazine hydrate were dissolved successively in 20 mL of ethanol. The reaction solution was stirred under reflux for 1 hour. The reaction solution was cooled to room temperature, and stirred for 0.5 hour. The reaction solution was filtrated, and the filter cake was washed with ethanol (3 mL×2) and diethyl ether (3 mL×2) successively. The filter cake was collected, and dried in vacuum to obtain the crude title compound 15e (4.4 g), which was used directly in the next step without purification.

MS m/z (ESI): 298.1 [M+1]

Step 4

8-Bromo-7-(4-fluorophenyl)-[1,2,4]triazolo[4,3-c] pyrimidin-5-amine 15f

The crude compound 15e (500 mg, 1.68 mmol) and (tri)ethyl orthoformate (497 mg, 3.35 mmol) were added successively to 20 mL of ethanol. The reaction solution was heated to reflux for 3 hours. The reaction solution was cooled to room temperature and filtrated. The filter cake was washed with 2 mL of ethanol once, and then collected to obtain the crude title compound 15f (460 mg), which was used directly in the next step without purification.

MS m/z (ESI): 307.9 [M+1]

Step 5

8-(2-Chloro-6-methylpyridin-4-yl)-7-(4-fluorophenyl)-[1,2,4]triazolo[4,3-c]pyrimidin-5-amine 15

The crude compound 15f (120 mg, 389.47 µmol), compound 4a (138.24 mg, 545.26 µmol), [1,1'-bis(diphenylphosphino)ferrocene]dichloropalladium (28.50 mg, 38.95 µmol) and potassium carbonate (161.48 mg, 1.17 mmol) were added successively to 6.0 mL of a mixed solution of 1,4-dioxane and water (V/V=5:1) under an argon atmosphere. The reaction solution was heated to 90° C., and stirred for 2 hours. The reaction solution was cooled to room temperature, added with 50 mL of water, and extracted with ethyl acetate (30 mL×3). The organic phases were combined, and concentrated under reduced pressure. The residue was purified by high performance liquid chromatography (Waters 2767-SQ Detecor2, elution system: ammonium bicarbonate, water, acetonitrile) to obtain the title compound 15 (22 mg, yield: 15.9%).

MS m/z (ESI): 355.1 [M+1]

$^1$H NMR (400 MHz, DMSO-d$_6$) δ 9.35 (s, 1H), 8.38 (brs, 2H), 7.40-7.37 (m, 2H), 7.20-7.18 (m, 4H), 2.37 (s, 3H).

Example 16

7-(4-Fluorophenyl)-8-(2-methyl-6-(trifluoromethyl) pyridin-4-yl)-[1,2,4]triazolo[4,3-c]pyrimidin-5-amine 16

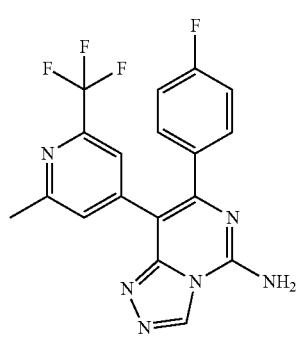

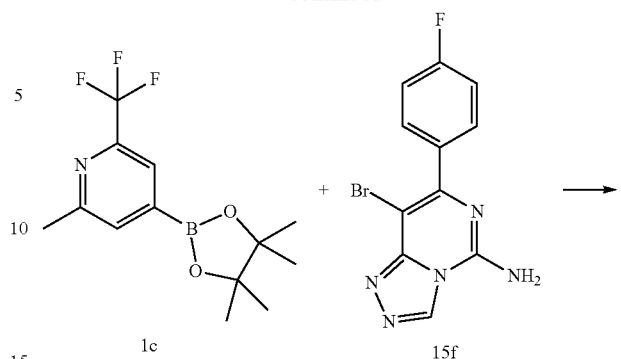

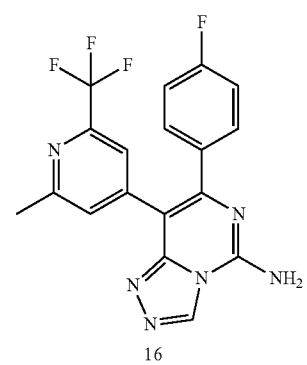

Compound 15f (100 mg, 324.56 µmol), compound 1c (111.81 mg, 389.47 µmol), [1,1'-bis(diphenylphosphino)ferrocene]dichloropalladium (23.73 mg, 32.46 µmol) and potassium carbonate (89.71 mg, 649.12 µmol) were added successively to 6.0 mL of a mixed solution of 1,4-dioxane and water (V/V=5:1) under an argon atmosphere. The reaction solution was heated to 90° C., and stirred for 2 hours. The reaction solution was cooled to room temperature, added with 20 mL of water, and extracted with ethyl acetate (10 mL×3). The organic phases were combined, and concentrated under reduced pressure. The residue was purified by high performance liquid chromatography (Waters 2767-SQ Detecor2, elution system: ammonium bicarbonate, water, acetonitrile) to obtain the title compound 16 (34 mg, yield: 26.9%).

MS m/z (ESI): 389.4 [M+1]

$^1$H NMR (400 MHz, DMSO-d$_6$) δ 9.35 (s, 1H), 8.40 (brs, 2H), 7.56 (s, 1H), 7.43 (s, 1H), 7.34-7.37 (m, 2H), 7.13-7.17 (m, 2H), 2.49 (s, 3H).

Example 17

8-(2-Methyl-6-(trifluoromethyl)pyridin-4-yl)-7-phenylimidazo[1,2-c]pyrimidin-5-amine

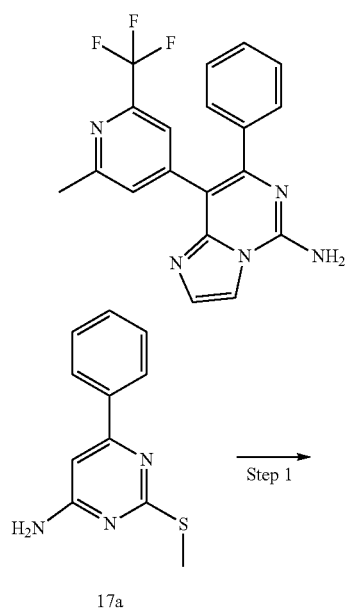

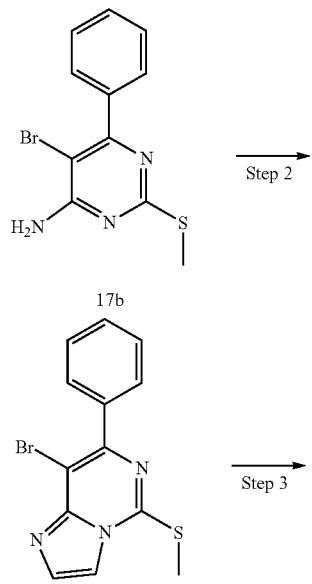

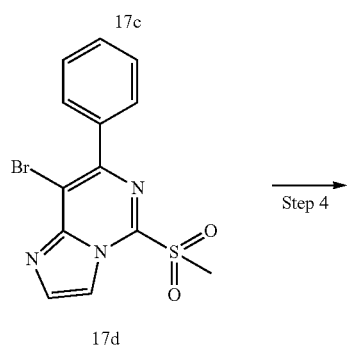

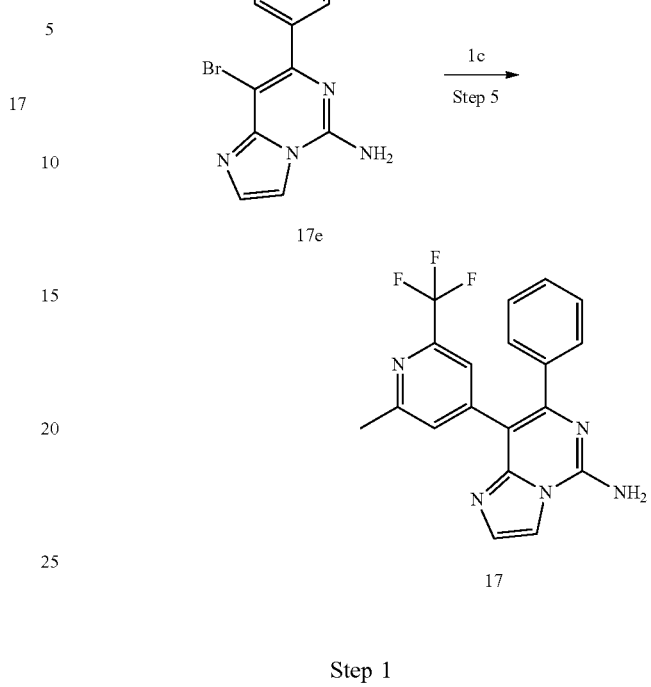

Step 1

5-Bromo-2-(methylthio)-6-phenylpyrimidin-4-amine 17b 2-(Methylthio)-6-phenylpyrimidin-4-amine 17a (1.2 g, 5.5 mmol, prepared according to the known method disclosed in "Chemical & Pharmaceutical Bulletin, 1981, 29(4), 948-54") and N-bromosuccinimide (1.1 g, 6.1 mmol) were added successively to 20 mL of N,N-dimethylformamide. The reaction solution was stirred for 1 hour. The reaction solution was added with water, and extracted with ethyl acetate three times. The organic phases were combined, washed with saturated sodium chloride solution, dried over anhydrous sodium sulfate, and filtrated. The filtrate was concentrated under reduced pressure to obtain the crude title compound 17b (550 mg), which was used directly in the next step without purification.

MS m/z (ESI): 296.0 [M+1]

Step 2

8-Bromo-5-(methylthio)-7-phenymidazo[1,2-c]pyrimidine 17c

The crude compound 17b (250 mg, 0.84 mmol) was dissolved in 10 mL of 1,4-dioxane. The reaction solution was added dropwise with chloroacetaldehyde (249 mg, 1.27 mmol), and stirred at 90° C. for 36 hours. The reaction solution was cooled to room temperature, added with saturated sodium bicarbonate solution, and extracted with ethyl acetate three times. The organic phases were combined, washed with saturated sodium chloride solution, dried over anhydrous sodium sulfate, and filtrated. The filtrate was concentrated under reduced pressure, and the residue was purified by thin layer chromatography with developing solvent system A to obtain the title compound 17c (195 mg, yield: 72%).

MS m/z (ESI): 320.1 [M+1]

Step 3

8-Bromo-5-(methylsulfonyl)-7-phenylimidazo[1,2-c]pyrimidine 17d

Compound 17c (195 mg, 0.61 mmol) was dissolved in 10 mL of dichloromethane. The reaction solution was added with m-chloroperoxybenzoic acid (316 mg, 1.83 mmol) in batches, and stirred for 3 hours. The reaction solution was added with saturated sodium bicarbonate solution, and extracted with ethyl acetate three times. The organic phases were combined, washed with saturated sodium chloride solution, dried over anhydrous sodium sulfate, and filtrated. The filtrate was concentrated under reduced pressure to obtain the crude title compound 17d (210 mg), which was used directly in the next step without purification.

MS m/z (ESI): 352.1 [M+1]

Step 4

8-Bromo-7-phenylimidazo[1,2-c]pyrimidin-5-amine 17e

The crude compound 17d (210 mg, 0.59 mmol) was dissolved in 10 mL of 1,4-dioxane. The reaction solution was added dropwise with 1 mL of 30% ammonia, and stirred for 1 hour. The reaction solution was added with water, and extracted with a mixed solution of dichloromethane and methanol (V/V=10:1) three times. The organic phases were combined, washed with saturated sodium chloride solution, dried over anhydrous sodium sulfate, and filtrated. The filtrate was concentrated under reduced pressure, and the residue was purified by thin layer chromatography with developing solvent system A to obtain the title compound 17e (172 mg, yield: 46%).

MS m/z (ESI): 289.1 [M+1]

Step 5

8-(2-Methyl-6-(trifluoromethyl)pyridin-4-yl)-7-phenylimidazo[1,2-c]pyrimidin-5-amine 17

Compound 17e (80 mg, 0.28 mmol), compound 1c (95 mg, 0.332 mmol), [1,1'-bis(diphenylphosphino)ferrocene]dichloropalladium (20 mg, 28 μmol) and potassium carbonate (87 mg, 0.56 mmol) were added successively to 10 mL of a mixed solution of 1,4-dioxane and water (V/V=4:1) under an argon atmosphere. The reaction solution was heated to 90° C., and stirred for 3 hours. The reaction solution was cooled to room temperature, added with water, and extracted with a mixed solution of dichloromethane and methanol (V/V=8:1) three times. The organic phases were combined, washed with saturated sodium chloride solution, dried over anhydrous sodium sulfate, and filtrated. The filtrate was concentrated under reduced pressure, and the residue was purified by thin layer chromatography with developing solvent system A to obtain the title compound 17 (15 mg, yield: 14%).

MS m/z (ESI): 370.1 [M+1]

$^1$H NMR (400 MHz, DMSO-d$_6$) δ 8.02 (s, 1H), 7.99 (brs, 2H), 7.57 (s, 1H), 7.55 (s, 1H), 7.43 (s, 1H), 7.30 (brs, 5H), 2.45 (s, 3H).

Example 18

7-(2,4-Difluorophenyl)-8-(2-methyl-6-(trifluoromethyl)pyridin-4-yl)-[1,2,4]triazolo[4,3-c]pyrimidin-5-amine 18

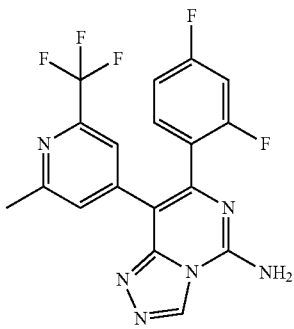

18

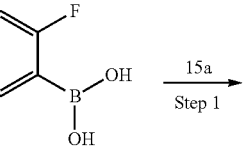

18a

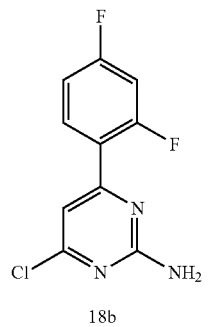

18b

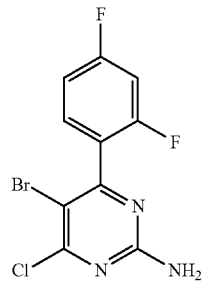

18c

79

-continued

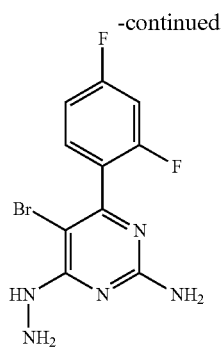

18d

↓ Step 5, 1c

18e

18

Step 1

4-Chloro-6-(2,4-difluorophenyl)pyrimidin-2-amine 18b

Compound 15a (11 g, 63.72 mmol), (2,4-difluorophenyl)boronic acid 18a (10.06 g, 63.72 mmol, Shanghai Bepharm Ltd.), [1,1'-bis(diphenylphosphino)ferrocene]dichloropalladium (4.66 g, 6.37 mmol) and potassium carbonate (26.42 g, 191.17 mmol) were added successively to 500 mL of a mixed solution of 1,4-dioxane and water (V/V=4:1) under an argon atmosphere. The reaction solution was heated to 90° C., and stirred for 2 hours. The reaction solution was filtrated, and the filtrate was separated into two phases. The aqueous phase was extracted with ethyl acetate (200 mL×2). The organic phases were combined, and concentrated under reduced pressure. The residue was purified by silica gel chromatography with eluent system B to obtain the title compound 18b (14.04 g, yield: 91.2%).

MS m/z (ESI): 242.3 [M+1]

80

Step 2

5-Bromo-4-chloro-6-(2,4-difluorophenyl)pyrimidin-2-amine 18c

Compound 18b (14.04 g, 58.11 mmol) was dissolved in 300 mL of N,N-dimethylformamide. The reaction solution was added with N-bromosuccinimide (11.38 g, 63.92 mmol), and stirred for 1 hour. The reaction solution was poured into 1 L of water, stirred for 30 minutes, and filtrated. The filter cake was collected, and dried in vacuum to obtain the crude title compound 18c (16 g), which was used directly in the next step without purification.

MS m/z (ESI): 320.0 [M+1]

Step 3

5-Bromo-4-(2,4-difluorophenyl)-6-hydrazinylpyrimidin-2-amine 18d

The crude compound 18c (16 g, 49.92 mmol) was dissolved in 250 mL of ethanol. The reaction solution was added with 50 mL of 85% hydrazine hydrate, and stirred for 17 hours. The reaction solution was filtrated. The filter cake was washed with ethanol (20 mL×2) and n-hexane (20 mL×2) successively, and dried to obtain the title compound 18d (12 g, yield: 76.1%).

MS m/z (ESI): 316.0 [M+1]

Step 4

8-Bromo-7-(2,4-difluorophenyl)-[1,2,4]triazolo[4,3-c]pyrimidin-5-amine 18e

Compound 18d (4 g, 12.65 mmol) and (tri)ethyl orthoformate (2.25 g, 15.18 mmol) were dissolved in 50 mL of ethanol. The reaction solution was stirred under reflux for 2 hours. The reaction was stopped, and the reaction solution was cooled to room temperature and concentrated under reduced pressure. The resulting residue was pulped in 5 mL of ethanol for 0.5 hour, and filtrated. The filter cake was washed with anhydrous diethyl ether (10 mL×2), and dried to obtain the title compound 18e (3.85 g, yield: 93.4%).

MS m/z (ESI): 326.2 [M+1]

Step 5

7-(2,4-Difluorophenyl)-8-(2-methyl-6-(trifluoromethyl)pyridin-4-yl)-[1,2,4]triazolo[4,3-c]pyrimidin-5-amine 18

Compound 18e (110 mg, 337.32 μmol), compound 1c (145.26 mg, 505.98 μmol), [1,1'-bis(diphenylphosphino)ferrocene]dichloropalladium (24.7 mg, 33.73 μmol) and potassium carbonate (93.1 mg, 674.64 μmol) were added successively to 12 mL of a mixed solution of 1,4-dioxane and water (V/V=5:1) under an argon atmosphere. The reaction solution was heated to 90° C., and stirred for 3 hours. The reaction solution was cooled to room temperature, added with water, and extracted with ethyl acetate (20 mL×3). The organic phases were combined, washed with saturated sodium chloride solution, dried over anhydrous sodium sulfate, and filtrated. The filtrate was concentrated under reduced pressure, and the residue was purified by high performance liquid chromatography (Waters 2767-SQ Detecor2, elution system: ammonium bicarbonate, water, acetonitrile) to obtain the title compound 18 (31 mg, yield: 22.6%).

MS m/z (ESI): 407.4 [M+1]

$^1$H NMR (400 MHz, DMSO-d$_6$) δ 9.41 (s, 1H), 8.50 (brs, 2H), 7.55 (brs, 2H), 7.44 (s, 1H), 7.20-7.18 (m, 2H), 2.49 (s, 3H).

Example 19

8-(2,6-Dimethylpyridin-4-yl)-7-(2-fluorophenyl)-[1,2,4]triazolo[4,3-c]pyrimidin-5-amine 19

19

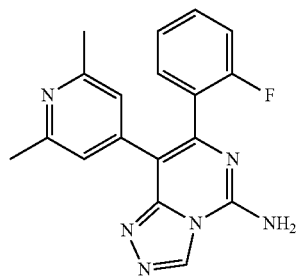

19a

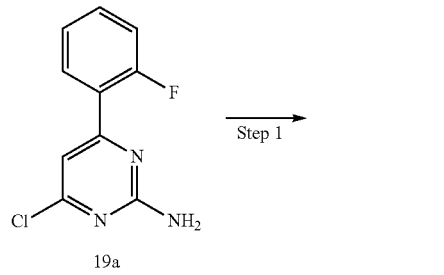

19b

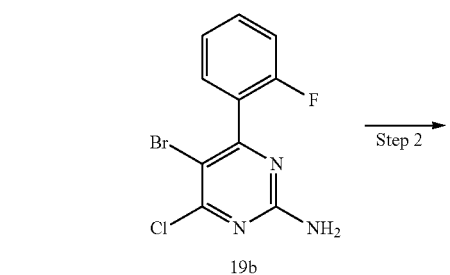

19c

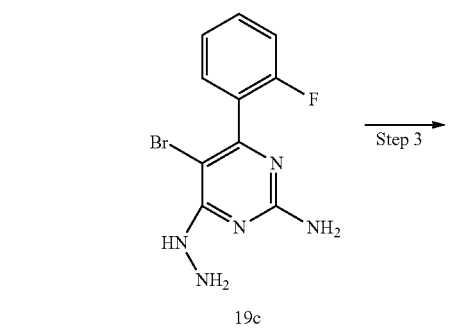

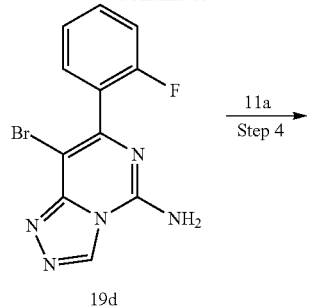

19d

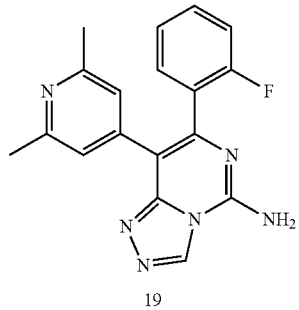 [SMILES: Cc1cc(-c2c(-c3ccccc3F)nc(N)n3cnnc23)cc(C)n1]

19

Step 1

5-Bromo-4-chloro-6-(2,4-difluorophenyl)pyrimidin-2-amine 19b

4-Chloro-6-(2-fluorophenyl)pyrimidin-2-amine 19a (1.5 g, 6.71 mmol, prepared according to the method disclosed in the patent application "WO 2014162039A1") was dissolved in 20 mL of N,N-dimethylformamide. The reaction solution was added with N-bromosuccinimide (1.31 g, 7.38 mmol), and stirred for 1 hour. The reaction solution was added with 120 mL of water, stirred and filtrated. The filter cake was collected, and dried in vacuum to obtain the crude title compound 19b (1.9 g), which was used directly in the next step without purification.

MS m/z (ESI): 301.9 [M+1]

Step 2

5-Bromo-4-(2-fluorophenyl)-6-hydrazinylpyrimidin-2-amine 19c

The crude compound 19b (1.9 g, 6.28 mmol) was dissolved in 30 mL of ethanol. The reaction solution was added with 85% hydrazine hydrate (125.61 mmol, 7.18 mL), and stirred at 60° C. for 1 hour. The reaction solution was filtrated. The filter cake was washed with ethanol (20 mL×2), and dried to obtain the title compound 19c (1.7 g, yield: 90.8%).

MS m/z (ESI): 297.8 [M+1]

Step 3

8-Bromo-7-(2-fluorophenyl)-[1,2,4]triazolo[4,3-c]pyrimidin-5-amine 19d

Compound 19c (1.7 g, 5.70 mmol) was added to 10 mL of (tri)ethyl orthoformate. The reaction solution was stirred at 130° C. for 0.5 hour. The reaction solution was cooled to room temperature and filtrated. The filter cake was added with ethyl acetate, stirred and filtrated. The filter cake was dried to obtain the title compound 19d (1.1 g, yield: 62.6%).

MS m/z (ESI): 307.9 [M+1]

Step 4

8-(2,6-Dimethylpyridin-4-yl)-7-(2-fluorophenyl)-[1,2,4]triazolo[4,3-c]pyrimidin-5-amine 19

Compound 19d (200 mg, 649.12 μmol), compound 11a (151.32 mg, 649.12 μmol), [1,1'-bis(diphenylphosphino)ferrocene]dichloropalladium (47.45 mg, 64.91 μmop and potassium carbonate (179.16 mg, 1.30 mmol) were added successively to 12 mL of a mixed solution of 1,4-dioxane and water (V/V=5:1) under an argon atmosphere. The reaction solution was heated to 80° C., and stirred for 3 hours. The reaction solution was cooled to room temperature, added with water, and extracted with ethyl acetate (20 mL×3). The organic phases were combined, washed with saturated sodium chloride solution, dried over anhydrous sodium sulfate, and filtrated. The filtrate was concentrated under reduced pressure, and the residue was purified by high performance liquid chromatography (Waters 2767-SQ Detecor2, elution system: ammonium bicarbonate, water, acetonitrile) to obtain the title compound 19 (26 mg, yield: 12%).

MS m/z (ESI): 335.4 [M+1]

$^1$H NMR (400 MHz, DMSO-d$_6$) δ 9.38 (s, 1H), 8.30 (s, 2H), 7.41 (brs, 2H), 7.19-7.22 (m, 1H), 7.09-7.13 (m, 1H), 6.91 (s, 2H), 2.29 (s, 6H).

Example 20

8-(2-(Difluoromethyl)-6-methylpyridin-4-yl)-7-(2,4-difluorophenyl)-[1,2,4]triazolo[4,3-c]pyrimidin-5-amine 20

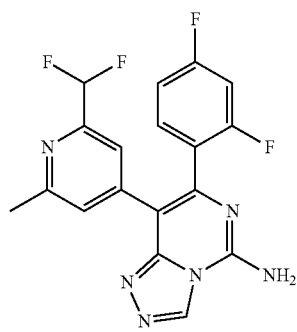

20

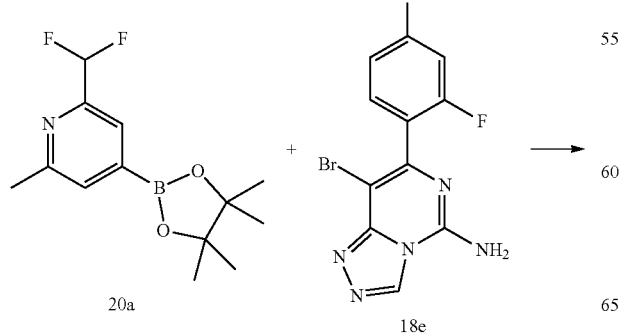

20a    18e

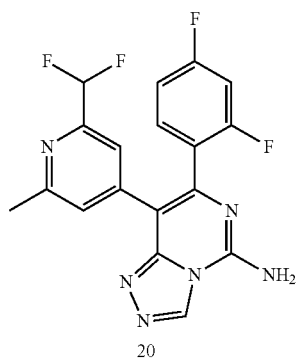

20

2-(Difluoromethyl)-6-methyl-4-(4,4,5,5-tetramethyl-1,3,2-dioxaborolan-2-yl)pyridine 20a (247.56 mg, 919.96 μma prepared according to the method disclosed in the patent application "WO2011095625A1"), compound 18e (200 mg, 613.31 μmol), [1,1'-bis(diphenylphosphino)ferrocene]dichloropalladium (44.88 mg, 61.33 μmol) and potassium carbonate (254.29 mg, 1.84 mmol) were added successively to 12 mL of a mixed solution of 1,4-dioxane and water (V/V=5:1) under an argon atmosphere. The reaction solution was heated to 90° C., and stirred for 2 hours. The reaction solution was cooled to room temperature, and concentrated under reduced pressure. The residue was purified by CombiFlash rapid preparation instrument with eluent system B. The resulting crude product was purified by high performance liquid chromatography (Waters 2767-SQ Detecor2, elution system: ammonium bicarbonate, water, acetonitrile) to obtain the title compound 20 (26 mg, yield: 12%).

MS m/z (ESI): 389.5 [M+1]

$^1$H NMR (400 MHz, DMSO-d$_6$) δ 9.40 (s, 1H), 8.44 (brs, 2H), 7.54 (s, 1H), 7.40-7.18 (m, 4H), 6.96-6.69 (m, 1H), 2.44 (s, 3H).

Example 21

8-(2,6-Dimethylpyridin-4-yl)-2-methyl-7-phenylimidazo[1,2-c]pyrimidin-5-amine 21

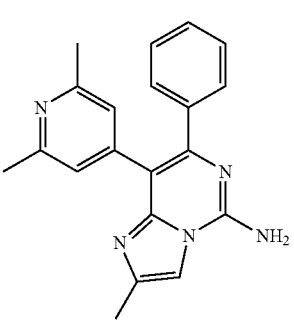

21

85
-continued

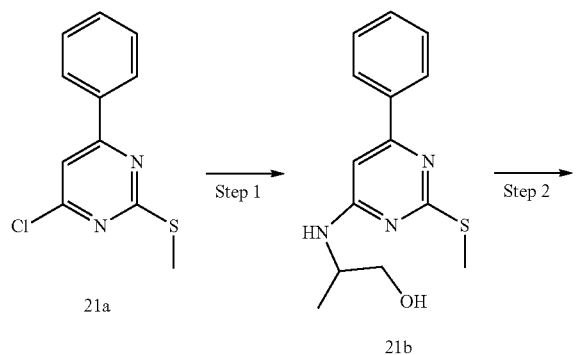

21a → Step 1 → 21b → Step 2 →

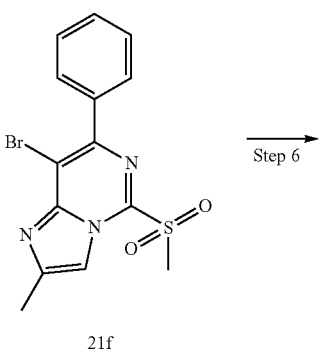

21c → Step 3 → 21d → Step 4 →

21e → Step 5 → 21f → Step 6 →

86
-continued

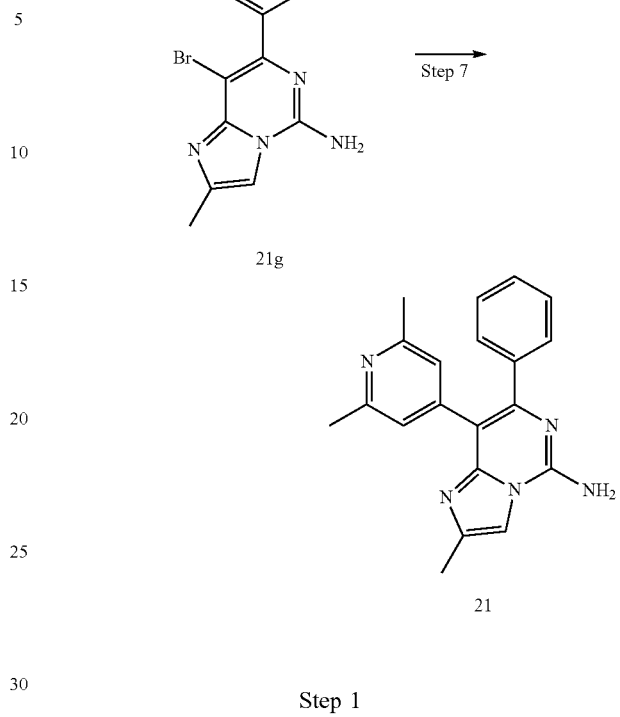

21g → Step 7 →

21

Step 1

2-((2-(Methylthio)-6-phenylpyrimidin-4-yl)amino)propan-1-ol 21b

4-Chloro-2-methylthio-6-phenyl-pyrimidine 21a (1.5 g, 6.34 mmol, prepared according to the known method disclosed in "Tetrahedron, 1994, 50(34), 10299-308") was dissolved in 40 mL of acetonitrile. The reaction solution was added with 2-aminopropan-1-ol (713.91 mg, 9.50 mmol) and N,N-diisopropylethylamine (1.64 g, 12.67 mmol), and stirred at 75° C. for 72 hours. The reaction solution was concentrated under reduced pressure, and the residue was purified by silica gel column chromatography with eluent system A to obtain the title compound 21b (1.5 g, yield: 86%).

MS m/z (ESI): 276.2 [M+1]

Step 2

2-((5-Bromo-2-(methylthio)-6-phenylpyrimidin-4-yl)amino)propan-1-ol 21c

Compound 21b (1.5 g, 5.45 mmol) was dissolved in 30 mL of N,N-dimethylformamide. The reaction solution was added with N-bromosuccinimide (969.50 mg, 5.45 mmol) in batches, and stirred for 1 hour. The reaction solution was added with 150 mL of water, and extracted with a mixed solution of dichloromethane and methanol (V/V=8:1) three times. The organic phases were combined, washed with water and saturated sodium chloride solution successively, dried over anhydrous sodium sulfate, and filtrated. The filtrate was concentrated under reduced pressure, and the residue was purified by silica gel column chromatography with eluent system A to obtain the title compound 21c (1.2 g, yield: 62.2%).

MS m/z (ESI): 354.1 [M+1]

Step 3

8-Bromo-2-methyl-5-(methylthio)-7-phenyl-2,3-dihydroimidazo[1,2-c]pyrimidine 21d Compound 21c (2.3 g, 6.49 mmol) was dissolved in 40 mL of dichloromethane. The reaction solution was added with triethylamine (983.59 mg, 9.74 mmol), added dropwise with methanesulfonyl chloride (892.44 mg, 7.79 mmol), and stirred overnight. The reaction solution was added with saturated sodium bicarbonate solution, and extracted with dichloromethane three times (30 mL×3). The organic phases were combined, washed with saturated sodium chloride solution, dried over anhydrous sodium sulfate, and filtrated. The filtrate was concentrated under reduced pressure, and the residue was purified by silica gel column chromatography with eluent system A to obtain the title compound 21d (1.2 g, yield: 55%).

MS m/z (ESI): 336.0 [M+1]

Step 4

8-Bromo-2-methyl-5-(methylthio)-7-phenylimidazo[1,2-c]pyrimidine 21e

Compound 21d (1.2 g, 3.57 mmol) was added to 1,4-dioxane. The reaction solution was added with manganese dioxide (3.14 g, 35.69 mmol), and stirred at 90° C. for 36 hours. The reaction solution was cooled to room temperature, and filtrated through celite. The filter cake was washed with methanol, and the filtrate was concentrated under reduced pressure. The residue was purified by silica gel column chromatography with eluent system A to obtain the title compound 21e (750 mg, yield: 62.9%).

MS m/z (ESI): 334.1 [M−1]

Step 5

8-Bromo-2-methyl-5-(methylsulfonyl)-7-phenylimidazo[1,2-c]pyrimidine 21f

Compound 21e (320 mg, 957.41 μmmol) was dissolved in 5 mL of trifluoroacetic acid. The reaction solution was added dropwise with hydrogen peroxide (0.5 mL, 957.41 μmmol), and stirred for 1 hour. The reaction solution was neutralized with saturated sodium carbonate solution, and extracted with dichloromethane (30 mL×3). The organic phases were combined, washed with saturated sodium chloride solution, dried over anhydrous sodium sulfate, and filtrated. The filtrate was concentrated under reduced pressure to obtain the crude title compound 21f (350 mg), which was used directly in the next step without purification.

Step 6

8-Bromo-2-methyl-7-phenylimidazo[1,2-c]pyrimidin-5-amine 21g

The crude compound 21f (350 mg, 955.68 μmmol) was dissolved in 10 mL of 1,4-dioxane. The reaction solution was added with ammonia monohydrate (1.0 mL, 955.68 μmmol), and stirred at 40° C. for 1 hour. The reaction solution was concentrated under reduced pressure, added with water, and extracted with a mixed solution of dichloromethane and methanol (V/V=8:1) three times. The organic phases were combined, washed with saturated sodium chloride solution, dried over anhydrous sodium sulfate, and filtrated. The filtrate was concentrated under reduced pressure, and the residue was purified by thin layer chromatography with developing solvent system A to obtain the title compound 21g (215 mg, yield: 74.2%).

Step 7

8-(2,6-Dimethylpyridin-4-yl)-2-methyl-7-phenylimidazo[1,2-c]pyrimidin-5-amine 21

Compound 21g (215 mg, 709.20 μmmol), compound 11a (247.99 mg, 1.06 mmol), [1,1'-bis(diphenylphosphino)ferrocene]dichloropalladium (51.84 mg, 70.92 μmmol) and sodium bicarbonate (131.06 mg, 1.56 mmol) were added successively to 12 mL of a mixed solution of 1,4-dioxane and water (V/V=5:1) under an argon atmosphere. The reaction solution was heated to 80° C., and stirred for 2 hours. The reaction solution was cooled to room temperature, added with water, and extracted with ethyl acetate (20 mL×3). The organic phases were combined, washed with saturated sodium chloride solution, dried over sodium sulfate, and filtrated. The filtrate was concentrated under reduced pressure, and the residue was purified by high performance liquid chromatography (Waters 2767-SQ Detecor2, elution system: ammonium bicarbonate, water, acetonitrile) to obtain the title compound 21 (45 mg, yield: 19.3%).

MS m/z (ESI): 330.4 [M+1]

$^1$H NMR (400 MHz, DMSO-$d_6$) δ 7.68 (s, 1H), 7.65 (s, 2H), 7.28 (s, 2H), 7.24 (s, 3H), 6.89 (s, 2H), 2.31 (s, 6H), 2.27 (s, 3H).

Example 22

8-(2-Methyl-6-((4-methylpiperazin-1-yl)methyl)pyridin-4-yl)-7-phenyl-[1,2,4]triazolo[4,3-c]pyrimidin-5-amine 22

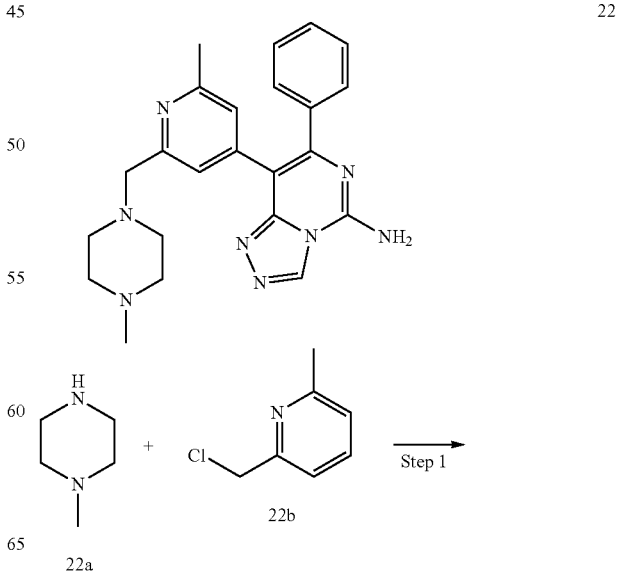

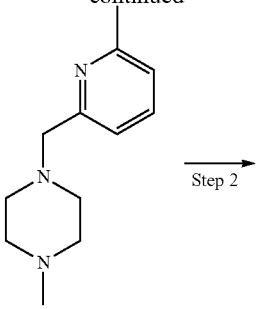

22c

Step 2

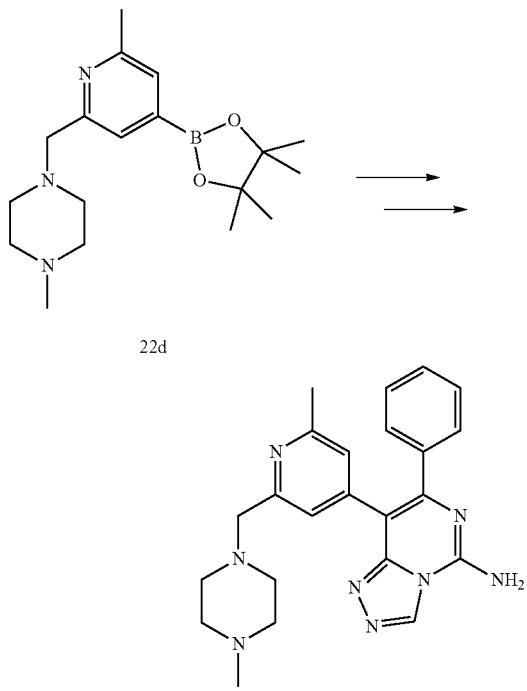

22d

22

Step 1

1-Methyl-4-((6-methylpyridin-2-yl)methyl)piperazine 22c 2-(Chloromethyl)-6-methylpyridine 22b (1 g, 7.06 mmol) and potassium carbonate (1.46 g, 10.59 mmol) were dissolved in 40 mL of acetonitrile. The reaction solution was added with 1-methylpiperazine 22a (848.57 mg, 8.47 mmol, 939.72 uL), and stirred at 80° C. for 17 hours. The reaction solution was purified by silica gel column chromatography with eluent system A to obtain the title compound 22c (1 g, yield: 69%).

MS m/z (ESI): 206.4 [M+1]

Step 2

1-Methyl-4-((6-methyl-4-(4,4,5,5-tetramethyl-1,3,2-dioxaborolan-2-yl)pyridin-2-yl)methyl)piperazine 22d Compound 22c (1 g, 4.87 mmol), compound 5a (146.13 μmmol) and (1,5-cyclooctadiene)(methoxy)iridium(I) dimer (78.44 mg, 292.26 μmmol) were dissolved in 40 mL of n-hexane under an argon atmosphere. The reaction solution was stirred at 80° C. for 17 hours. The reaction solution was concentrated under reduced pressure, and purified by silica gel column chromatography with eluent system B to obtain the title compound 22d (217 mg, yield: 13.5%).

In accordance with the synthetic route of Example 5, the starting compound 5b in Step 1 was replaced with 22d, accordingly, the title compound 22 (27.6 mg) was prepared.

MS m/z (ESI): 415.5 [M+1]

$^1$H NMR (400 MHz, DMSO-d$_6$) δ 9.34 (s, 1H), 8.26 (brs, 2H), 7.32-7.28 (m, 6H), 6.85 (s, 1H), 3.38 (s, 2H), 2.54 (s, 3H), 2.43 (s, 3H), 2.19-2.09 (m, 8H).

Example 23

8-(2-Chloro-6-(trifluoromethyl)pyridin-4-yl)-7-phenyl-[1,2,4]triazolo[4,3-c]pyrimidin-5-amine 23

23

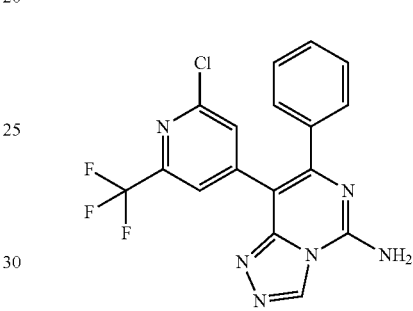

In accordance with the synthetic route of Example 4, the starting compound 4a in Step 1 was replaced with 2-chloro-4-(4,4,5,5-tetramethyl-1,3,2-dioxaborolan-2-yl)-6-(trifluoromethyl)pyridine 23a (prepared according to the known method disclosed in "*Research on Chemical Intermediates*, 2013, 39(4), 1917-1926"), accordingly, the title compound 23 (11.8 mg) was prepared.

MS m/z (ESI): 391.4 [M+1]

$^1$H NMR (400 MHz, DMSO-d$_6$) δ 9.40 (s, 1H), 8.58 (brs, 2H), 7.82 (s, 1H), 7.65 (s, 1H), 7.40-7.36 (m, 5H).

Example 24

8-(2-Chloro-6-methylpyridin-4-yl)-7-phenylimidazo[1,2-c]pyrimidin-5-amine 24

24

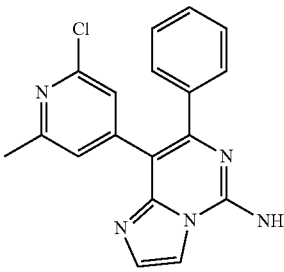

In accordance with the synthetic route of Example 17, the starting compound 1c in Step 5 was replaced with compound 4a, accordingly, the title compound 24 (32 mg) was prepared.

MS m/z (ESI): 336.4 [M+1]

$^1$H NMR (400 MHz, DMSO-d$_6$) δ 8.00 (s, 1H), 7.93 (s, 2H), 7.55 (s, 1H), 7.31 (s, 5H), 7.14 (d, 2H), 2.33 (s, 3H).

Example 25

8-(2-Methoxy-6-methylpyridin-4-yl)-7-phenyl-[1,2,4]triazolo[4,3-c]pyrimidin-5-amine 25

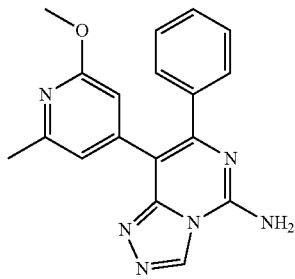

25

In accordance with the synthetic route of Example 4, the starting compound 4a in Step 1 was replaced with 2-methoxy-6-methyl-4-(4,4,5,5-tetramethyl-1,3,2-dioxaborolan-2-yl)pyridine 25a (prepared according to the known method disclosed in "*Chemistry—A European Journal*, 2017, 23(24), 5663-5667"), accordingly, the title compound 25 (11.8 mg) was prepared.

MS m/z (ESI): 333.2 [M+1]

$^1$H NMR (400 MHz, DMSO-d$_6$) δ 9.33 (s, 1H), 8.24 (brs, 2H), 7.36-7.29 (m, 5H), 6.76 (s, 1H), 6.48 (s, 1H), 3.77 (s, 3H), 2.29 (s, 3H).

Example 26

8-(2-Ethyl-6-methylpyridin-4-yl)-7-phenyl-[1,2,4]triazolo[4,3-c]pyrimidin-5-amine 26

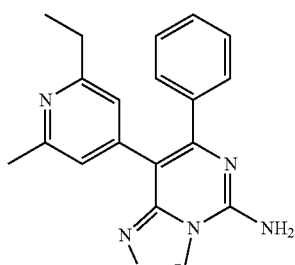

26

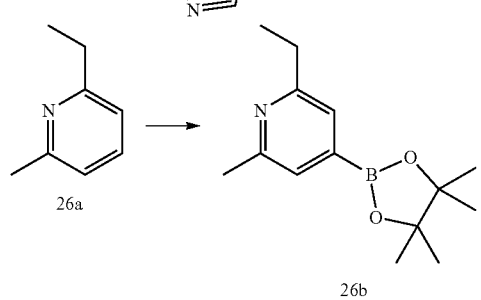

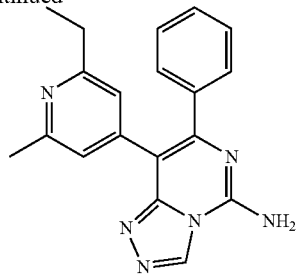

26

2-Ethyl-6-methylpyridine 26a (1 g, 8.25 mmol, Accela ChemBio (Shanghai) Inc.), compound 5a (2.31 g, 9.08 mmol), (1Z,5Z)-cycloocta-1,5-diene; iridium; methyloxonium (164.10 mg, 247.57 μmmol) and 4-tert-butyl-2-(4-tert-butyl-2-pyridyl)pyridine (588 mg, 6.00 mmol) were added successively to 40 mL of n-hexane under an argon atmosphere. The reaction solution was heated to 80° C., and stirred for 17 hours. The reaction solution was concentrated under reduced pressure, and the residue was purified by silica gel column chromatography with eluent system B to obtain 2-ethyl-6-methyl-4-(4,4,5,5-tetramethyl-1,3,2-dioxaborolan-2-yl)pyridine 26b (809 mg, yield: 39.7%).

MS m/z (ESI): 248.2 [M+1]

In accordance with the synthetic route of Example 4, the starting compound 4a in Step 1 was replaced with 26b, accordingly, the title compound 26 (136.6 mg) was prepared.

MS m/z (ESI): 331.1 [M+1]

$^1$H NMR (400 MHz, DMSO-d$_6$) δ 9.35 (s, 1H), 8.25 (brs, 2H), 7.32-7.28 (m, 5H), 7.12 (s, 1H), 6.80 (s, 1H), 2.57-2.55 (m, 2H), 2.37 (s, 3H), 1.03-1.00 (m, 3H).

Example 27

8-(2-Chloro-6-methylpyridin-4-yl)-7-(2-fluorophenyl)-[1,2,4]triazolo[4,3-c]pyrimidin-5-amine 27

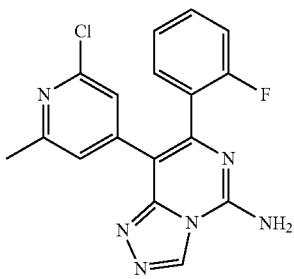

27

In accordance with the synthetic route of Example 19, the starting compound 11a in Step 4 was replaced with compound 4a, accordingly, the title compound 27 (73 mg) was prepared.

MS m/z (ESI): 355.4 [M+1]

$^1$H NMR (400 MHz, DMSO-d$_6$) δ 8.39 (s, 1H), 8.44 (s, 2H), 7.49-7.45 (m, 2H), 7.28-7.24 (m, 1H), 7.17-7.14 (m, 2H), 7.11 (s, 1H), 2.33 (s, 3H).

Example 28

8-(2,6-Dimethylpyridin-4-yl)-7-(4-fluorophenyl)-[1,2,4]triazolo[4,3-c]pyrimidin-5-amine 28

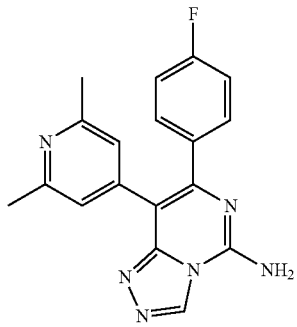

28

In accordance with the synthetic route of Example 15, the starting compound 4a in Step 5 was replaced with compound 11a, accordingly, the title compound 28 (38 mg) was prepared.

MS m/z (ESI): 335.4 [M+1]

$^1$H NMR (400 MHz, DMSO-d$_6$) δ 9.34 (s, 1H), 8.24 (brs, 2H), 7.39-7.35 (m, 2H), 7.16-7.11 (m, 2H), 6.95 (s, 2H), 2.33 (s, 6H).

Example 29

7-(3-Fluorophenyl)-8-(2-methyl-6-(trifluoromethyl)pyridin-4-yl)-[1,2,4]triazolo[4,3-c]pyrimidin-5-amine 29

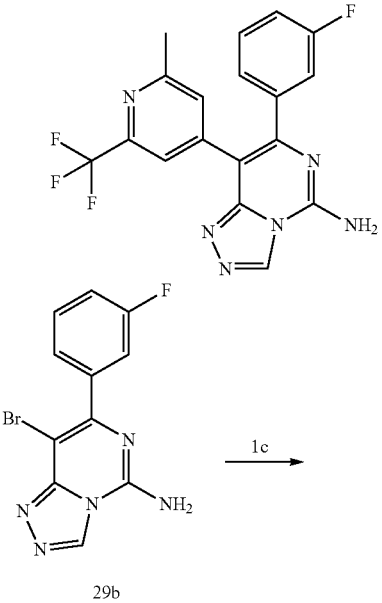

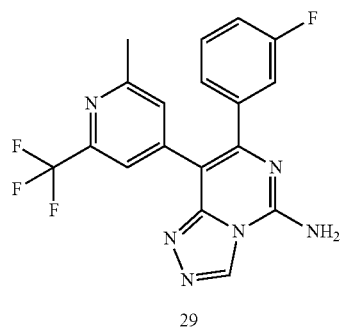

29

In accordance with the synthetic route of Example 15, the starting compound 15b in Step 1 was replaced with (3-fluorophenyl)boronic acid 29a, accordingly, the compound 8-bromo-7-(3-fluorophenyl)-[1,2,4]triazolo[4,3-c]pyrimidin-5-amine 29b was prepared.

The starting compound 4a in Step 5 of Example 15 was replaced with compound 1e, accordingly, the title compound 29 (28 mg) was prepared.

MS m/z (ESI): 389.4 [M+1]

$^1$H NMR (400 MHz, DMSO-d$_6$) δ 9.39 (s, 1H), 8.46 (brs, 2H), 7.60 (s, 1H), 7.48 (s, 1H), 7.36-7.34 (m, 1H), 7.23-7.19 (m, 2H), 7.10-7.08 (m, 1H), 2.49 (s, 3H).

Example 30

8-(2-Cyclopropyl-6-methylpyridin-4-yl)-7-phenyl-[1,2,4]triazolo[4,3-c]pyrimidin-5-amine 30

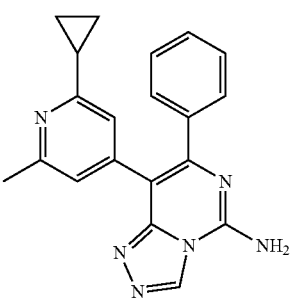

30

In accordance with the synthetic route of Example 11, the starting compound 11a in Step 1 was replaced with 2-cyclopropyl-6-methyl-4-(4,4,5,5-tetramethyl-1,3,2-dioxaborolan-2-yl)pyridine 30a (prepared according to the method disclosed in the patent application "WO2011070131A1"), accordingly, the title compound 30 (43 mg) was prepared.

MS m/z (ESI): 343.2 [M+1]

$^1$H NMR (400 MHz, DMSO-d$_6$) δ 9.34 (s, 1H), 8.23 (brs, 2H), 7.47-7.31 (m, 5H), 6.92-6.87 (m, 2H), 2.28 (s, 3H), 1.98-1.90 (m, 1H), 0.84-0.72 (m, 4H).

Example 31

8-(2,6-Dimethylpyridin-4-yl)-7-phenylimidazo[1,2-c]pyrimidin-5-amine 31

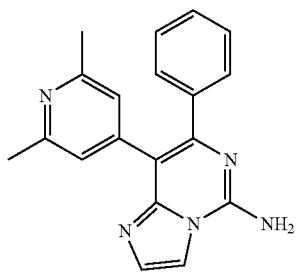

31

In accordance with the synthetic route of Example 17, the starting compound 1c in Step 5 was replaced with compound 11a, accordingly, the title compound 31 (40 mg) was prepared.

MS m/z (ESI): 316.4 [M+1]

$^1$H NMR (400 MHz, DMSO-d$_6$) δ 8.00 (s, 1H), 7.99 (s, 2H), 7.51 (d, 1H), 7.31-7.29 (m, 2H), 7.26-7.25 (m, 3H), 6.91 (s, 2H), 2.30 (s, 6H).

Example 32

8-(2,6-Dimethylpyridin-4-yl)-7-(4-fluorophenyl)imidazo[1,2-c]pyrimidin-5-amine 32

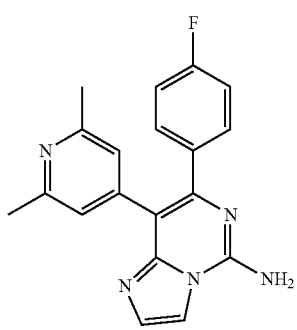

32

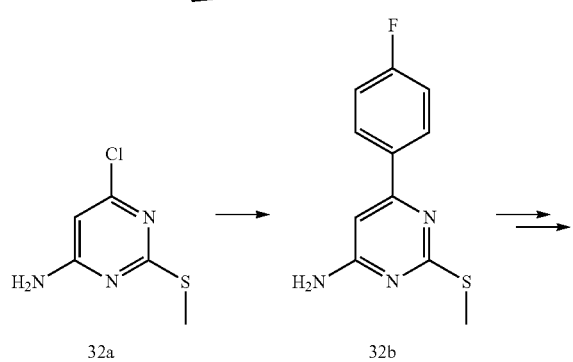

32

6-Chloro-2-(methylthio)pyrimidin-4-amine 32a (2.0 g, 11.39 mmol, Shanghai Bide Pharmatech Ltd.) and (4-fluorophenyl)boronic acid (2.39 g, 17.08 mmol) were dissolved in 50 mL of toluene under an argon atmosphere. Tetra (triphenylphosphine)palladium (657.60 mg, 569.35 μmmol), sodium carbonate (2.41 g, 22.77 mmol) and 10 mL of water were added successively. The reaction solution was stirred at 90° C. for 3 hours, then added with water, and extracted with ethyl acetate three times (50 mL×3). The organic phases were combined, washed with saturated sodium chloride solution, dried over anhydrous sodium sulfate, and filtrated. The filtrate was concentrated under reduced pressure, and the residue was added with methanol, stirred and filtrated. The filter cake was collected to obtain 6-(4-fluorophenyl)-2-(methylthio)pyrimidin-4-amine 32b (1.3 g, yield: 48.5%).

In accordance with the synthetic route of Example 17, the starting compound 17a in Step 1 was replaced with 32b, accordingly, 8-bromo-7-(4-fluorophenyl)imidazo[1,2-c]pyrimidin-5-amine 32c was prepared. The starting compound 1c in Step 5 of Example 17 was replaced with compound 11a, accordingly, the title compound 32 (70 mg) was prepared.

MS m/z (ESI): 334.4 [M+1]

$^1$H NMR (400 MHz, DMSO-d$_6$) δ 7.98 (d, 1H), 7.82 (s, 2H), 7.52 (d, 1H), 7.35-7.32 (m, 2H), 7.28-7.08 (m, 2H), 6.92 (s, 2H), 2.32 (s, 6H).

Example 33

7-(2-Fluorophenyl)-8-(2-methyl-6-(trifluoromethyl)pyridin-4-yl)-[1,2,4]triazolo[4,3-c]pyrimidin-5-amine 33

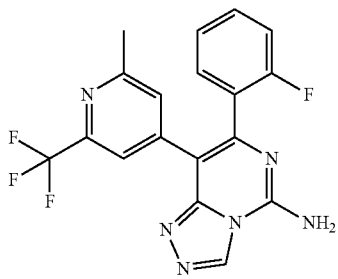

In accordance with the synthetic route of Example 19, the starting compound 11a in Step 4 was replaced with compound 1e, accordingly, the title compound 33 (25 mg) was prepared.

MS m/z (ESI): 389.4 [M+1]

¹H NMR (400 MHz, DMSO-d₆) δ 9.43 (s, 1H), 8.48 (brs, 2H), 7.55 (s, 1H), 7.50-7.44 (m, 2H), 7.42 (s, 1H), 7.28-7.26 (m, 1H), 7.15-7.12 (m, 1H), 2.46 (s, 3H)

Example 34

8-(2-Chloro-6-methylpyridin-4-yl)-7-(2,4-difluorophenyl)-[1,2,4]triazolo[4,3-c]pyrimidin-5-amine 34

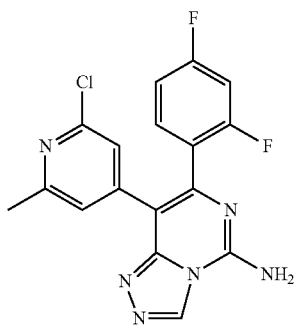

In accordance with the synthetic route of Example 18, the starting compound 1c in Step 5 was replaced with compound 4a, accordingly, the title compound 34 (30.4 mg) was prepared.

MS m/z (ESI): 373.3 [M+1]

¹H NMR (400 MHz, DMSO-d₆) δ 9.39 (s, 1H), 8.46 (brs, 2H), 7.55-7.54 (m, 1H), 7.25-7.14 (m, 4H), 2.36 (s, 3H).

Example 35

8-(2-Chloro-6-methylpyridin-4-yl)-7-(p-tolyl)-[1,2,4]triazolo[4,3-c]pyrimidin-5-amine 35

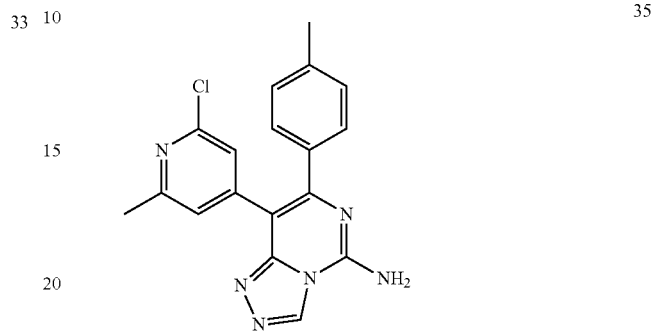

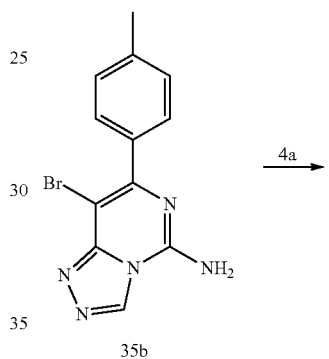

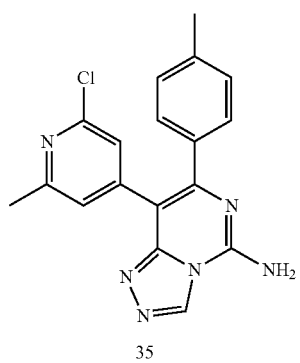

In accordance with the synthetic route of Example 15, the starting compound 15b in Step 1 was replaced with p-tolylboronic acid 35a (Shanghai Dari Chemical Ltd.), accordingly, 8-bromo-7-(p-tolyl)-[1,2,4]triazolo[4,3-c]pyrimidin-5-amine 35b was prepared.

The starting compound 15f in Step 5 of Example 15 was replaced with compound 35b, accordingly, the title compound 35 (21.3 mg) was prepared.

MS m/z (ESI): 351.1 [M+1]

¹H NMR (400 MHz, DMSO-d₆) δ 9.34 (s, 1H), 8.33 (brs, 2H), 7.26-7.13 (m, 6H), 2.36 (s, 3H), 2.30 (s, 3H).

Example 36

8-(2-Chloro-6-methylpyridin-4-yl)-7-(4-chlorophenyl)-[1,2,4]triazolo[4,3-c]pyrimidin-5-amine 36

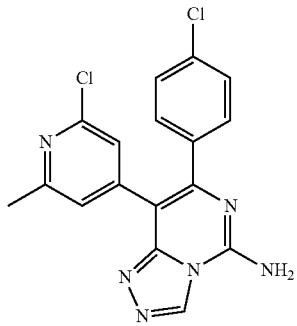

In accordance with the synthetic route of Example 14, the starting compound 1c in Step 4 was replaced with compound 4a, accordingly, the title compound 36 (45.9 mg) was prepared.

MS m/z (ESI): 371.4 [M+1]

$^1$H NMR (400 MHz, DMSO-$d_6$) δ 9.36 (s, 1H), 8.40 (brs, 2H), 7.43-7.35 (m, 4H), 7.20-7.18 (m, 2H), 2.38 (s, 3H).

Example 37

7-Phenyl-8-(pyridin-4-yl)-[1,2,4]triazolo[4,3-c]pyrimidin-5-amine 37

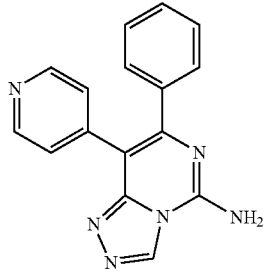

In accordance with the synthetic route of Example 2, the starting compound 2d in Step 4 was replaced with 4-(4,4,5,5-tetramethyl-1,3,2-dioxaborolan-2-yl)pyridine 37a (Shanghai Bide Pharmatech Ltd.), accordingly, the title compound 37 (20 mg) was prepared.

MS m/z (ESI): 289.0 [M+1]

$^1$H NMR (400 MHz, DMSO-$d_6$) δ 9.35 (s, 1H), 8.47-8.46 (m, 2H), 8.29 (brs, 2H), 7.33-7.29 (m, 7H).

Example 38

8-(2-Chloropyridin-4-yl)-7-phenyl-[1,2,4]triazolo[4,3-c]pyrimidin-5-amine 38

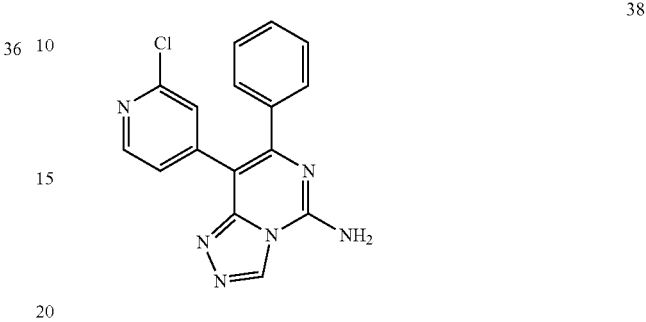

In accordance with the synthetic route of Example 2, the starting compound 2d in Step 4 was replaced with 2-chloro-4-(4,4,5,5-tetramethyl-1,3,2-dioxaborolan-2-yl)pyridine 38a (Adamas Reagent Ltd.), accordingly, the title compound 38 (20 mg) was prepared.

MS m/z (ESI): 323.1 [M+1]

$^1$H NMR (400 MHz, DMSO-$d_6$) δ 9.36 (s, 1H), 8.40 (brs, 2H), 8.28-8.27 (m, 1H), 7.47 (s, 1H), 7.38-7.31 (m, 5H), 7.23-7.22 (m, 1H).

Example 39

8-(2-Chloro-6-(trifluoromethyl)pyridin-4-yl)-7-(2,4-difluorophenyl)-[1,2,4]triazolo[4,3-c]pyrimidin-5-amine 39

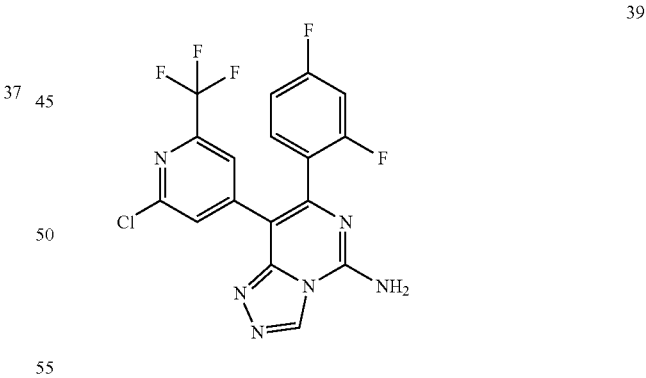

In accordance with the synthetic route of Example 18, the starting compound 1c in Step 5 was replaced with 2-chloro-4-(4,4,5,5-tetramethyl-1,3,2-dioxaborolan-2-yl)-6-(trifluoromethyl)pyridine (prepared according to the known method disclosed in "*Research on Chemical Intermediates,* 2013, 39(4), 1917-1926"), accordingly, the title compound 39 (19.8 mg) was prepared.

MS m/z (ESI): 427.4 [M+1]

$^1$H NMR (400 MHz, DMSO-$d_6$) δ 9.66 (s, 1H), 8.80 (brs, 2H), 7.80 (s, 1H), 7.70 (s, 1H), 7.65-7.59 (m, 1H), 7.29-7.22 (m, 2H).

Example 40

7-(2,4-Difluorophenyl)-8-(2,6-dimethylpyridin-4-yl)-[1,2,4]triazolo[4,3-c]pyrimidin-5-amine 40

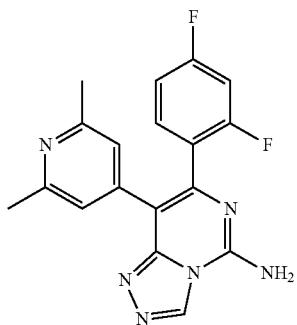

In accordance with the synthetic route of Example 18, the starting compound 1c in Step 5 was replaced with compound 11a, accordingly, the title compound 40 (40 mg) was prepared.

MS m/z (ESI): 353.1 [M+1]

$^1$H NMR (400 MHz, DMSO-d$_6$) δ 9.54 (s, 1H), 8.43 (brs, 2H), 7.51-7.45 (m, 1H), 7.21-7.10 (m, 2H), 6.92 (s, 2H), 2.31 (s, 6H).

Example 41

7-(2,4-Difluorophenyl)-8-(2-methoxy-6-methylpyridin-4-yl)-[1,2,4]triazolo[4,3-c]pyrimidin-5-amine 41

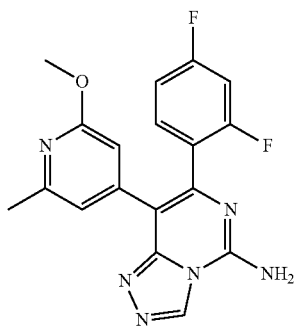

In accordance with the synthetic route of Example 18, the starting compound 1c in Step 5 was replaced with compound 25a, accordingly, the title compound 41 (10.6 mg) was prepared.

MS m/z (ESI): 369.5 [M+1]

$^1$H NMR (400 MHz, DMSO-d$_6$) δ 9.37 (s, 1H), 8.33 (brs, 2H), 7.50-7.48 (m, 1H), 7.22-7.13 (m, 2H), 6.76 (s, 1H), 6.45 (s, 1H), 3.76 (s, 3H), 2.30 (s, 3H).

Example 42

3-Methyl-8-(2-methyl-6-(trifluoromethyl)pyridin-4-yl)-7-phenyl-[1,2,4]triazolo[4,3-c]pyrimidin-5-amine 42

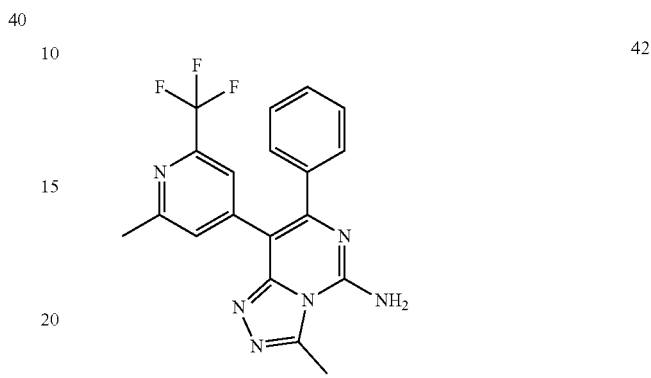

In accordance with the synthetic route of Example 1, the starting compound (tri)ethyl orthoformate in Step 4 was replaced with triethyl orthoacetate, accordingly, the title compound 42 (52 mg) was prepared.

MS m/z (ESI): 385.1 [M+1]

$^1$H NMR (400 MHz, DMSO-d$_6$) δ 7.69 (brs, 2H), 7.55 (s, 1H), 7.41 (s, 1H), 7.35-7.31 (m, 5H), 2.96 (s, 3H), 2.46 (s, 3H).

Example 43

5-(5-Amino-7-phenyl-[1,2,4]triazolo[4,3-c]pyrimidin-8-yl)-1-isopropylpyridin-2(11-1)-one 43

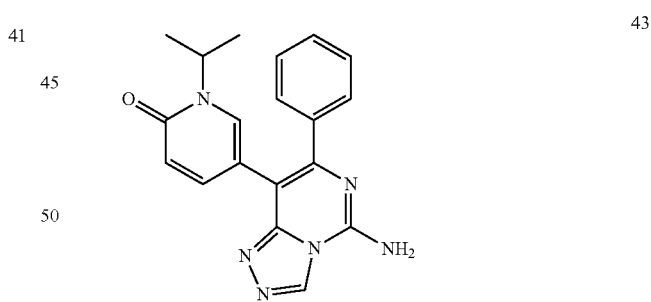

In accordance with the synthetic route of Example 4, the starting compound 4a in Step 1 was replaced with 1-isopropyl-5-(4,4,5,5-tetramethyl-1,3,2-dioxaborolan-2-yl)pyridine-2(11-1)-one 43a (prepared according to the method disclosed in the patent application "WO2011143426A1"), accordingly, the title compound 43 (31 mg) was prepared.

MS m/z (ESI): 347.1 [M+1]

$^1$H NMR (400 MHz, DMSO-d$_6$) δ 9.33 (s, 1H), 8.13 (brs, 2H), 7.47-7.33 (m, 7H), 6.38-6.35 (m, 1H), 4.97-4.90 (m, 1H), 0.99-0.97 (m, 6H).

μmmol μmmol

Example 44

8-(2-Cyclopropyl-6-methylpyridin-4-yl)-7-(2,4-difluorophenyl)-[1,2,4]triazolo[4,3-c]pyrimidin-5-amine 44

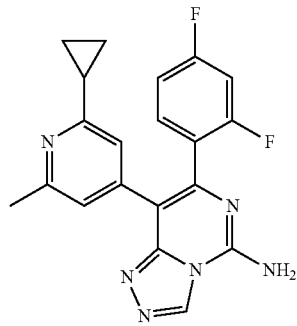

In accordance with the synthetic route of Example 18, the starting compound 1c in Step 5 was replaced with compound 30a, accordingly, the title compound 44 (79.4 mg) was prepared.

MS m/z (ESI): 379.5 [M+1]

$^1$H NMR (400 MHz, DMSO-d$_6$) δ 9.38 (s, 1H), 8.33 (brs, 2H), 7.52-7.46 (m, 1H), 7.21-7.11 (m, 2H), 6.90-6.85 (m, 2H), 2.28 (s, 3H), 1.95-1.85 (m, 1H), 0.85-0.83 (m, 2H), 0.72-0.70 (m, 2H).

Example 45

7-(2,4-Difluorophenyl)-8-(2-methylpyridin-4-yl)-[1,2,4]triazolo[4,3-c]pyrimidin-5-amine 45

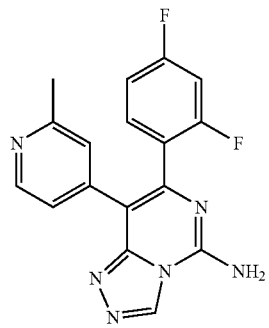

In accordance with the synthetic route of Example 18, the starting compound 1c in Step 5 was replaced with compound 12a, accordingly, the title compound 45 (79.4 mg) was prepared.

MS m/z (ESI): 339.4 [M+1]

$^1$H NMR (400 MHz, DMSO-d$_6$) δ 9.46 (s, 1H), 8.40 (brs, 2H), 8.31-8.30 (m, 1H), 7.53-7.47 (m, 1H), 7.22-7.11 (m, 3H), 6.98-6.97 (m, 1H), 2.39 (s, 3H).

Example 46

7-(2-Chloro-4-fluorophenyl)-8-(2-methyl-6-(trifluoromethyl)pyridin-4-yl)-[1,2,4]triazolo[4,3-c]pyrimidin-5-amine 46

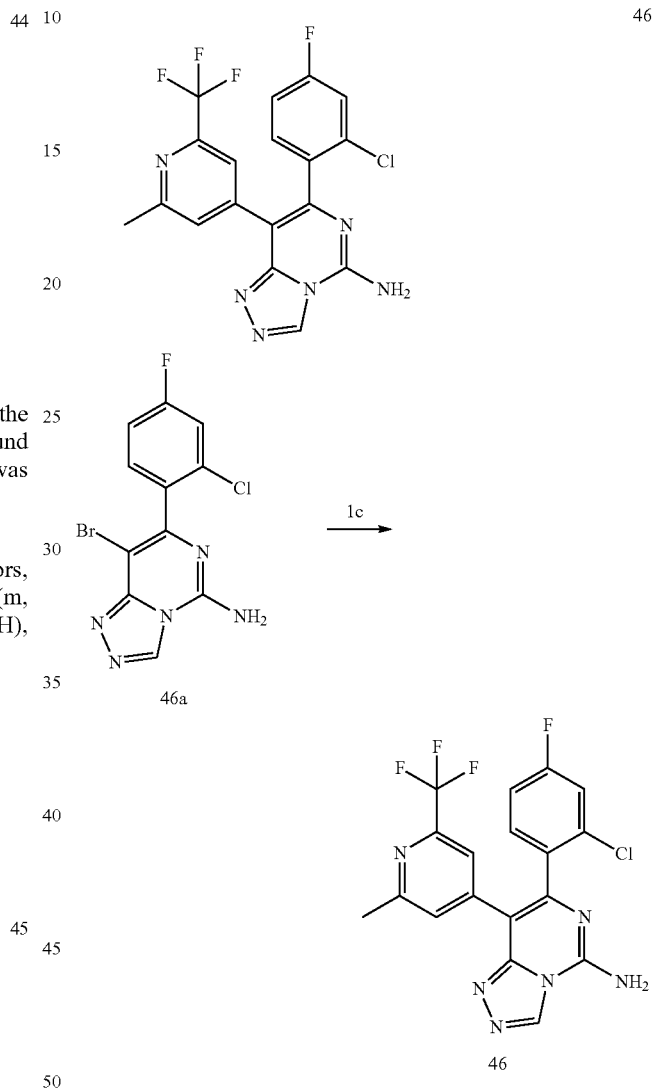

In accordance with the synthetic route of Example 15, the starting compound 15b in Step 1 was replaced with (2-chloro-4-fluorophenyl)boronic acid (Accela ChemBio (Shanghai) Inc.), accordingly, 8-bromo-7-(2-chloro-4-fluorophenyl)-[1,2,4]triazolo[4,3-c]pyrimidin-5-amine 46a was prepared.

The starting compound 4a in Step 5 of Example 15 was replaced with compound 1c, accordingly, the title compound 46 (32 mg) was prepared.

MS m/z (ESI): 423.3 [M+1]

$^1$H NMR (400 MHz, DMSO-d$_6$) δ 9.43 (s, 1H), 8.54 (brs, 2H), 7.54 (s, 1H), 7.53-7.49 (m, 2H), 7.47 (s, 1H), 7.40-7.28 (m, 1H), 2.47 (s, 3H).

Example 47

8-(2-Chloro-6-(morpholinomethyl)pyridin-4-yl)-7-phenyl-[1,2,4]triazolo[4,3-c]pyrimidin-5-amine 47

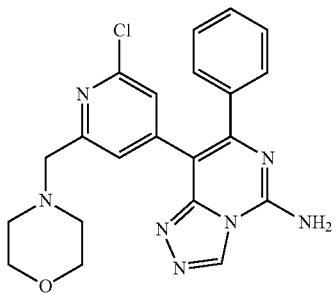

47

In accordance with the synthetic route of Example 22, the starting compound 22c was replaced with 4-((6-chloropyridin-2-yl)methyl)morpholine (prepared according to the method disclosed in the patent application "US20150361100A1"), accordingly, the title compound 47 (34.8%) was prepared.

MS m/z (ESI): 422.4 [M+1]

$^1$H NMR (400 MHz, DMSO-d$_6$) δ 9.37 (s, 1H), 7.58 (s, 1H), 7.48-7.33 (m, 5H), 7.05 (s, 1H), 3.35-3.28 (m, 6H), 2.11 (s, 2H), 1.90-1.87 (m, 4H).

Example 48

8-(2-Methyl-6-(morpholinomethyl)pyridin-4-yl)-7-phenyl-[1,2,4]triazolo[4,3-c]pyrimidin-5-amine 48

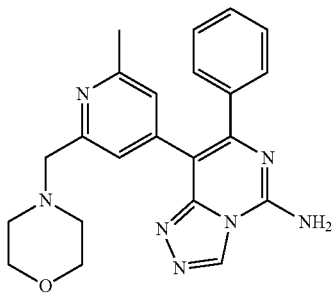

48

In accordance with the synthetic route of Example 43, the starting compound 43a in Step 1 was replaced with morpholine 48a, accordingly, the title compound 48 (30.8 mg) was prepared.

MS m/z (ESI): 402.5 [M+1]

$^1$H NMR (400 MHz, DMSO-d$_6$) δ 9.34 (s, 1H), 8.23 (brs, 2H), 7.35-7.28 (m, 6H), 6.85 (s, 1H), 3.42-3.35 (m, 6H), 2.44 (s, 3H), 2.13-2.05 (m, 4H).

Example 49

7-(4-Chloro-2-fluorophenyl)-8-(2-methyl-6-(trifluoromethyl)pyridin-4-yl)-[1,2,4]triazolo[4,3-c]pyrimidin-5-amine

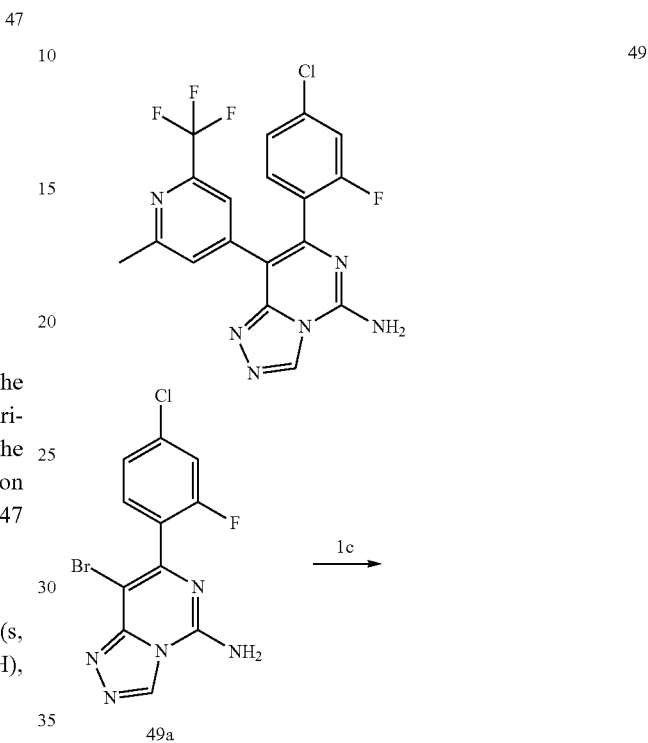

49

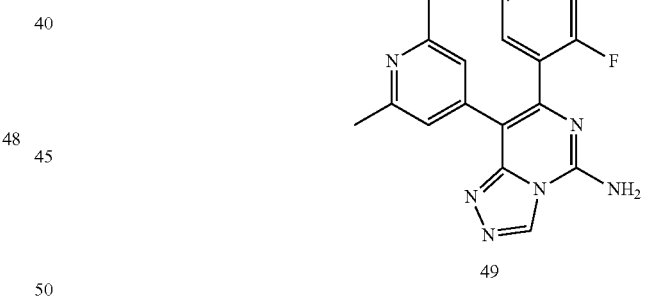

In accordance with the synthetic route of Example 15, the starting compound 15b in Step 1 was replaced with (4-chloro-2-fluorophenyl)boronic acid (Accela ChemBio (Shanghai) Inc.), accordingly, 8-bromo-7-(4-chloro-2-fluorophenyl)-[1,2,4]triazolo[4,3-c]pyrimidin-5-amine 49a was prepared.

The starting compound 4a in Step 5 of Example 15 was replaced with compound 1c, accordingly, the title compound 49 (20 mg) was prepared.

MS m/z (ESI): 422.7 [M+1]

$^1$H NMR (400 MHz, DMSO-d$_6$) δ 9.43 (s, 1H), 8.54 (brs, 2H), 7.56-7.52 (m, 2H), 7.45 (s, 1H), 7.42-7.38 (m, 2H), 2.48 (s, 3H).

Example 50

7-(4-Chloro-2-fluorophenyl)-8-(2-chloro-6-methylpyridin-4-yl)-[1,2,4]triazolo[4,3-c]pyrimidin-5-amine 50

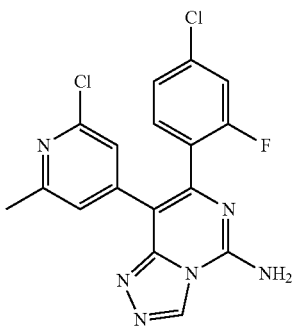

50

In accordance with the synthetic route of Example 15, the starting compound 15b in Step 1 was replaced with (4-chloro-2-fluorophenyl)boronic acid (Accela ChemBio (Shanghai) Inc.), accordingly, the title compound 50 (30 mg) was prepared.

MS m/z (ESI): 389.4 [M+1]

¹H NMR (400 MHz, DMSO-d₆) δ 9.41 (s, 1H), 8.47 (brs, 2H), 7.54-7.50 (m, 1H), 7.44-7.39 (m, 2H), 7.18 (s, 1H), 7.14 (s, 1H), 2.36 (s, 3H).

Example 51

8-(2-(Difluoromethyl)-6-methylpyridin-4-yl)-7-(4-fluorophenyl)-[1,2,4]triazolo[4,3-c]pyrimidin-5-amine 51

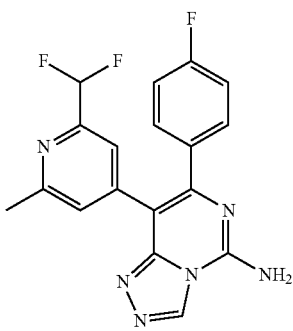

51

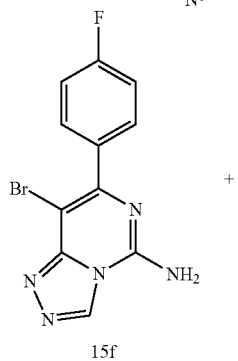

15f

+

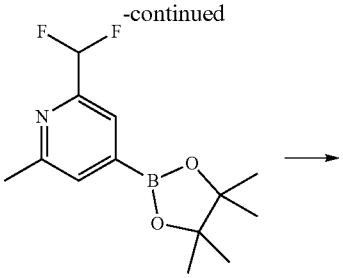

20a

→

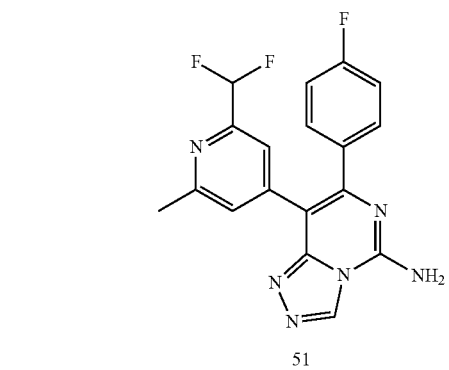

51

Compound 15f (1.00 g, 3.25 mmol), compound 20a (1.05 g, 3.90 mmol), [1,1'-bis(diphenylphosphino)ferrocene]dichloropalladium (238 mg, 324.6 μmop and sodium bicarbonate (682 mg, 8.11 mmol) were added successively to 55 mL of a mixed solution of 1,4-dioxane and water (V/V=9:2) under an argon atmosphere. The reaction solution was heated to 95° C., and stirred for 17 hours. The reaction solution was cooled to room temperature and filtrated. The filtrate was concentrated under reduced pressure, and the residue was purified by high performance liquid chromatography (Waters 2767-SQ Detecor2, elution system: ammonium bicarbonate, water, acetonitrile) to obtain the title compound 51 (50 mg).

MS m/z (ESI): 371.2 [M+1]

¹H NMR (400 MHz, DMSO-d₆) δ 9.37 (s, 1H), 8.38 (brs, 2H), 7.44 (s, 1H), 7.39-7.36 (m, 2H), 7.32 (s, 1H), 7.19-7.14 (m, 2H), 6.98-6.70 (m, 1H), 2.46 (s, 3H).

Example 52

7-(4-Chlorophenyl)-8-(2-(difluoromethyl)-6-methylpyridin-4-yl)-[1,2,4]triazolo[4,3-c]pyrimidin-5-amine 52

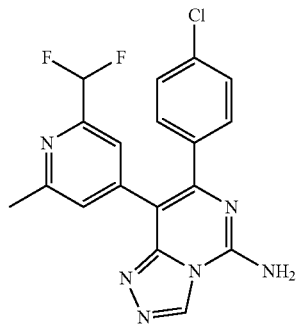

52

In accordance with the synthetic route of Example 14, the starting compound 1c was replaced with compound 20a, accordingly, the title compound 52 (32 mg) was prepared.

MS m/z (ESI): 387.0 [M+1]

$^1$H NMR (400 MHz, DMSO-d$_6$) δ 9.37 (s, 1H), 8.39 (brs, 2H), 7.40-7.43 (m, 2H), 7.33-7.38 (m, 4H), 6.84 (t, 1H), 2.46 (s, 3H).

Example 53

7-(4-Chlorophenyl)-8-(2-(fluoromethyl)-6-methylpyridin-4-yl)-[1,2,4]triazolo[4,3-c]pyrimidin-5-amine 53

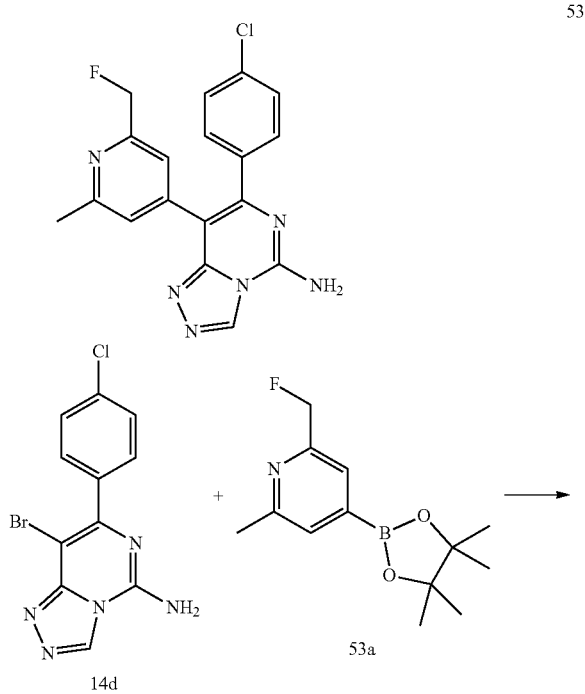

In accordance with the synthetic route of Example 14, the starting compound 1c was replaced with compound 2-(fluoromethyl)-6-methyl-4-(4,4,5,5-tetramethyl-1,3,2-dioxaborolan-2-yl)pyridine 53a (prepared according to the method disclosed in the patent application "WO201195625A1"), accordingly, the title compound 53 (4 mg) was prepared.

MS m/z (ESI): 369.1 [M+1]

$^1$H NMR (400 MHz, DMSO-d$_6$) δ 9.36 (s, 1H), 8.36 (brs, 2H), 7.42-7.32 (m, 3H), 7.19 (s, 1H), 5.42-5.30 (m, 2H), 7.19-7.14 (m, 2H), 2.40 (s, 3H).

Example 54

7-(4-Chlorophenyl)-8-(2,6-dimethylpyridin-4-yl)-[1,2,4]triazolo[4,3-c]pyrimidin-5-amine 54

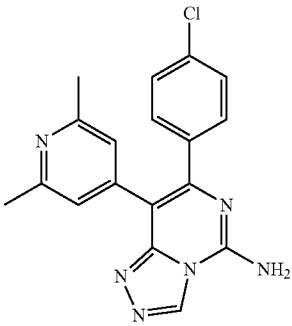

In accordance with the synthetic route of Example 14, the starting compound 1c was replaced with compound 11a, accordingly, the title compound 54 (47.5 mg) was prepared.

MS m/z (ESI): 351.1 [M+1]

$^1$H NMR (400 MHz, DMSO-d$_6$) δ 9.34 (s, 1H), 8.27 (brs, 2H), 7.39-7.33 (m, 4H), 6.96 (s, 2H), 2.34 (s, 6H).

Example 55

8-(2-(Fluoromethyl)-6-methylpyridin-4-yl)-7-(4-fluorophenyl)-[1,2,4]triazolo[4,3-c]pyrimidin-5-amine 55

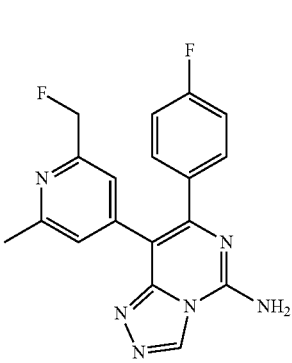

In accordance with the synthetic route of Example 15, the starting compound 4a was replaced with compound 53a, accordingly, the title compound 55 (20 mg) was prepared.

MS m/z (ESI): 353.2 [M+1]

$^1$H NMR (400 MHz, DMSO-d$_6$) δ 9.36 (s, 1H), 8.31 (brs, 2H), 7.40-7.36 (m, 2H), 7.20-7.13 (m, 4H), 5.42-5.31 (m, 2H), 2.41 (s, 3H).

Example 56

8-(2-(Difluoromethyl)-6-methylpyridin-4-yl)-7-(2-fluorophenyl)-[1,2,4]triazolo[4,3-c]pyrimidin-5-amine 56

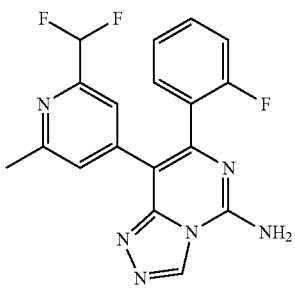

In accordance with the synthetic route of Example 19, the starting compound 11a was replaced with compound 20a, accordingly, the title compound 56 (105.6 mg) was prepared.

MS m/z (ESI): 371.1 [M+1]

$^1$H NMR (400 MHz, DMSO-d$_6$) δ 9.53 (s, 1H), 8.50 (brs, 2H), 7.47-7.42 (m, 2H), 7.37 (s, 1H), 7.31 (s, 1H), 7.26-7.24 (m, 1H), 7.13-7.11 (m, 1H), 6.94-6.66 (m, 1H), 2.41 (s, 3H).

Example 57

8-(2-(Fluoromethyl)-6-methylpyridin-4-yl)-7-(2-fluorophenyl)-[1,2,4]triazolo[4,3-c]pyrimidin-5-amine 57

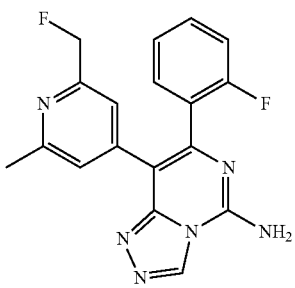

In accordance with the synthetic route of Example 19, the starting compound 11a was replaced with compound 53a, accordingly, the title compound 57 (58 mg) was prepared.

MS m/z (ESI): 353.2 [M+1]

$^1$H NMR (400 MHz, METHANOL-d$_4$) δ 9.29 (s, 1H), 7.51-7.48 (m, 1H), 7.43-7.41 (m, 1H), 7.26-7.21 (m, 3H), 7.04-6.99 (m, 1H), 5.37-5.25 (m, 2H), 2.45 (s, 3H).

Example 58

7-(2,4-Difluorophenyl)-8-(2-(fluoromethyl)-6-methylpyridin-4-yl)-[1,2,4]triazolo[4,3-c]pyrimidin-5-amine 58

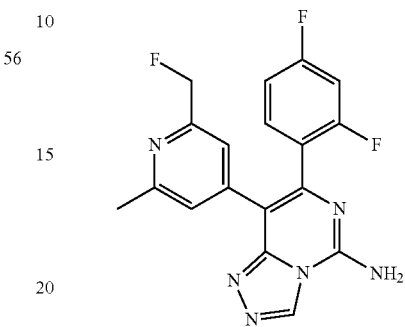

In accordance with the synthetic route of Example 18, the starting compound 1c was replaced with compound 53a, accordingly, the title compound 58 (30 mg) was prepared.

MS m/z (ESI): 371.1 [M+1]

$^1$H NMR (400 MHz, CD$_3$OD) δ 9.29 (s, 1H), 7.59-7.55 (m, 1H), 7.27-7.25 (m, 2H), 7.06-7.02 (m, 1H), 6.91-6.86 (m, 1H), 5.40-5.28 (m, 2H), 2.48 (s, 3H).

Example 59

7-(4-Chloro-2-fluorophenyl)-8-(2-(difluoromethyl)-6-methylpyridin-4-yl)-[1,2,4]triazolo[4,3-c]pyrimidin-5-amine 59

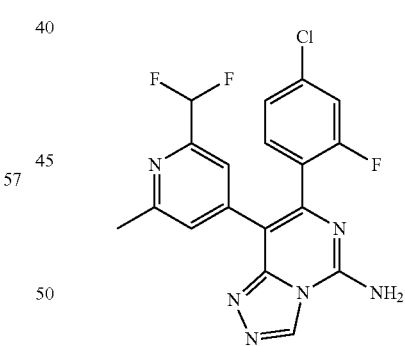

In accordance with the synthetic route of Example 49, the starting compound 1e was replaced with compound 20a, accordingly, the title compound 59 (49.1 mg) was prepared.

MS m/z (ESI): 405.1 [M+1]

$^1$H NMR (400 MHz, DMSO-d$_6$) δ 9.42 (s, 1H), 7.54-7.50 (m, 1H), 7.40-7.30 (m, 4H), 6.97-6.69 (m, 1H), 3.43 (brs, 2H), 2.44 (s, 3H).

TEST EXAMPLES

Biological Assay

Test Example 1. Determination of the inhibition activity of the compounds of the present invention on the adenosine A$_{2a}$ receptor (A$_{2a}$R) cAMP signaling pathway, the adenosine A$_{2b}$ receptor (A$_{2b}$R) cAMP signaling pathway, the adenosine A$_1$ receptor (A$_1$R) cAMP signaling pathway and the adenosine A$_3$ receptor (A$_3$R) cAMP signaling pathway.

The inhibition activity of the compounds of the present invention on the adenosine A$_{2a}$ receptor cAMP signaling pathway, the adenosine A$_{2b}$ receptor cAMP signaling pathway, the adenosine A$_1$ receptor cAMP signaling pathway and the adenosine A$_3$ receptor cAMP signaling pathway was determined by the following method. The experimental method is briefly described as follows:

I. Experimental Materials and Instruments

1. CHO-K1/A$_{2a}$R cells (NM_000675.5) or CHO-K1/A$_{2b}$R cells (NM_000676.2) or CHO-K1/A$_1$R cells (NM_000674.2) or CHO-K1/A$_3$R cells (NM_000677.3)
2. Fetal bovine serum (Gibco, 10099-141)
3. Bleomycin (Thermo, R25001) or G418 (ENZO, ALX-380-013-G005) or puromycin (Thermo, 10687-010)
4. DMEM/F12 medium (GE, SH30023.01)
5. Cell separation buffer (Thermo Fisher, 13151014)
6. HEPES (Gibco, 42360-099)
7. Bovine serum albumin (MP Biomedicals, 219989725)
8. Rolipram (sigma, R6520-10MG)
9. Adenosine deaminase (sigma, 10102105001)
10. Forskolin (sigma, F6886)
11. 2C1-IB-MECA (Tocrics, 1104/10)
12. N6-cyclopentyladenosine (Tocris, 1702/50)
13. Balanced salt buffer (Thermo, 14025-092)
14. cAMP dynamic 2 kit (Cisbio, 62AM4PEB)
15. 384-well plate (Corning, 4514) or (Nunc, 267462#)
16. Ethyl carbazole (Torcis, 1691/10)
17. PHERAstar multi-function microplate reader (Cisbio, 62AM4PEB)

II. Experimental Procedures 2.1 Adenosine A$_{2a}$ Receptor

CHO-K1/A$_{2a}$R cells were cultured in DMEM/F12 medium containing 10% fetal bovine serum and 800 µg/ml bleomycin. The cells were digested with the cell separation buffer during the experiment. The cells were resuspended in the balanced salt buffer containing 20 mM HEPES and 0.1% bovine serum albumin and counted, and the cell density was adjusted to $10^6$ cells/ml. In the 384-well plate, each well was added with 5 µl of cell suspension, and 2.5 µl of test compound (4× concentration) formulated with the balanced salt buffer containing 20 mM HEPES, 0.1% bovine serum albumin, 54 µM rolipram and 2.7 U/ml adenosine deaminase, and the plate was incubated at room temperature for 30 minutes. Each well was then added with 2.5 µl of ethyl carbazole (4× concentration) formulated with the balanced salt buffer containing 20 mM HEPES, 0.1% bovine serum albumin, 54 µM rolipram and 2.7 U/ml adenosine deaminase, and the plate was incubated at room temperature for 30 minutes. The final concentrations of the compounds were: 10000, 2000, 400, 80, 16, 3.2, 0.64, 0.128, 0.0256, 0.00512, and 0.001024 nM. The final concentration of ethyl carbazole was 20 nM. Intracellular cAMP concentration was detected with the cAMP dynamic 2 kit. cAMP-d2 and Anti-cAMP-Eu-Cryptate were diluted respectively with the cAMP lysis buffer at a ratio of 1:4. Each well was added with 5 µl of diluted cAMP-d2, followed by addition of 5 µl of diluted Anti-cAMP-Eu-Cryptate, and the plate was incubated at room temperature in the dark for 1 hour. The HTRF signal values were read by the PHERAstar multi-function microplate reader. IC$_{50}$ values of inhibition activity of the compounds were calculated by Graphpad Prism software, and are shown in Table 1.

2.2 Adenosine A$_1$ receptor

CHO-K1/A$_1$R cells were cultured in DMEM/F12 medium containing 10% fetal bovine serum and 1 mg/ml G418. The cells were digested with the cell separation buffer during the experiment. The cells were then resuspended in the balanced salt buffer containing 20 mM HEPES and 0.1% bovine serum albumin and counted, and the cell density was adjusted to 5×10$^5$ cells/ml. In the 384-well plate, each well was added with 12.5 µl of cell suspension, and 6.25 µl of test compound (4× concentration) formulated with the balanced salt buffer containing 20 mM HEPES, 0.1% bovine serum albumin, 54 µM rolipram and 2.7 U/ml adenosine deaminase, and the plate was incubated at room temperature for 30 minutes. Each well was then added with 6.25 µl of forskolin and N6-cyclopentyladenosine (4× concentration) formulated with the balanced salt buffer containing 20 mM HEPES, 0.1% bovine serum albumin, 54 µM rolipram and 2.7 U/ml adenosine deaminase, and the plate was incubated at room temperature for 30 minutes. The final concentrations of the compounds were: 100000, 10000, 1000, 100, 10, 1, 0.1 and 0 nM. The final concentration of forskolin was 10 µM. The final concentration of CPA was 10 nM. Intracellular cAMP concentration was detected with the cAMP dynamic 2 kit. cAMP-d2 and Anti-cAMP-Eu-Cryptate were diluted respectively with the cAMP lysis buffer at a ratio of 1:4. Each well was added with 12.5 µl of diluted cAMP-d2, followed by addition of 12.5 µl of diluted Anti-cAMP-Eu-Cryptate, and the plate was incubated at room temperature in the dark for 1 hour. The HTRF signal values were read by the PHERAstar multi-function microplate reader. IC$_{50}$ values of inhibition activity of the compounds were calculated by Graphpad Prism software, and are shown in Table 2.

2.3 Adenosine A$_3$ receptor

CHO-K1/A$_3$R cells were cultured in DMEM/F12 medium containing 10% fetal bovine serum and 10 µg/ml puromycin. The cells were digested with the cell separation buffer during the experiment. The cells were resuspended in the balanced salt buffer containing 20 mM HEPES and 0.1% bovine serum albumin and counted, and the cell density was adjusted to 5×10$^5$ cells/ml. In the 384-well plate, each well was added with 12.5 µl of cell suspension, and 6.25 µl of test compound (4× concentration) formulated with the balanced salt buffer containing 20 mM HEPES, 0.1% bovine serum albumin, 54 µM rolipram and 2.7 U/ml adenosine deaminase, and the plate was incubated at room temperature for 30 minutes. Each well was then added with 6.25 µl of forskolin and 2Cl-IB-MECA (4× concentration) formulated with the balanced salt buffer containing 20 mM HEPES, 0.1% bovine serum albumin, 54 µM rolipram and 2.7 U/ml adenosine deaminase, and the plate was incubated at room temperature for 30 minutes. The final concentrations of the compounds were: 100000, 10000, 1000, 100, 10, 1, 0.1 and 0 nM. The final concentration of forskolin was 10 µM. The final concentration of 2Cl-IB-MECA was 5 nM. Intracellular cAMP concentration was detected with the cAMP dynamic 2 kit. cAMP-d2 and Anti-cAMP-Eu-Cryptate were diluted respectively with the cAMP lysis buffer at a ratio of 1:4. Each well was added with 12.5 µl of diluted cAMP-d2, followed by addition of 12.5 µl of diluted Anti-cAMP-Eu-Cryptate, and the plate was incubated at room temperature in the dark for 1 hour. The HTRF signal values were read by the PHERAstar multi-function microplate reader. ICH) values of inhibition activity of the compounds were calculated by Graphpad Prism software, and are shown in Table 2.

2.4 Adenosine $A_{2b}$ receptor ($A_{2b}R$)

CHO-K1/$A_{2b}$R cells were cultured in DMEM/F12 medium containing 10% fetal bovine serum and 1 mg/ml G418. The cells were digested with the cell separation buffer during the experiment. The cells were resuspended in the balanced salt buffer containing 20 mM HEPES and 0.1% bovine serum albumin and counted, and the cell density was adjusted to $10^6$ cells/ml. In the 384-well plate, each well was added with 5 μl of cell suspension, and 2.5 μl of test compound (4× concentration) formulated with the balanced salt buffer containing 20 mM HEPES, 0.1% bovine serum albumin, 54 μM rolipram and 2.7 U/ml adenosine deaminase, and the plate was incubated at room temperature for 30 minutes. Each well was then added with 2.5 μl of ethyl carbazole (4× concentration) (Torcis, 1691/10) formulated with the balanced salt buffer containing 20 mM HEPES, 0.1% bovine serum albumin, 54 μM rolipram and 2.7 U/ml adenosine deaminase, and the plate was incubated at room temperature for 30 minutes. The final concentrations of the compounds were: 100000, 10000, 1000, 100, 10, 1, 0.1 and 0 nM. The final concentration of ethyl carbazole was 1 μM. Intracellular cAMP concentration was detected with the cAMP dynamic 2 kit. cAMP-d2 and Anti-cAMP-Eu-Cryptate were diluted respectively with the cAMP lysis buffer at a ratio of 1:4. Each well was added with 5 μl of diluted cAMP-d2, followed by addition of 5 μl of diluted Anti-cAMP-Eu-Cryptate, and the plate was incubated at room temperature in the dark for 1 hour. The HTRF signal values were read by the PHERAstar multi-function microplate reader. $IC_{50}$ values of inhibition activity of the compounds were calculated by Graphpad Prism software, and are shown in Table 3.

TABLE 1

$IC_{50}$ values of the inhibition activity of the compounds of the present invention on the adenosine $A_{2a}$ receptor cAMP signaling pathway

| Example No. | $IC_{50}$/nM ($A_{2a}R$) |
|---|---|
| 1 | 0.23 |
| 3 | 0.07 |
| 4 | 0.08 |
| 5 | 0.09 |
| 6 | 0.14 |
| 7 | 0.16 |
| 8 | 0.18 |
| 9 | 0.25 |
| 10 | 0.26 |
| 11 | 0.15 |
| 12 | 0.63 |
| 14 | 1.56 |
| 15 | 0.17 |
| 16 | 0.63 |
| 17 | 0.75 |
| 18 | 3.96 |
| 19 | 0.96 |
| 20 | 2.33 |
| 21 | 2.46 |
| 23 | 0.23 |
| 24 | 0.27 |
| 25 | 0.32 |
| 26 | 0.42 |
| 27 | 0.5 |
| 28 | 0.52 |
| 29 | 0.55 |
| 30 | 0.77 |
| 31 | 0.93 |
| 32 | 1 |
| 33 | 1.77 |
| 34 | 2.04 |
| 35 | 0.18 |
| 36 | 3.47 |
| 37 | 2.11 |
| 38 | 2.18 |
| 40 | 1.75 |
| 43 | 0.2 |
| 50 | 3.55 |
| 51 | 0.36 |
| 52 | 0.48 |
| 53 | 0.35 |
| 54 | 0.48 |
| 55 | 1.04 |
| 56 | 1.68 |
| 57 | 2.59 |
| 59 | 3.05 |

Conclusion: The compounds of the present invention have a significant inhibition activity on the adenosine $A_{2a}$ receptor cAMP signaling pathway.

TABLE 2

$IC_{50}$ values of the inhibition activity of the compounds of the present invention on the adenosine $A_1$ receptor cAMP signaling pathway and the adenosine $A_3$ receptor cAMP signaling pathway

| Example No. | $IC_{50}$/nM ($A_{2a}R$) | $IC_{50}$/nM ($A_1R$) | $IC_{50}$ ratio ($A_1R/A_{2a}R$) | $IC_{50}$/nM ($A_3R$) | $IC_{50}$ ratio ($A_3R/A_{2a}R$) |
|---|---|---|---|---|---|
| 3 | 0.07 | 18 | 257 | $2 \times 10^3$ | $2.9 \times 10^4$ |
| 4 | 0.08 | 37 | 463 | $>10^4$ | $>1.3 \times 10^5$ |
| 5 | 0.09 | 12 | 133 | $1.4 \times 10^3$ | $1.5 \times 10^4$ |
| 7 | 0.16 | 16 | 100 | $5 \times 10^3$ | $3.1 \times 10^4$ |
| 11 | 0.15 | 102 | 680 | $>10^4$ | $>6.7 \times 10^4$ |
| 18 | 3.96 | 409 | 103 | $>10^4$ | $>2.5 \times 10^3$ |
| 19 | 0.96 | 173 | 180 | $>10^4$ | $>10^4$ |
| 20 | 2.33 | 519 | 223 | $>10^4$ | $>4.3 \times 10^3$ |
| 27 | 0.5 | 71 | 142 | $>10^4$ | $>2 \times 10^4$ |
| 28 | 0.52 | 66 | 127 | $>10^4$ | $>1.9 \times 10^4$ |
| 51 | 0.36 | 418 | 1161 | $>10^4$ | $>10^4$ |
| 52 | 0.48 | 41 | 85 | $>10^4$ | $>10^4$ |
| 55 | 1.04 | 222.5 | 214 | $>10^4$ | $>10^3$ |
| 56 | 1.68 | 248 | 148 | $>10^4$ | $>10^3$ |
| 57 | 2.59 | 302.4 | 117 | $>10^4$ | $>10^3$ |
| 59 | 3.05 | 1009 | 330 | $>10^4$ | $>10^3$ |

Conclusion: The compounds of the present invention have a weak inhibition activity on the adenosine $A_1$ receptor and the adenosine $A_3$ receptor, indicating that the compounds of the present invention are highly selective for the adenosine $A_{2a}$ receptor.

TABLE 3

$IC_{50}$ values of the inhibition activity of the compounds of the present invention on the adenosine $A_{2b}$ receptor cAMP signaling pathway

| Example No. | $IC_{50}$/nM ($A_{2a}R$) | $IC_{50}$/nM ($A_{2b}R$) | $IC_{50}$ ratio ($A_{2b}R/A_{2a}R$) |
|---|---|---|---|
| 1 | 0.23 | 58.5 | 254 |
| 4 | 0.08 | 82.6 | 1032 |
| 8 | 0.18 | 202.6 | 1125 |
| 10 | 0.26 | 91 | 350 |
| 15 | 0.17 | 98.9 | 582 |
| 16 | 0.63 | 122.2 | 194 |
| 18 | 0.75 | 793.1 | 1057 |
| 19 | 0.96 | 85.4 | 89 |
| 20 | 2.33 | 522.3 | 224 |
| 29 | 0.55 | 86.3 | 157 |

TABLE 3-continued

IC$_{50}$ values of the inhibition activity of the compounds of the present invention on the adenosine A$_{2b}$ receptor cAMP signaling pathway

| Example No. | IC$_{50}$/ nM (A$_{2a}$R) | IC$_{50}$/ nM (A$_{2b}$R) | IC$_{50}$ ratio (A$_{2b}$R/A$_{2a}$R) |
|---|---|---|---|
| 30 | 0.77 | 70.9 | 92 |
| 33 | 1.77 | 134.5 | 76 |
| 34 | 2.04 | 169.9 | 83 |
| 50 | 3.55 | 254.7 | 72 |
| 55 | 1.04 | 78.2 | 75 |
| 56 | 1.68 | 111.9 | 67 |
| 57 | 2.59 | 209.2 | 81 |
| 59 | 3.05 | 883.8 | 290 |

Conclusion: The compounds of the present invention have a weak inhibition activity on the adenosine A$_{2b}$ receptor, indicating that the compounds of the present invention are highly selective for the adenosine A$_{2a}$ receptor.

Test Example 2. Determination of the Brain Permeability of the Compounds of the Present Invention in Mice The brain permeability of the compounds of the present invention in mice was determined by the following experimental method:

I. Experimental Materials and Instruments

1. RED Device Inserts (Thermo Scientific, QL21291110)
2. API 4000 Q-trap linear ion trap mass spectrometer (Applied Biosystems)
3. LC-30A ultra high pressure liquid chromatography system (Shimadzu)
4. pH 7.4 PBS (100 mM, stored at 4° C. in a refrigerator)
5. C57 mice, provided by Jiesijie Laboratory Animal Co., LTD, with Certificate No.: SCXK (Shanghai) 2013-0006.

II. Treatment of the Test Animals

Four female C57 mice were maintained on a 12 hours light/12 hours dark cycle, in a constant temperature of 24±3° C. and a humidity of 50-60%, and had free access to food and water. The compounds were administered intragastrically to the mice after fasting overnight. The administration dosage was 20 mg/kg. The drug administration group was sacrificed after blood collection at 0.5 h after drug administration (collected blood volume: 0.5 ml). The blood sample was stored in heparinized tubes, and centrifuged for 10 minutes at 3500 rpm to separate the plasma, which was marked as plasma 1 and stored at −80° C. Normal saline was perfused to the heart of the sacrificed animal to remove excess blood from the brain tissue. The brain tissue was taken, and the residual blood in the brain tissue was sucked with a filter paper. The brain tissue was marked as brain tissue 1, and stored at −80° C. Another three animals were taken for blank plasma and brain tissue 2, and the treatment method was the same as that of drug administration group.

III. Plasma Protein Binding Equilibrium Dialysis Process 3.1 Preparation of the Samples The drug compounds were dissolved in DMSO to 20 mM to obtain stock solution I. An appropriate amount of stock solution I was taken and diluted with methanol to obtain a 200 µM diluted stock solution II. 10 µl of stock solution II was taken to a 1.5 ml Eppendorf tube, added with 990 µl of blank plasma, and mixed well to obtain 2 µM plasma sample 2 (concentration of DMSO≤0.2%), which was used for the determination of plasma protein binding rate at this concentration. 50 µl of the above formulated plasma sample was taken, marked as T$_0$, and stored at −4° C. in a refrigerator for testing.

3.2 Experimental Procedures

The equilibrium dialysis tube of RED Device Inserts was inserted into a 96-well plate. 300 µl of the above formulated plasma sample 2 containing test compound and corresponding blank plasma sample were added to a red marked well (plasma chamber). 500 µl of phosphate buffer solution (pH 7.4) was added to another well (buffer chamber) side-by-side with the red marked well. According to the above procedures, each concentration of each compound had 2 samples. Then, the 96-well plate was covered by a sealing tape, and the entire plate was placed in a heat mixer and equilibrated at 37° C. at 400 rpm for 4 h. The 96-well plate device was removed from the heat mixer after incubation to achieve equilibrium dialysis. 25 µl of equilibrated plasma sample or dialysate sample was added with 25 µl of corresponding unequilibrated blank phosphate buffer solution free of drug or blank plasma free of drug, and then added with 200 µl of internal standard (formulated with acetonitrile), vortex-mixed for 5 min, and centrifuged for 10 minutes (4000 rpm). The supernatant was taken for LC/MS/MS analysis. T$_0$ sample was not subjected to incubation. The chromatographic peak area ratios of the total drug (plasma chamber) and the free drug (buffer chamber) to the internal standard were determined directly by the LC/MS/MS method established above respectively, and the free percent (f$_{uplasma}$%) was calculated.

IV. Brain Tissue Protein Binding Equilibrium Dialysis Process

Brain tissue protein binding equilibrium dialysis process: blank brain tissue 2 was formulated into a blank brain homogenate with PBS (pH 7.4) according to a dilution factor of 11, and added with the compound to formulate a 2 µM brain homogenate. Other procedures were the same as that of plasma protein binding. The chromatographic peak area ratios of the total drug (brain homo chamber) and the free drug (buffer chamber) to the internal standard were determined by the established LC/MS/MS method respectively, and the free percent (f$_{u\ brain\ hom}$%) was calculated.

V. Data Calculation Method of the Brain Permeability Test 5.1 The drug concentrations in plasma 1 and brain tissue 1 of mice 0.5 h after drug administration were determined by the established LC/MS/MS method respectively, which were the total concentration (C$_{total,\ p}$ and C$_{total,\ b}$);

5.2 The protein binding rates of the compound in the plasma and brain tissue of mice were determined respectively by equilibrium dialysis method with the RED Device Inserts device, so as to calculate the free percent (f$_{u\ plasma}$%, f$_{u\ brain}$%);

Free percent of plasma (f$_{u\ plasma}$%)=C$_{buffer}$/C$_{plasma}$×100%;

Free percent of brain homogenate (f$_{u\ brain\ hom}$%)= C$_{buffer}$/C$_{brain\ hom}$×100%;

Free percent of brain tissue (f$_{u\ brain}$%)=f$_{u\ brain\ hom}$/ (Df−(Df−1)×f$_{u\ brain\ hom}$)×100%, with Df=11.

5.3 The blood-brain permeability index Kp-unbound was calculated using the following formula.

$$Kp, \text{unbound} = \frac{C_{u,b}}{C_{u,p}} = \frac{C_{total,b} \times f_{u,b}}{C_{total,p} \times f_{u,p}} = Kp \times \left(\frac{f_{u,b}}{f_{u,p}}\right)$$

VI. Test Results and Discussion

The brain permeability indexes of the compounds of the present invention are shown below:

| Example No. | Blood-brain permeability index (Kp-unbound) |
|---|---|
| Example 18 | 0.010 |
| Example 20 | 0.015 |

Conclusion: The compounds of the present invention have a low concentration of free drug in brain, the ability to pass the blood-brain barrier is weak, and fewer drug enters the brain, which may have low side effects.

What is claimed is:

1. A compound of formula (I):

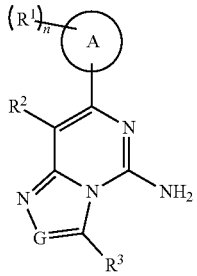

(I)

or a tautomer, mesomer, racemate, enantiomer, diastereomer thereof, or mixture thereof, or a pharmaceutically acceptable salt thereof,
wherein:
G is N;
ring A is cycloalkyl or aryl;
each $R^1$ is identical or different and each is independently selected from the group consisting of hydrogen, halogen, $C_{1-6}$ alkyl, $C_{1-6}$ alkoxy, and $C_{1-6}$ haloalkyl;
$R^2$ is selected from the group consisting of pyridyl, pyrazolyl, quinolinyl, pyridinone and indazolyl, wherein the pyridyl, pyrazolyl, quinolinyl, pyridinone and indazolyl are each independently optionally substituted by one or more substituents selected from the group consisting of halogen, $C_{1-6}$ alkyl, $C_{1-6}$ alkoxy, $C_{1-6}$ haloalkyl, hydroxy, $C_{1-6}$ hydroxyalkyl, 3 to 6 membered cycloalkyl, and 6 to 10 membered aryl;
$R^3$ is selected from the group consisting of hydrogen, halogen, $C_{1-6}$ alkyl, $C_{1-6}$ alkoxy, $C_{1-6}$ haloalkyl, hydroxy, $C_{1-6}$ hydroxyalkyl, cyano, amino, nitro, 3 to 6 membered cycloalkyl, and 6 to 10 membered aryl; and
n is 1, 2, 3 or 4.

2. The compound according to claim 1, wherein $R^2$ is selected from the group consisting of pyridyl, pyrazolyl, quinolinyl, pyridinone and indazolyl, wherein the pyridyl, pyrazolyl, quinolinyl, pyridinone and indazolyl are each independently optionally substituted by one or more substituents selected from the group consisting of halogen, $C_{1-6}$ alkyl, $C_{1-6}$ haloalkyl, $C_{1-6}$ alkoxy, and 3 to 6 membered cycloalkyl.

3. The compound according to claim 1, being a compound of formula (II):

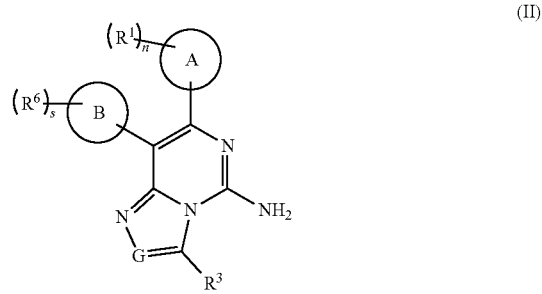

(II)

or a tautomer, mesomer, racemate, enantiomer, diastereomer thereof, or mixture thereof, or a pharmaceutically acceptable salt thereof,
wherein:
ring B is selected from the group consisting of pyridyl, pyrazolyl, quinolinyl, pyridinone and indazolyl;
each $R^6$ is identical or different and each is independently selected from the group consisting of hydrogen, halogen, $C_{1-6}$ alkyl, $C_{1-6}$ alkoxy, $C_{1-6}$ haloalkyl, hydroxy, $C_{1-6}$ hydroxyalkyl, and 3 to 6 membered cycloalkyl;
s is 0, 1, 2, 3 or 4; and
ring A, G, $R^1$, $R^3$, and n are as defined in claim 1.

4. The compound according to claim 1, being a compound of formula (III'):

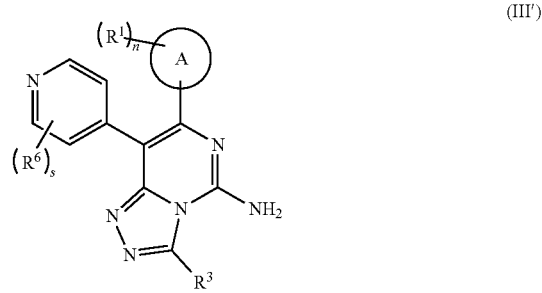

(III')

or a tautomer, mesomer, racemate, enantiomer, diastereomer thereof, or mixture thereof, or a pharmaceutically acceptable salt thereof,
wherein:
each $R^6$ is identical or different and each is independently selected from the group consisting of hydrogen, halogen, $C_{1-6}$ alkyl, $C_{1-6}$ haloalkyl, $C_{1-6}$ alkoxy, and 3 to 6 membered cycloalkyl;
s is 0, 1, 2, 3 or 4;
ring A, $R^1$, $R^3$, and n are as defined in claim 1.

5. The compound according to claim 1, wherein ring A is 6 membered aryl.

6. The compound according to claim 1, wherein $R^1$ is selected from the group consisting of hydrogen, halogen and $C_{1-6}$alkyl.

7. The compound according to claim 1, wherein R³ is selected from the group consisting of hydrogen, halogen and C₁₋₆alkyl.
8. The compound according to claim 1, wherein the compound is selected from the group consisting of:
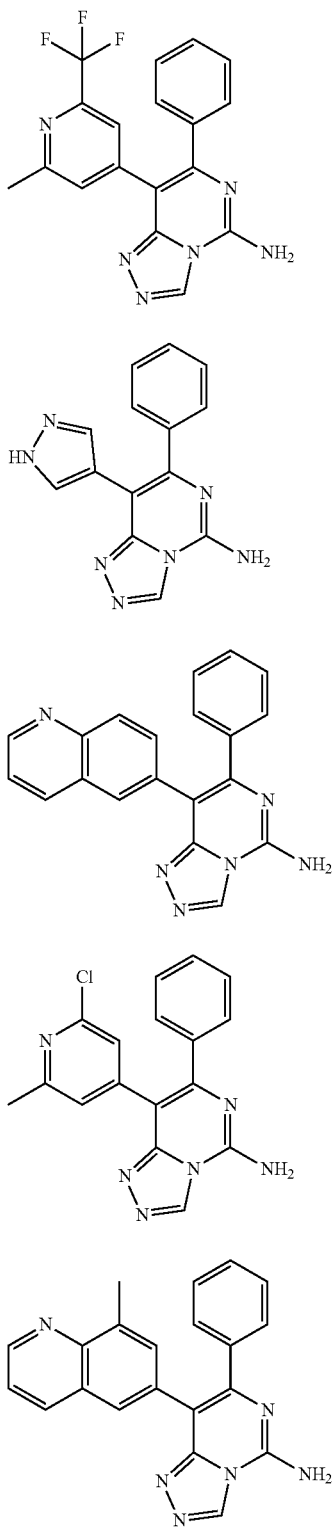
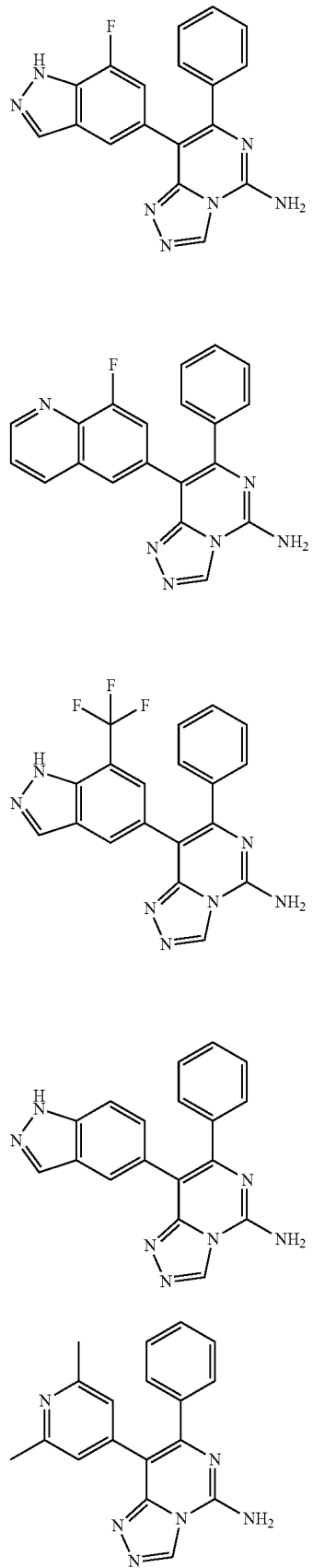

12
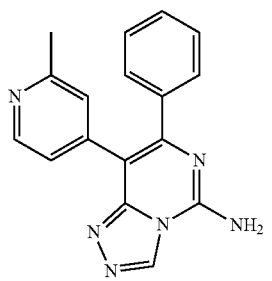
14
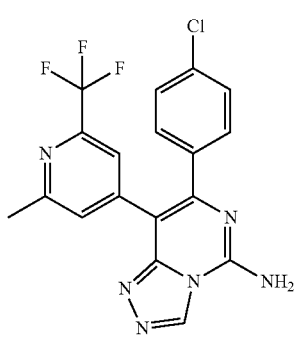
15
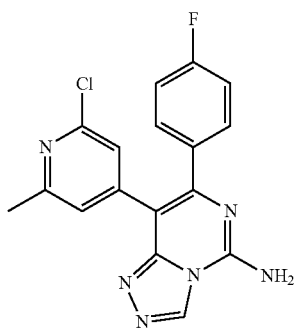
16
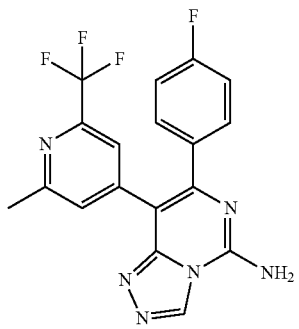
18
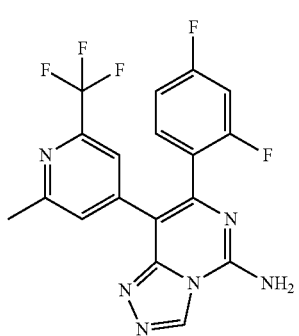
19
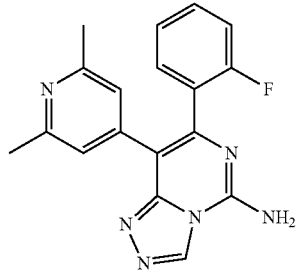
20
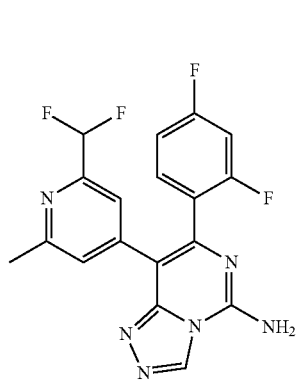
21
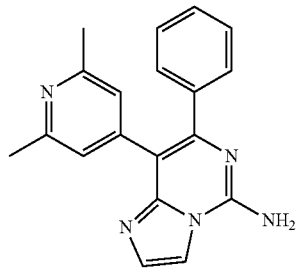
23
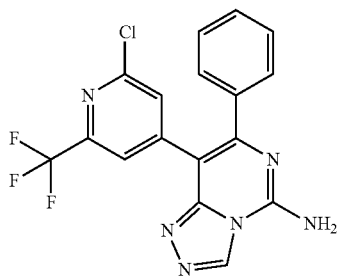
25
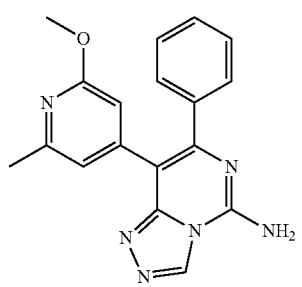

125
-continued
26
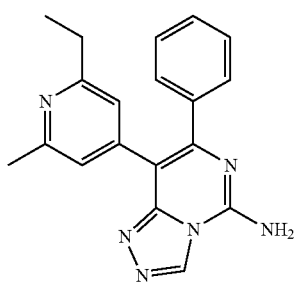
27
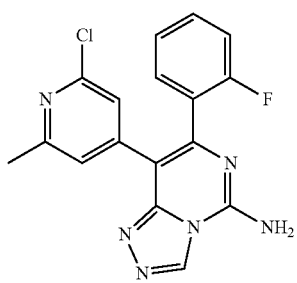
28
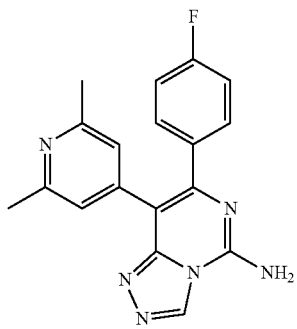
29
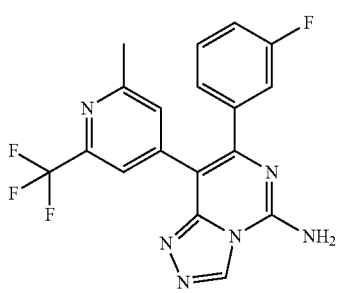
30
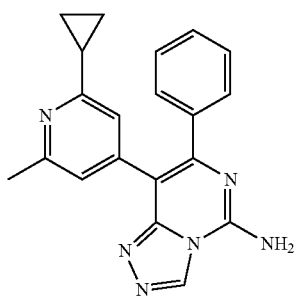
126
-continued
33
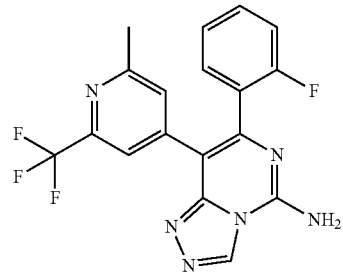
34
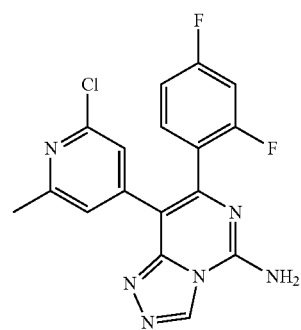
35
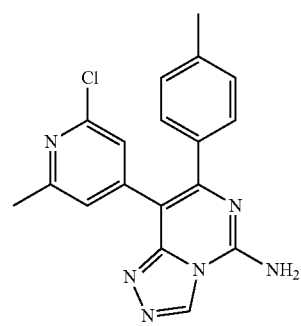
36
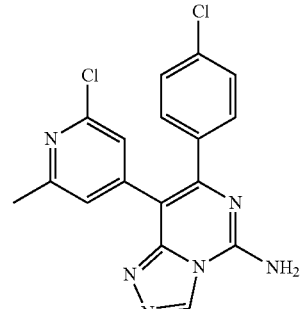
37
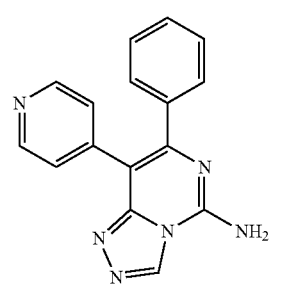

-continued
38
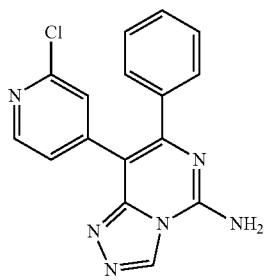
39
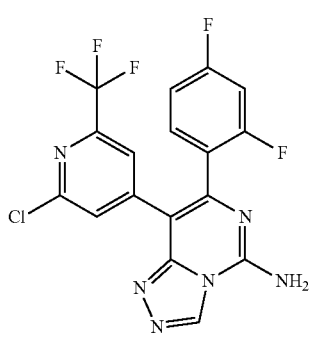
40
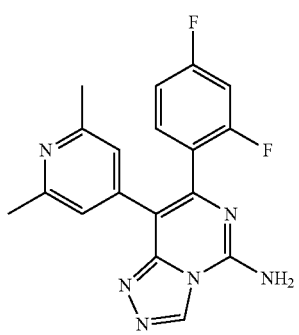
41
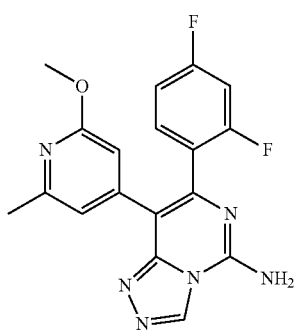
42
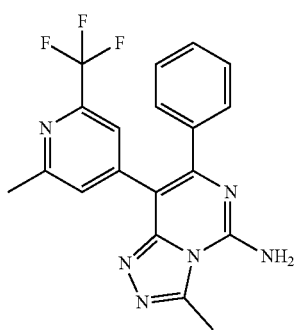
-continued
43
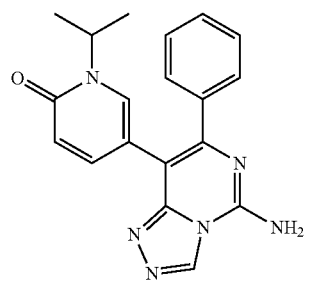
44
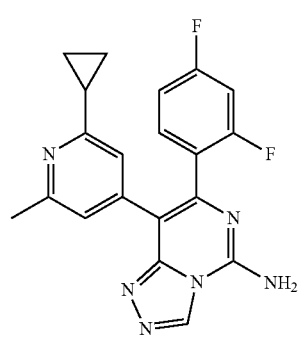
45
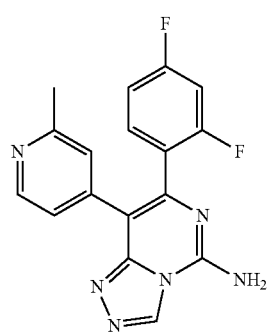
46
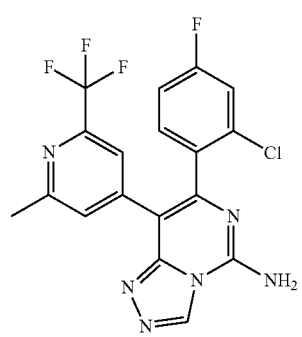
49
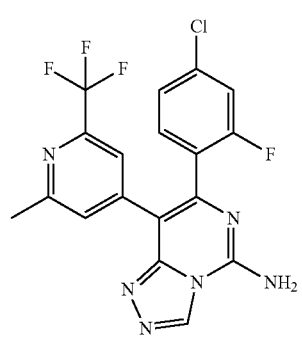

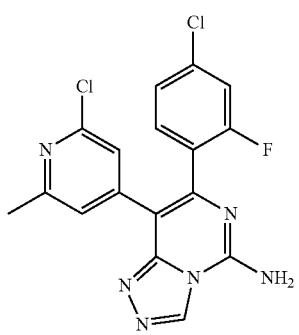
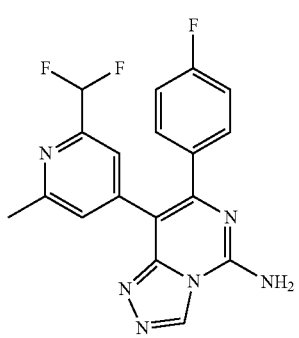
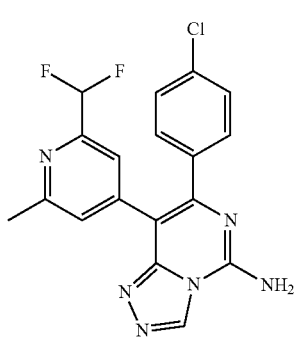
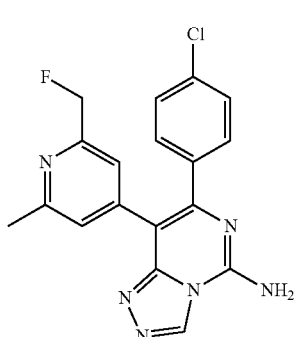
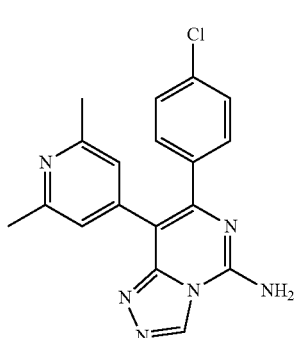
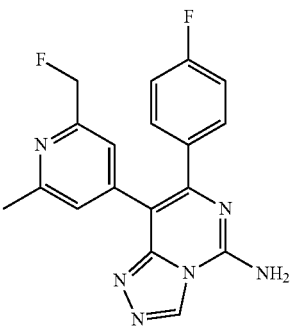
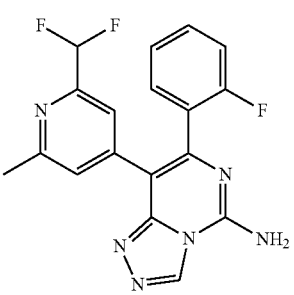
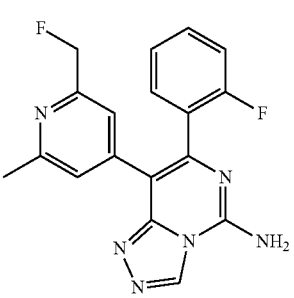
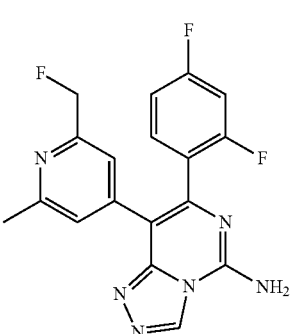
and
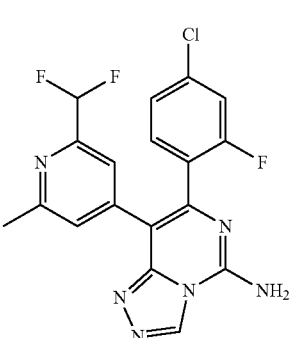
or a tautomer, mesomer, racemate, enantiomer, diastereomer thereof, or mixture thereof, or a pharmaceutically acceptable salt thereof.

9. A method for preparing the compound of formula (II) according to claim 3, comprising a step of:

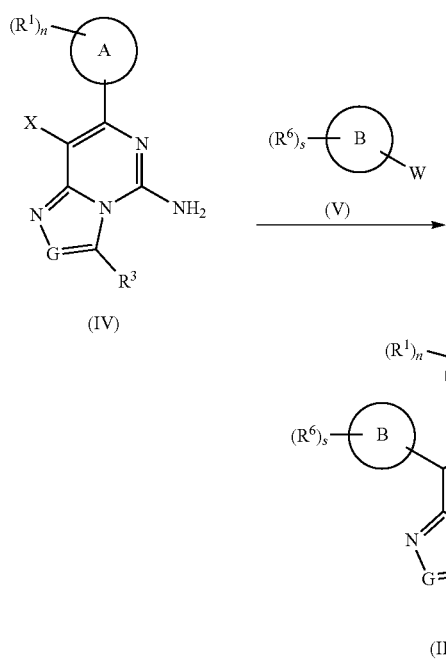

(IV)

(V)

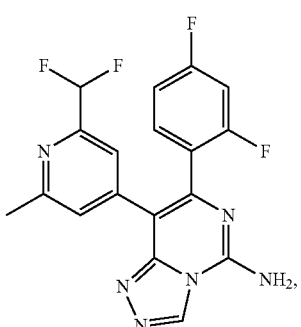

(II)

reacting a compound of formula (IV) with a compound of formula (V) to obtain the compound of formula (II), wherein:
X is a halogen;
W is

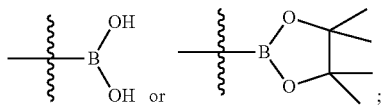

ring A, ring B, G, $R^1$, $R^3$, $R^6$, n and s are as defined in claim 3.

10. A pharmaceutical composition, comprising the compound claim 1, and one or more pharmaceutically acceptable carriers, diluents or excipients.

11. A method of treating a disease or condition ameliorated by inhibition of the $A_{2a}$ receptor in a patient in need thereof, the method comprising administering to the patient the pharmaceutical composition according to claim 10, wherein the disease or condition ameliorated by inhibition of the $A_{2a}$ receptor is tumor.

12. The compound according to claim 1, wherein ring A is phenyl.

13. A pharmaceutical composition comprising the compound according to claim 8, and one or more pharmaceutically acceptable carriers, diluents or excipients.

14. A method of treating a disease or condition ameliorated by inhibition of the $A_{2a}$ receptor in a patient in need thereof, the method comprising administering to the patient the pharmaceutical composition according to claim 13, wherein the disease or condition ameliorated by inhibition of the $A_{2a}$ receptor is tumor.

15. A compound of formula:

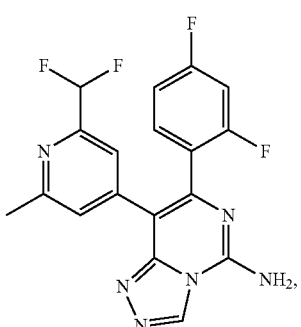

or a pharmaceutically acceptable salt thereof.

16. A compound of formula:

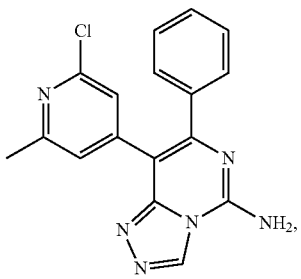

or a pharmaceutically acceptable salt thereof.

* * * * *